United States Patent
El-Hariry et al.

(10) Patent No.: US 8,906,885 B2
(45) Date of Patent: Dec. 9, 2014

(54) TREATING CANCER WITH HSP90 INHIBITORY COMPOUNDS

(75) Inventors: Iman El-Hariry, Boston, MA (US); David Proia, Newton, MA (US); Vojo Vukovic, Winchester, MA (US)

(73) Assignee: Synta Pharmaceuticals Corp., Lexington, MA (US)

( * ) Notice: Subject to any disclaimer, the term of this patent is extended or adjusted under 35 U.S.C. 154(b) by 0 days.

(21) Appl. No.: 14/131,183

(22) PCT Filed: Jul. 9, 2012

(86) PCT No.: PCT/US2012/045978
§ 371 (c)(1),
(2), (4) Date: Mar. 24, 2014

(87) PCT Pub. No.: WO2013/006864
PCT Pub. Date: Jan. 10, 2013

(65) Prior Publication Data
US 2014/0294808 A1    Oct. 2, 2014

Related U.S. Application Data

(60) Provisional application No. 61/623,762, filed on Apr. 13, 2012, provisional application No. 61/549,941, filed on Oct. 21, 2011, provisional application No. 61/505,322, filed on Jul. 7, 2011.

(51) Int. Cl.
| A61K 31/675  | (2006.01) |
| A61K 31/417  | (2006.01) |
| C07D 403/04  | (2006.01) |
| A61K 31/4196 | (2006.01) |
| A61K 45/06   | (2006.01) |
| A61K 31/4545 | (2006.01) |

(52) U.S. Cl.
CPC .......... *C07D 403/04* (2013.01); *A61K 31/4196* (2013.01); *A61K 45/06* (2013.01); *A61K 31/4545* (2013.01); *A61K 31/675* (2013.01); *A61K 31/417* (2013.01)
USPC ........................................... 514/80; 514/383

(58) Field of Classification Search
CPC ..................... A61K 31/675; A61K 31/417
USPC ................................................ 514/80, 383
See application file for complete search history.

(56) References Cited

U.S. PATENT DOCUMENTS

| 7,608,635 | B2 | 10/2009 | Ying et al. |
| 7,662,813 | B2 | 2/2010 | Ying et al. |
| 7,825,148 | B2 | 11/2010 | Ying et al. |
| 8,034,834 | B2 | 10/2011 | Du et al. |
| 8,053,456 | B2 | 11/2011 | Sun et al. |
| 8,063,083 | B2 | 11/2011 | Foley |
| 8,106,083 | B2 | 1/2012 | Burlison et al. |
| 8,183,384 | B2 | 5/2012 | Chimmanamada et al. |
| 8,188,075 | B2 | 5/2012 | Ying et al. |
| 8,299,107 | B2 | 10/2012 | Chimmanamada et al. |
| 8,318,790 | B2 | 11/2012 | Ying et al. |
| 8,329,736 | B2 | 12/2012 | Chimmanamada et al. |
| 8,329,899 | B2 | 12/2012 | Ying et al. |
| 8,362,055 | B2 | 1/2013 | Ying et al. |
| 8,415,377 | B2 | 4/2013 | Sun et al. |
| 8,450,500 | B2 | 5/2013 | Chimmanamada et al. |
| 8,486,932 | B2 | 7/2013 | Burlison et al. |
| 8,524,712 | B2 | 9/2013 | Lee et al. |
| 8,628,752 | B2 | 1/2014 | Zhou et al. |
| 8,629,285 | B2 | 1/2014 | Ying et al. |
| 8,648,071 | B2 | 2/2014 | Burlison et al. |
| 8,648,104 | B2 | 2/2014 | Du et al. |
| 2008/0027047 | A1 | 1/2008 | Ying |
| 2008/0125587 | A1 | 5/2008 | Chimmanamada et al. |
| 2010/0069442 | A1 | 3/2010 | Ying et al. |
| 2010/0249185 | A1 | 9/2010 | Du et al. |
| 2010/0280032 | A1 | 11/2010 | Zhou et al. |
| 2011/0009397 | A1 | 1/2011 | Ying et al. |
| 2011/0046125 | A1 | 2/2011 | Ying |
| 2011/0152310 | A1 | 6/2011 | Burlison et al. |
| 2011/0195094 | A1 | 8/2011 | Ying et al. |
| 2011/0224206 | A1 | 9/2011 | Ying et al. |
| 2011/0301212 | A1 | 12/2011 | Du et al. |
| 2011/0319404 | A1 | 12/2011 | Foley |
| 2012/0064175 | A1 | 3/2012 | Vukovic et al. |

(Continued)

FOREIGN PATENT DOCUMENTS

| WO | 2007139951 A2 | 12/2007 |
| WO | 2008/153730 A2 | 12/2008 |
| WO | 2009102446 A2 | 8/2009 |
| WO | 2011049946 A1 | 4/2011 |

OTHER PUBLICATIONS

Geoffrey Shapiro: "Phase II study of the Hsp90 inhibitor ganetespib as monotherapy in patients with advanced NSCLC", Internet-U-Tube, Jun. 2011, Retrieved from the Internet: URL:http//www.youtube.com/watch?v=UX8fEZbF1bk.

Nwizu T et al: "Crizotinib ALK/Met inhibitor Oncolytic", Drugs of the Future, Prous Science, ES, vol. 36, No. 2, Feb. 1, 2011, pp. 91-99.

Reichert et al: "Ganetespib: An effective strategy to overcome crizotinib resistance in ALK-driven cancers", Internet, Apr. 21, 2012, Retrieved from the Internet: URL:http://www.syntapharma.com/Documents/Ganetespib_ALK_Euro IASLC_2012_Poster.pdf [retrieved on Sep. 14, 2012].

Katayama et al: "Therapeutic strategies to overcome crizotinib resistance in non-small cell lung cancers harboring the fusion oncogene EML4-ALK", Proceedings of the National Academy of Sciences, National Academy of Sciences, US, vol. 1 08, No. 18, May 3, 2011, pp. 7535-7540.

(Continued)

*Primary Examiner* — Raymond Henley, III
(74) *Attorney, Agent, or Firm* — McCarter & English, LLP; Steven G. Davis

(57) ABSTRACT

Methods of treating cancer with a compound of formulae (I) or (1a) are disclosed. Also provided are methods of treating a cancer with a mutation in ALK or a c-MET mutation with a compound of formulae (I) or (1a). Further provided are methods of treating non-small cell lung cancer with a mutation in ALK with a compound of formulae (I) or (1a); a tautomer, or a pharmaceutically acceptable salt thereof, wherein the variables structural formulae are defined herein.

23 Claims, 18 Drawing Sheets

(56) References Cited

U.S. PATENT DOCUMENTS

| | | |
|---|---|---|
| 2012/0122869 A1 | 5/2012 | Ying et al. |
| 2012/0245186 A1 | 9/2012 | Blackman et al. |
| 2012/0330009 A1 | 12/2012 | Ying et al. |
| 2013/0072461 A1 | 3/2013 | Chimmanamada et al. |
| 2013/0072489 A1 | 3/2013 | Chimmanamada et al. |
| 2013/0072536 A1 | 3/2013 | Ying et al. |
| 2013/0150385 A1 | 6/2013 | Blackman et al. |
| 2013/0156755 A1 | 6/2013 | Blackman et al. |
| 2013/0171105 A1 | 7/2013 | Blackman et al. |
| 2013/0172333 A1 | 7/2013 | Jain et al. |
| 2013/0225870 A1 | 8/2013 | Lee et al. |
| 2013/0261164 A1 | 10/2013 | Chimmanamada et al. |
| 2013/0296378 A1 | 11/2013 | Sun et al. |
| 2013/0303493 A1 | 11/2013 | Burlison et al. |
| 2013/0331357 A1 | 12/2013 | Proia et al. |
| 2013/0338155 A1 | 12/2013 | Ying |
| 2013/0345219 A1 | 12/2013 | Lee et al. |
| 2014/0005145 A1 | 1/2014 | Proia |
| 2014/0045908 A1 | 2/2014 | Blackman et al. |
| 2014/0051664 A1 | 2/2014 | Foley et al. |
| 2014/0051665 A1 | 2/2014 | Proia et al. |

OTHER PUBLICATIONS

Ying, et al:, Blood, vol. 116, No. 21, Nov. 2010, p. 1194, 52ND Annual Meeting of the American-Society-Of-Hematology (ASH); Orlando, FL, USA; Dec. 4-7, 2010.

International Search Report and Written Opinion issued in PCT/US2012/045978, (date not provided).

TREATING CANCER WITH HSP90 INHIBITORY COMPOUNDS

CROSS-REFERENCE TO RELATED PATENTS

This application is the national stage of International Application No. PCT/US2012/045978, filed on Jul. 9, 2012, which claims priority to U.S. Provisional Patent Application Nos. 61/505,322, filed on Jul. 7, 2011; 61/549,941, filed on Oct. 21, 2011; and 61/623,762, filed on Apr. 13, 2012. The contents of each of these applications are incorporated herein by reference in their entireties.

BACKGROUND OF THE INVENTION

Although tremendous advances have been made in elucidating the genomic abnormalities that cause malignant cancer cells, currently available chemotherapy remains unsatisfactory, and the prognosis for the majority of patients diagnosed with cancer remains dismal. Most chemotherapeutic agents act on a specific molecular target thought to be involved in the development of the malignant phenotype. However, a complex network of signaling pathways regulate cell proliferation and the majority of malignant cancers are facilitated by multiple genetic abnormalities in these pathways. Therefore, it is less likely that a therapeutic agent that acts on one molecular target will be fully effective in curing a patient who has cancer.

Heat shock proteins (HSPs) are a class of chaperone proteins that are up-regulated in response to elevated temperature and other environmental stresses, such as ultraviolet light, nutrient deprivation and oxygen deprivation. HSPs act as chaperones to other cellular proteins (called client proteins), facilitate their proper folding and repair, and aid in the refolding of misfolded client proteins. There are several known families of HSPs, each having its own set of client proteins. The Hsp90 family is one of the most abundant HSP families, accounting for about 1-2% of proteins in a cell that is not under stress, and increasing to about 4-6% in a cell under stress. Inhibition of Hsp90 results in the degradation of its client proteins via the ubiquitin proteasome pathway. Unlike other chaperone proteins, the client proteins of Hsp90 are mostly protein kinases or transcription factors involved in signal transduction, and a number of its client proteins have been shown to be involved in the progression of cancer.

SUMMARY OF THE INVENTION

It is now found that Hsp90 inhibitors, such as certain triazolone Hsp90 inhibitors described herein, are particularly effective in treating cancer with a mutation in ALK, particularly in treating non-small cell lung cancer (NSCLC) with ALK mutations including EML4-ALK or NPM-ALK translocations. Also, these Hsp90 inhibitors have been found to be particularly effective in treating a cancer with a mutation in ALK wherein the cancer has previously been treated with an ALK inhibitor and is no longer responsive to the treatment; in particular, where the cancer has previously been treated with crizotinib and is no longer responsive to the treatment (or, resistant to further crizotinib treatment). Certain triazolone Hsp90 inhibitors such as ganetespib are found to be effective in treating non-small cell lung cancer wherein the NSCLC has been previously treated with crizotinib and is resistant to further crizotinib treatment.

The methods described herein includes utilizing Hsp90 inhibitors according to formulae (I) or (Ia), or compounds in Tables 1 or 2, for treating cancer with a mutation in ALK. In one aspect, a subject with cancer with a mutation in ALK is identified and an effective amount of at least one of these Hsp90 inhibitors is administered to the subject. In another aspect, a subject is administered an effective amount of at least one of these Hsp90 inhibitors, wherein the subject has cancer with a mutation in ALK. The Hsp90 inhibitor may be ganetespib. In an embodiment, ganetespib is administered as a single agent. In another embodiment, ganetespib is administered in combination with one or more additional therapeutic agents. In an embodiment, the additional therapeutic agent is crizotinib. In an embodiment, a combination of ganetespib and crizotinib is also used for treating a subject with cancer having a c-MET mutation.

In embodiments, the cancer is NSCLC with a mutation in ALK; a NSCLC with an ALK-EML4 translocation; NSCLC with an NPM-ALK translocation; NSCLC with a KIF5B-ALK fusion; NSCLC with a TFG-ALK fusion; diffuse large B-cell lymphoma (DLBCL) with mutation in ALK; DLBCL with a CLTC-ALK fusion; anaplastic large cell lymphoma (ALCL) with a mutation in ALK; ALCL with a mutation in NPM-ALK or MSN-ALK; neuroblastoma (NBL) with a mutation in ALK; NBL with a mutation in F1174L or R1275Q; inflammatory myofibroblastic tumor (IMT) with a mutation in ALK; or IMT with a mutation in TPM3-ALK, TPM4-ALK, CLTC-ALK, or RanBP2-ALK.

In an embodiment, the cancer expresses the CLTC-ALK mutation; the EML4-ALK or TFG-ALK mutations; NPM-ALK or MSN-ALK mutations; the TPM4-ALK mutation; TPM3-ALK, TPM4-ALK, CLTC-ALK, or RanBP2-ALK mutations; the KIF5B-ALK mutation; or F1174L or R1275Q point mutations.

Another embodiment includes methods utilizing these Hsp90 inhibitory compounds for treating cancer that has been previously treated with an ALK inhibitor and is no longer responsive to the treatment. These methods include administering to a subject an effective amount of at least one of these Hsp90 inhibitory compounds (such as ganetespib), wherein the subject has previously been treated with an ALK inhibitor and is no longer responsive to the earlier treatment. In an embodiment, the cancer subject has been previously treated with crizotinib and is no longer responsive to crizotinib treatment. In an embodiment, the subject has NSCLC, has been previously treated with crizotinib, and is no longer responsive to the treatment.

DETAILED DESCRIPTION OF THE INVENTION

Definitions

Figure 1:
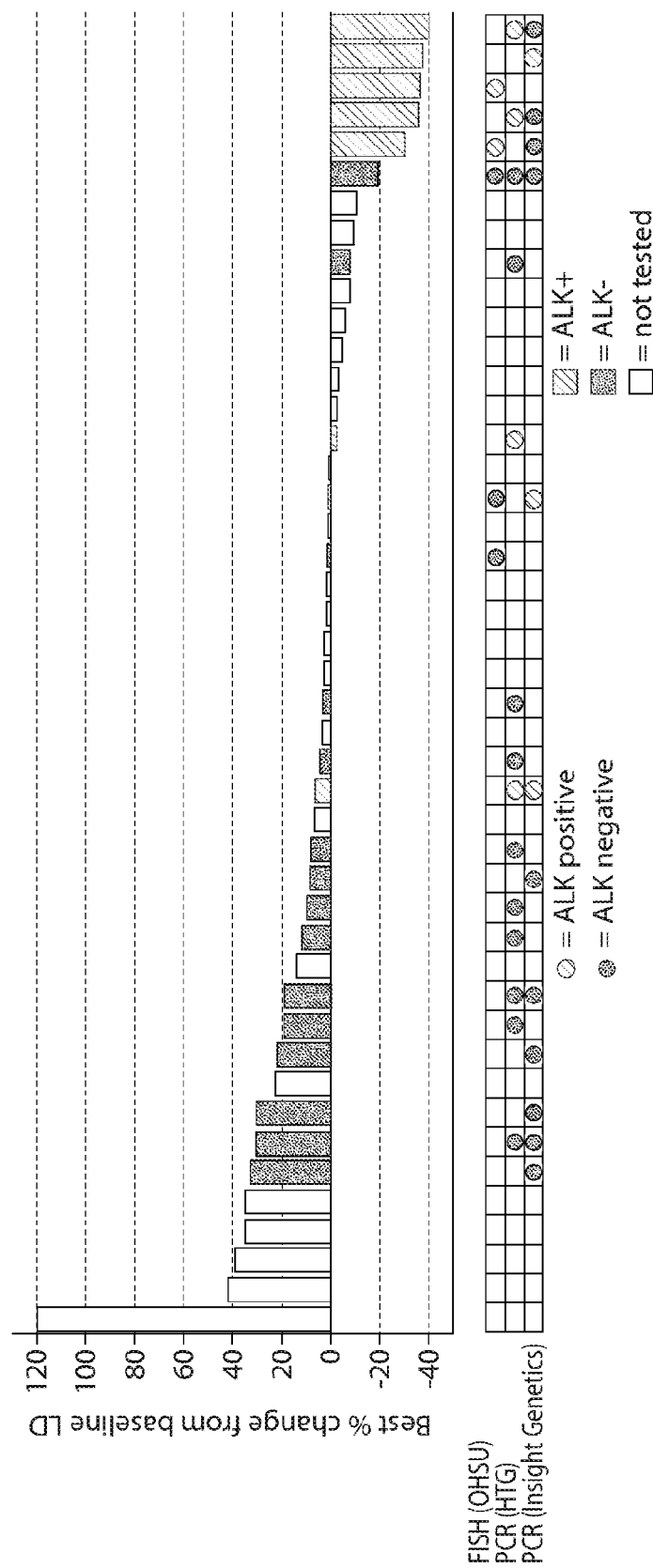
FIG. 1 is a waterfall diagram showing the best percentage changes in size of target lesions responses according to ALK status after treatment with ganetespib. The y axis represents the percentage tumor volume change from baseline. For each patient (each bar) the percentage change in measurable tumor at best response was displayed by the genotype of the patient, i.e., ALK status. A subject was considered to be ALK+ if a mutation in ALK was detected using any of the methods.

Unless otherwise specified, the below terms used herein are defined as follows:

As used herein, the term "alkyl" means a saturated or unsaturated, straight chain or branched, non-cyclic hydrocarbon having from 1 to 10 carbon atoms. Representative straight chain alkyls include methyl, ethyl, n-propyl, n-butyl, n-pentyl, n-hexyl, n-heptyl, n-octyl, n-nonyl and n-decyl; while representative branched alkyls include isopropyl, sec-butyl, isobutyl, tert-butyl, isopentyl, 2-methylbutyl, 3-methylbutyl, 2-methylpentyl, 3-methylpentyl, 4-methylpentyl, 2-methylhexyl, 3-methylhexyl, 4-methylhexyl, 5-methylhexyl, 2,3-dimethylbutyl, 2,3-dimethylpentyl, 2,4-dimethylpentyl, 2,3-dimethylhexyl, 2,4-dimethylhexyl, 2,5-dimethylhexyl, 2,2-dimethylpentyl, 2,2-dimethylhexyl, 3,3-dimtheylpentyl, 3,3-dimethylhexyl, 4,4-dimethylhexyl, 2-ethylpentyl, 3-ethylpentyl, 2-ethylhexyl, 3-ethylhexyl, 4-ethylhexyl, 2-methyl-2-ethylpentyl, 2-methyl-3-ethylpentyl, 2-methyl-4-ethylpentyl, 2-methyl-2-ethylhexyl, 2-methyl-3-ethylhexyl, 2-methyl-4-ethylhexyl, 2,2-diethylpentyl, 3,3-diethylhexyl, 2,2-diethylhexyl, 3,3-diethylhexyl, and the like. The term "(C$_1$-C$_6$)alkyl" means a saturated, straight chain or branched, non-cyclic hydrocarbon having from 1 to 6 carbon atoms. Alkyl groups included in compounds described herein may be optionally substituted with one or more substituents. Examples of unsaturated alkyls include vinyl, allyl, 1-butenyl, 2-butenyl, isobutylenyl, 1-pentenyl, 2-pentenyl, 3-methyl-1-butenyl, 2-methyl-2-butenyl, 2,3-dimethyl-2-butenyl, 1-hexenyl, 2-hexenyl, 3-hexenyl, 1-heptenyl, 2-heptenyl, 3-heptenyl, 1-octenyl, 2-octenyl, 3-octenyl, 1-nonenyl, 2-nonenyl, 3-nonenyl, 1-decenyl, 2-decenyl, 3-decenyl, acetylenyl, propynyl, 1-butynyl, 2-butynyl, 1-pentynyl, 2-pentynyl, 3-methyl-1-butynyl, 4-pentynyl, 1-hexynyl, 2-hexynyl, 5-hexynyl, 1-heptynyl, 2-heptynyl, 6-heptynyl, 1-octynyl, 2-octynyl, 7-octynyl, 1-nonynyl, 2-nonynyl, 8-nonynyl, 1-decynyl, 2-decynyl, 9-decynyl, and the like. Alkyl groups included in compounds described herein may be optionally substituted with one or more substituents.

As used herein, the term "cycloalkyl" means a saturated or unsaturated, mono- or polycyclic, non-aromatic hydrocarbon having from 3 to 20 carbon atoms. Representative cycloalkyls include cyclopropyl, 1-methylcyclopropyl, cyclobutyl, cyclopentyl, cyclohexyl, cycloheptyl, cyclooctyl, cyclononyl, cyclodecyl, octahydropentalenyl, cyclohexenyl, cyclooctenyl, cyclohexynyl, and the like. Cycloalkyl groups included in the compounds described herein may be optionally substituted with one or more substituents.

As used herein, the term "alkylene" refers to an alkyl group that has two points of attachment. The term "$(C_1-C_6)$alkylene" refers to an alkylene group that has from one to six carbon atoms. Straight chain $(C_1-C_6)$alkylene groups are preferred. Non-limiting examples of alkylene groups include methylene (—CH$_2$—), ethylene (—CH$_2$CH$_2$—), n-propylene (—CH$_2$CH$_2$CH$_2$—), isopropylene (—CH$_2$CH(CH$_3$)—), and the like. Alkylene groups may be saturated or unsaturated, and may be optionally substituted with one or more substituents.

As used herein, the term "lower" refers to a group having up to four atoms. For example, a "lower alkyl" refers to an alkyl radical having from 1 to 4 carbon atoms, "lower alkoxy" refers to "—O—$(C_1-C_4)$alkyl.

As used herein, the term "haloalkyl" means an alkyl group, in which one or more, including all, the hydrogen radicals are replaced by a halo group(s), wherein each halo group is independently selected from —F, —Cl, —Br, and —I. The term "halomethyl" means a methyl in which one to three hydrogen radical(s) have been replaced by a halo group. Representative haloalkyl groups include trifluoromethyl, bromomethyl, 1,2-dichloroethyl, 4-iodobutyl, 2-fluoropentyl, and the like.

As used herein, an "alkoxy" is an alkyl group which is attached to another moiety via an oxygen linker. Alkoxy groups included in compounds described herein may be optionally substituted with one or more substituents.

As used herein, a "haloalkoxy" is a haloalkyl group which is attached to another moiety via an oxygen linker.

As used herein, the term an "aromatic ring" or "aryl" means a mono- or polycyclic hydrocarbon, containing from 6 to 15 carbon atoms, in which at least one ring is aromatic. Examples of suitable aryl groups include phenyl, tolyl, anthracenyl, fluorenyl, indenyl, azulenyl, and naphthyl, as well as benzo-fused carbocyclic moieties such as 5,6,7,8-tetrahydronaphthyl. Aryl groups included in compounds described herein may be optionally substituted with one or more substituents. In one embodiment, the aryl group is a monocyclic ring, wherein the ring comprises 6 carbon atoms, referred to herein as "$(C_6)$aryl."

As used herein, the term "aralkyl" means an aryl group that is attached to another group by a $(C_1-C_6)$alkylene group. Representative aralkyl groups include benzyl, 2-phenylethyl, naphth-3-yl-methyl and the like. Aralkyl groups included in compounds described herein may be optionally substituted with one or more substituents.

As used herein, the term "heterocyclyl" means a monocyclic or a polycyclic, saturated or unsaturated, non-aromatic ring or ring system which typically contains 5- to 20-members and at least one heteroatom. A heterocyclic ring system can contain saturated ring(s) or unsaturated non-aromatic ring(s), or a mixture thereof. A 3- to 10-membered heterocycle can contain up to 5 heteroatoms, and a 7- to 20-membered heterocycle can contain up to 7 heteroatoms. Typically, a heterocycle has at least one carbon atom ring member. Each heteroatom is independently selected from nitrogen, which can be oxidized (e.g., N(O)) or quaternized, oxygen and sulfur, including sulfoxide and sulfone. The heterocycle may be attached via any heteroatom or carbon atom. Representative heterocycles include morpholinyl, thiomorpholinyl, pyrrolidinonyl, pyrrolidinyl, piperidinyl, piperazinyl, hydantoinyl, valerolactamyl, oxiranyl, oxetanyl, tetrahydrofuranyl, tetrahydropyranyl, tetrahydropyrindinyl, tetrahydropyrimidinyl, tetrahydrothiophenyl, tetrahydrothiopyranyl, and the like. A heteroatom may be substituted with a protecting group known to those of ordinary skill in the art, for example, a nitrogen atom may be substituted with a tert-butoxycarbonyl group. Furthermore, the heterocyclyl included in compounds described herein may be optionally substituted with one or more substituents. Only stable isomers of such substituted heterocyclic groups are contemplated in this definition.

As used herein, the term "heteroaryl", or like terms, means a monocyclic or a polycyclic, unsaturated radical containing at least one heteroatom, in which at least one ring is aromatic. Polycyclic heteroaryl rings must contain at least one heteroatom, but not all rings of a polycyclic heteroaryl moiety must contain heteroatoms. Each heteroatom is independently selected from nitrogen, which can be oxidized (e.g., N(O)) or quaternized, oxygen and sulfur, including sulfoxide and sulfone. Representative heteroaryl groups include pyridyl, 1-oxo-pyridyl, furanyl, benzo[1,3]dioxolyl, benzo[1,4]dioxinyl, thienyl, pyrrolyl, oxazolyl, imidazolyl, thiazolyl, an isoxazolyl, quinolinyl, pyrazolyl, isothiazolyl, pyridazinyl, pyrimidinyl, pyrazinyl, a triazinyl, triazolyl, thiadiazolyl, isoquinolinyl, indazolyl, benzoxazolyl, benzofuryl, indolizinyl, imidazopyridyl, tetrazolyl, benzimidazolyl, benzothiazolyl, benzothiadiazolyl, benzoxadiazolyl, indolyl, tetrahydroindolyl, azaindolyl, imidazopyridyl, quinazolinyl, purinyl, pyrrolo[2,3]pyrimidinyl, pyrazolo[3,4]pyrimidinyl, imidazo[1,2-a]pyridyl, and benzothienyl. In one embodiment, the heteroaromatic ring is selected from 5-8 membered monocyclic heteroaryl rings. The point of attachment of a heteroaromatic or heteroaryl ring may be at either a carbon atom or a heteroatom. Heteroaryl groups included in compounds described herein may be optionally substituted with one or more substituents. As used herein, the term "$(C_5)$heteroaryl" means an heteroaromatic ring of 5 members, wherein at least one carbon atom of the ring is replaced with a heteroatom, such as oxygen, sulfur or nitrogen. Representative $(C_5)$heteroaryls include furanyl, thienyl, pyrrolyl, oxazolyl, imidazolyl, thiazolyl, isoxazolyl, pyrazolyl, isothiazolyl, pyrazinyl, triazolyl, thiadiazolyl, and the like. As used herein, the term "$(C_6)$heteroaryl" means an aromatic heterocyclic ring of 6 members, wherein at least one carbon atom of the ring is replaced with a heteroatom such as oxygen, nitrogen or sulfur. Representative $(C_6)$heteroaryls include pyridyl, pyridazinyl, pyrazinyl, triazinyl, tetrazinyl, and the like.

As used herein, the term "heteroaralkyl" means a heteroaryl group that is attached to another group by a $(C_1-C_6)$ alkylene. Representative heteroaralkyls include 2-(pyridin-4-yl)-propyl, 2-(thien-3-yl)-ethyl, imidazol-4-yl-methyl, and the like. Heteroaralkyl groups included in compounds described herein may be optionally substituted with one or more substituents.

As used herein, the term "halogen" or "halo" means —F, —Cl, —Br or —I.

Suitable substituents for an alkyl, alkylene, alkenyl, alkynyl, cycloalkyl, cycloalkenyl, heterocyclyl, aryl, aralkyl, heteroaryl, and heteroaralkyl groups include are those substituents which form a stable compound described herein without significantly adversely affecting the reactivity or biological activity of the compound described herein. Examples of substituents for an alkyl, alkylene, alkenyl, alkynyl, cycloalkyl, cycloalkenyl, heterocyclyl, aryl, aralkyl, heteroaryl, and heteroaralkyl include an alkyl, alkenyl, alkynyl, cycloalkyl, cycloalkenyl, heterocyclyl, aryl, heteroaryl, aralkyl, heteraralkyl, heteroalkyl, alkoxy, (each of which can be optionally and independently substituted), —C(O)NR$^{28}$R$^{29}$, —C(S)NR$^{28}$R$^{29}$, —C(NR$^{32}$)NR$^{28}$R$^{29}$, —NR$^{33}$C(O)R$^{31}$, —NR$^{33}$C(S)R$^{31}$, —NR$^{33}$C(NR$^{32}$)R$^{31}$, halo, —OR", cyano, nitro, —C(O)R$^{33}$, —C(S)R$^{33}$, —C(NR$^{32}$)R$^{33}$, —NR$^{28}$R$^{29}$, —C(O)OR$^{33}$, —C(S)OR", —C(NR$^{32}$)OR$^{33}$, —OC(O)R$^{33}$, —OC(S)R$^{33}$, —OC(NR$^{32}$)R$^{33}$, —NR$^{30}$C(O)NR$^{28}$R$^{29}$, —NR$^{33}$C(S)NR$^{28}$R$^{29}$, —NR$^{33}$C(NR$^{32}$)NR$^{28}$R$^{29}$, —OC(O)NR$^{28}$R$^{29}$, —OC(S)NR$^{28}$R$^{29}$, —OC(NR$^{32}$)NR$^{28}$R$^{29}$, —NR$^{33}$C(O)OR$^{31}$, —NR$^{33}$C(S)OR$^{31}$, —NR$^{33}$C(NR$^{32}$)OR$^{31}$, —S(O)$_k$R$^{33}$, —OS(O)$_k$R$^{33}$, —NR$^{33}$S(O)$_k$R$^{33}$, —S(O)$_k$NR$^{28}$R$^{29}$, —OS(O)$_k$NR$^{28}$R$^{29}$, —NR$^{33}$S(O)$_k$NR$^{28}$R$^{29}$, guanidino, —C(O)SR$^{31}$, —C(S)SR$^{31}$, —C(NR$^{32}$)SR$^{31}$, —OC(O)SR$^{31}$, —OC(S)SR$^{31}$, —OC(NR$^{32}$)SR$^{31}$, —SC(O)R$^{33}$, —SC(O)OR$^{31}$, —SC(NR$^{32}$)OR$^{31}$, —SC(S)R$^{33}$—SC(S)OR$^{31}$, —SC(O)NR$^{28}$R$^{29}$, —SC(NR$^{32}$)NR$^{28}$R$^{29}$, —SC(S)NR$^{28}$R$^{29}$, —SC(NR$^{32}$)R$^{33}$, —OS(O)$_k$OR$^{31}$, —S(O)$_k$OR$^{31}$, —NR$^{30}$S(O)$_k$OR$^{31}$, —SS(O)$_k$R$^{33}$, —SS(O)$_k$OR$^{31}$, —SS(O)$_k$NR$^{28}$R$^{29}$, —OP(O)(OR$^{31}$)$_2$, or —SP(O)(OR$^{31}$)$_2$. In addition, any saturated portion of an alkyl, cycloalkyl, alkylene, heterocyclyl, alkenyl, cycloalkenyl, alkynyl, aralkyl and heteroaralkyl groups, may also be substituted with =O, =S, or =N—R$^{32}$. Each R$^{28}$ and R$^{29}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, or heteroalkyl represented by R$^{28}$ or R$^{29}$ is optionally and independently substituted. Each R$^{30}$, R$^{31}$ and R$^{33}$ is independently H, alkyl, alkenyl, alkynyl, cycloalkyl, cycloalkenyl, heterocyclyl, aryl, heteroaryl, aralkyl, or heteraralkyl, wherein each alkyl, alkenyl, alkynyl, cycloalkyl, cycloalkenyl, heterocyclyl, aryl, heteroaryl, aralkyl, and heteraralkyl represented by R$^{30}$ or R$^{31}$ or R$^{33}$ is optionally and independently unsubstituted. Each R$^{32}$ is independently H, alkyl, alkenyl, alkynyl, cycloalkyl, cycloalkenyl, heterocyclyl, aryl, heteroaryl, aralkyl, heteraralkyl, —C(O)R$^{33}$, —C(O)NR$^{28}$R$^{29}$, —S(O)$_k$R$^{33}$, or —S(O)$_k$NR$^{28}$R$^{29}$, wherein each alkyl, alkenyl, alkynyl, cycloalkyl, cycloalkenyl, heterocyclyl, aryl, heteroaryl, aralkyl and heteraralkyl represented by R$^{32}$ is optionally and independently substituted. The variable k is 0, 1 or 2. In some embodiments, suitable substituents include C1-C4 alkyl, C1-C4 haloalkyl, C1-C4 alkoxy, C1-C4 haloalkoxy, C1-C4 hydroxyalkyl, halo, or hydroxyl.

When a heterocyclyl, heteroaryl or heteroaralkyl group contains a nitrogen atom, it may be substituted or unsubstituted. When a nitrogen atom in the aromatic ring of a heteroaryl group has a substituent, the nitrogen may be oxidized or a quaternary nitrogen.

Unless indicated otherwise, the compounds described herein containing reactive functional groups, such as, for example, carboxy, hydroxy, thiol and amino moieties, also include corresponding protected derivatives thereof. "Protected derivatives" are those compounds in which a reactive site or sites are blocked with one or more protecting groups. Examples of suitable protecting groups for hydroxyl groups include benzyl, methoxymethyl, allyl, trimethylsilyl, tert-butyldimethylsilyl, acetate, and the like. Examples of suitable amine protecting groups include benzyloxycarbonyl, tert-butoxycarbonyl, tert-butyl, benzyl and fluorenylmethyloxy-carbonyl (Fmoc). Examples of suitable thiol protecting groups include benzyl, tert-butyl, acetyl, methoxymethyl and the like. Other suitable protecting groups are well known to those of ordinary skill in the art and include those found in T. W. GREENE, PROTECTING GROUPS IN ORGANIC SYNTHESIS, (John Wiley & Sons, Inc., 1981).

As used herein, the term "compound(s) described herein" or similar terms refers to a compound of formulae (I), or (Ia) or a compound in Tables 1 or 2 or a tautomer or pharmaceutically acceptable salt thereof. Also included in the scope of the embodiments are a solvate, clathrate, hydrate, polymorph, prodrug, or protected derivative of a compound of formulae (I), or (Ia), or a compound in Tables 1 or 2.

The compounds described herein may contain one or more chiral centers and/or double bonds and, therefore, exist as stereoisomers, such as double-bond isomers (i.e., geometric isomers), enantiomers or diastereomers. Each chemical structure shown herein, including the compounds described herein, encompass all of the corresponding enantiomers, diastereomers and geometric isomers, that is, both the stereochemically pure form (e.g., geometrically pure, enantiomerically pure, or diastereomerically pure) and isomeric mixtures (e.g., enantiomeric, diastereomeric and geometric isomeric mixtures). In some cases, one enantiomer, diastereomer or geometric isomer will possess superior activity or an improved toxicity or kinetic profile compared to other isomers. In those cases, such enantiomers, diastereomers and geometric isomers of compounds described herein are preferred.

Only those choices and combinations of substituents that result in a stable structure are contemplated. Such choices and combinations will be apparent to those of ordinary skill in the art and may be determined without undue experimentation.

When a disclosed compound is named or depicted by structure, it is to be understood that solvates (e.g., hydrates) of the compound or a pharmaceutically acceptable salt thereof is also included. "Solvates" refer to crystalline forms wherein solvent molecules are incorporated into the crystal lattice during crystallization. Solvates may include water or non-aqueous solvents such as ethanol, isopropanol, DMSO, acetic acid, ethanolamine and ethyl acetate. When water is the solvent molecule incorporated into the crystal lattice of a solvate, it is typically referred to as a "hydrate" e.g., hemihydrate, monohydrate, dihydrate, trihydrate, and tetrahydrate. Hydrates include stoichiometric hydrates as well as compositions containing variable amounts of water. "Pharmaceutically acceptable solvate" refers to a solvate formed from the association of one or more pharmaceutically acceptable solvent molecules to a compound of formulae (I) or (Ia) or a compound in Tables 1 or 2.

When a disclosed compound is named or depicted by structure, it is to be understood that the compound, including solvates thereof, may exist in crystalline forms, non-crystalline forms or a mixture thereof. The compounds or solvates may also exhibit polymorphism (i.e., the capacity to occur in different crystalline forms). These different crystalline forms are typically known as "polymorphs." It is to be understood that when named or depicted by structure, the disclosed compounds and solvates (e.g., hydrates) also include all polymorphs thereof. Polymorphs have the same chemical composition but differ in packing, geometrical arrangement and other descriptive properties of the crystalline solid state. Polymorphs, therefore, may have different physical properties such as shape, density, hardness, deformability, stability and dissolution properties. Polymorphs typically exhibit different melting points, IR spectra and X-ray powder diffraction patterns, which may be used for identification. One of ordinary skill in the art will appreciate that different polymorphs may be produced, for example, by changing or adjusting the conditions used in crystallizing the compound. For example, changes in temperature, pressure or solvent may result in different polymorphs. In addition, one polymorph may spontaneously convert to another polymorph under certain conditions.

When a disclosed compound is named or depicted by structure, it is to be understood that clathrates ("inclusion compounds") of the compound or its pharmaceutically acceptable salt, solvate or polymorph, are also included. "Clathrate" means a compound described herein, or a salt thereof, in the form of a crystal lattice that contains spaces (e.g., channels) that have a guest molecule trapped within (e.g., a solvent or water).

As used herein, and unless otherwise indicated, the term "prodrug" means a derivative of a compound that can hydrolyze, oxidize, or otherwise react under biological conditions (in vitro or in vivo) to provide a compound described herein. Prodrugs may become active upon such reaction under biological conditions, or they may have activity in their unreacted forms. Examples of prodrugs contemplated herein include analogs or derivatives of compounds of formulae (I) or (Ia) or a compound in Tables 1 or 2 that comprise biohydrolyzable moieties such as biohydrolyzable amides, biohydrolyzable esters, biohydrolyzable carbamates, biohydrolyzable carbonates, biohydrolyzable ureides and phosphate analogues. Prodrugs can be prepared using well-known methods, such as those described by BURGER'S MEDICINAL CHEMISTRY AND DRUG DISCOVERY, (Manfred E. Wolff Ed., 5th ed. (1995)) 172-178, 949-982.

The compounds described herein are defined by their chemical structures and/or chemical names. Where a compound is referred to by both a chemical structure and a chemical name, and the chemical structure and the chemical name conflict, the chemical structure is determinative of the compound's identity.

As used herein, the terms "subject", "patient" and "mammal" are used interchangeably. The terms "subject" and "patient" refer to an animal (e.g., a bird such as a chicken, quail or turkey, or a mammal), preferably a mammal including a non-primate (e.g., a cow, pig, horse, sheep, rabbit, guinea pig, rat, cat, dog, and mouse) and a primate (e.g., a monkey, chimpanzee and a human), and more preferably a human. In one embodiment, the subject is a non-human animal such as a farm animal (e.g., a horse, cow, pig or sheep), or a pet (e.g., a dog, cat, guinea pig or rabbit). In another embodiment, the subject is a human.

The terms "cancer" or "tumor" are well known in the art and refer to the presence, e.g., in a subject, of cells possessing characteristics typical of cancer-causing cells, such as uncontrolled proliferation, immortality, metastatic potential, rapid growth and proliferation rate, decreased cell death/apoptosis, and certain characteristic morphological features.

"Solid tumor," as used herein, is understood as any pathogenic tumor that can be palpated or detected using imaging methods as an abnormal growth having three dimensions. A solid tumor is differentiated from a blood tumor such as leukemia. However, cells of a blood tumor are derived from bone marrow, therefore, the tissue producing the cancer cells is a solid tissue that can be hypoxic.

"Tumor tissue" is understood as cells, extracellular matrix, and other naturally occurring components associated with the solid tumor.

As used herein, "Hsp90" includes each member of the family of heat shock proteins having a mass of about 90-kiloDaltons. For example, in humans the highly conserved Hsp90 family includes the cytosolic Hsp90α and Hsp90β isoforms, as well as GRP94, which is found in the endoplasmic reticulum, and HSP75/TRAP1, which is found in the mitochondrial matrix.

The articles "a", "an" and "the" are used herein to refer to one or to more than one (i.e. to at least one) of the grammatical object of the article unless otherwise clearly indicated by contrast. By way of example, "an element" means one element or more than one element.

The term "including" is used herein to mean, and is used interchangeably with, the phrase "including but not limited to".

The term "or" is used herein to mean, and is used interchangeably with, the term "and/or," unless context clearly indicates otherwise.

The term "such as" is used herein to mean, and is used interchangeably, with the phrase "such as but not limited to".

Unless specifically stated or obvious from context, as used herein, the term "about" is understood as within a range of normal tolerance in the art, for example within 2 standard deviations of the mean. About can be understood as within 10%, 9%, 8%, 7%, 6%, 5%, 4%, 3%, 2%, 1%, 0.5%, 0.1%, 0.05%, or 0.01% of the stated value. Unless otherwise clear from context, all numerical values provided herein can be modified by the term about.

The recitation of an embodiment for a variable or aspect herein includes that embodiment as any single embodiment or in combination with any other embodiments or portions thereof.

Any compositions or methods provided herein can be combined with one or more of any of the other compositions and methods provided herein.

Methods of Detection of Mutations

The ALK (anaplastic lymphoma kinase) RTK (receptor tyrosine kinase, Accession No. NP_004295) was originally identified as a member of the insulin receptor subfamily of RTKs that acquires transforming capability when truncated and fused to NPM (nucleophosmin) in the t(2;5) chromosomal rearrangement associated with ALCL (anaplastic large cell lymphoma). To date, many chromosomal rearrangements leading to enhanced ALK activity have been described and are implicated in a number of cancer types. Recent reports of the EML4 (echinoderm microtubule-associated protein like 4)-ALK oncoprotein in NSCLC, together with the identification of activating point mutations in neuroblastoma, have highlighted ALK as a significant player and target for drug development in cancer. Representative ALK abnormalities (or "ALK+") include EML4-ALK fusions, KIF5B-ALK fusions, TGF-ALK fusions, NPM-ALK fusions, and ALK point mutations.

Mutational analysis and expression analysis of ALK are routinely assessed by clinical laboratories using standardized kits and reference levels. Such kits and methods are known in the art.

As used herein, a "subject with a mutation", or "cancer having a mutation" in ALK, c-MET, or other gene associated with cancer, or a "subject with a cancer with a mutation" in ALK, c-MET, or other gene associated with cancer, and the like, are understood as a subject having cancer, wherein the tumor has at least one alteration (e.g., 1, 2, 3, 4, 5, 6, 7, 8, 9, 10, or more) in the indicated gene from the wild-type sequence in the gene and/or transcriptional, translational, and/or splicing control regions of the gene that result in the cell becoming cancerous, e.g., developing characteristics such as uncontrolled proliferation, immortality, metastatic potential, rapid growth and proliferation rate, decreased cell death/apoptosis, and certain characteristic morphological features. Mutations include, for example, insertions, deletions, truncations, point mutations, and translocations. Mutations within a gene product can result in constituent activation of the gene product. Mutations that include alterations in transcriptional, translational, or splicing control regions can result in aberrant expression, typically over-expression, of a wild-type gene product. It is understood that not all gene mutations, even in oncogenes, result in a cell becoming cancerous. Mutations that result in oncogenesis are well known in the art. Methods to test mutations for oncogenic activity are well known in the art.

A mutation can be detected using any of a number of known methods in the art. The specific method to detect the mutation will depend, for example, on the type of mutation to be detected. For example, alterations in nucleic acid sequences can be easily detected using polymerase chain reaction and fluorescence in situ hybridization methods (FISH). Protein expression levels can be detected, for example, using immunohistochemistry. An aberrant expression level of a wild-type protein can be used as a surrogate for detection of a mutation in a transcriptional, translational, and/or splicing control regions of the gene without direct detection of the specific genetic change in the nucleic acid in the subject sample. The specific method of detection of the mutation is not a limitation of the invention. Methods to compare protein expression levels to appropriate controls are well known in the art.

In a preferred embodiment, when multiple tests are used to detect a mutation and one is positive, the mutation is considered to be present. The methods do not require that multiple assays be performed to detect a mutation.

As already presented, the methods and procedures for the detections and/or identifications of ALK or c-MET over-expressions and/or mutations are known in the literature and can be easily carried out by a skilled person. See, e.g., U.S. Pat. No. 7,700,339; U.S. Patent Application Publication No. US2011/0110923; Palmer et al, Biochem. J. (2009), 345-361; Koivunen et al, Clin. Can. Res., 2008, 14, 4275-4283; Anderson, Expert Rev. Mol. Diagn. 11(6), 635-642 (2011); Pinto et al, Cancer Genetics 204 (2011), 439-446; Rekhtman et al; Clin Cancer Res 2012; 18:1167-1176; Massarelli et al, Clin Cancer Res 2007; 13:2890-2896; Lamy et al, Modern Pathology (2011) 24, 1090-1100; Balschun et al, Expert Rev. Mol. Diagn. 11(8), 799-802 (2011); Vakiani et al, J Pathol 2011; 223, 219-229; Okudela et al, Pathology International 2010; 60: 651-660; John et al, Oncogene (2009) 28, S14-S23; Qian et al, CANCER RESEARCH 62, 589-596, 2002; and the references cited in the-above identified references. Thresholds of increased expression that constitute an ALK mutation or a c-MET mutation are well known in the art.

The methods for identification of whether or not a subject who has previously been treated with an ALK inhibitor is responsive or resistant to the continuing ALK inhibitor treatment are generally known to a skilled person, and can be conveniently found in the art. For example, Katayama et al, in the April 2011 issue of Proceedings of the National Academy of Sciences of the United States of America, discussed how to determine resistance to ALK inhibitors, particularly to crizotinib resistance.

As used herein, and in the art, an "ALK+" tumor or cancer is understood as a tumor or cancer that has a mutation such that ALK is overexpressed and/or has an alteration, mutation or rearrangement that causes a cancerous phenotype in the cell.

As used in connection with ALK gene or gene product herein, the terms "alteration", "mutation", or "rearrangement" are all interchangeable, and ALK gene or gene product with an alteration, mutation or rearrangement is different from the wild type ALK gene or gene product.

As used herein, a subject with a "wild-type" ALK or other gene associated with cancer, or a "subject with a cancer with a wild-type" ALK or other gene associated with cancer, and the like, are understood as a subject suffering from cancer, wherein the tumor does not have any significant alterations (i.e., alterations that result in a change of function) in the indicated gene from the native sequence in the gene and/or transcriptional, translational, and/or splicing control regions of the native gene that result in the cell becoming cancerous, e.g., developing characteristics such as uncontrolled proliferation, immortality, metastatic potential, rapid growth and proliferation rate, decreased cell death/apoptosis, and certain characteristic morphological features. As used herein, a "wild-type" gene is expressed at a level that does not result in the cell becoming cancerous.

The term "expression" is used herein to mean the process by which a polypeptide is produced from DNA. The process involves the transcription of the gene into mRNA and the translation of this mRNA into a polypeptide. Depending on the context in which used, "expression" may refer to the production of RNA, or protein, or both.

The terms "level of expression of a gene" or "gene expression level" refer to the level of mRNA, as well as pre-mRNA nascent transcript(s), transcript processing intermediates, mature mRNA(s) and degradation products, or the level of protein, encoded by the gene in the cell.

Mutations and protein expression levels are preferably detected in a subject sample from the cancer tissue or tumor tissue, e.g., cells, extracellular matrix, and other naturally occurring components associated with the tumor. The mutation or expression level can be detected in a biopsy sample or in a surgical sample after resection of the tumor. The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In an embodiment, the sample is removed from the subject. In a particular embodiment, the sample is urine or serum. In an embodiment, the sample comprises cells. In another embodiment, the sample does not comprise cells. In certain embodiments, the sample can be the portion of the subject that is imaged. Samples are typically removed from the subject prior to analysis, however, tumor samples can be analyzed in the subject, for example, using imaging or other detection methods (e.g., using a PET scan, a functional imaging method such as MRI to detect blood flow.)

The following two assays are presented as general information about detection and identification of ALK alterations, mutations or rearrangements in an ALK gene or gene product. These types of assays were also used in the Examples described herein:

The EML4/ALK assay detects eight known fusion variants and other undefined variants, in conjunction with measuring expression of wild type EML4 and ALK 5' and 3'.

Lung cancer is the most common and deadly form of cancer in the USA, with a 5-year survival rate of approximately 15 percent. A subset of NSCLC patients have translocations which fuse the 5' end of the EML4 gene to the 3' end of the ALK gene creating an activated ALK oncogene. The incidence of ALK activation in NSCLC is low (2-7 percent), but it may be as high as 13 percent in patients with adenocarcinoma, no or a light history of smoking, younger age, and WT EGFR and KRAS genes. There are several other adenocarcinomas for which the ALK activation is relevant: breast, bladder, head & neck, and colon. Of particular interest, 5% of primary and metastatic melanoma patients harbor the translocation as well.

The EML4/ALK fusion protein displays constitutive ALK kinase activity, which can be targeted with ALK kinase inhibitors. The presence of an EML4/ALK translocation predicts a favorable response to ALK inhibitor therapy.

The quantitative Nuclease Protection Assay (qNPA™) is a multiplexed, lysis only assay of mRNA (53-58) that can also measure DNA and miRNA. What sets qNPA apart from other assays is that it does not require extraction of the DNA or RNA, but rather uses directly lysed samples. This permits high sample throughput, combined with the simultaneous measurement of DNA, mRNA and miRNA from the same lysate, and if necessary, on the same array.

qNPA also is very precise, with average whole assay CV's from tissues <10%, which means changes <1.2-fold can be detected, $p<0.05$. It is currently available as a low cost array plate-based assay measuring up to 47 genes/well.

Genetics: Multiple inversions on chromosome 2p generate in-frame fusions of the EML4 and ALK genes. While the breakpoints of EML4 can vary (fusion at exons 2, 6, 13, 14, 15, 18, and 20), the breakpoint of ALK occurs consistently at exon 20, 5' of the kinase domain. The majority (~70 percent) of translocations involve EML4 exon 13 (variant 1) or EML4 exon 6a/b (variant 3a/b). Due to close proximity of the EML4 and ALK genes, thus the small inversions, detection of some EML4/ALK variants is challenging with commercially available ALK break-apart FISH probes.

Product Format: The initial product is based upon the qNPA ArrayPlate format, either in 47 or 16 spot format as appropriate and dictated by the number of analytes to be tested with the ALK array.

Components: Kits are all inclusive with step-by-step instructions for ease of use.

Sample Type: Cell Lines, Blood, Purified RNA or FFPE

Intended Uses

The intended use for this product is to detect any of the specified expression wild types and fusion variants of ALK and EML4/ALK.

These are as follows:

| | |
|---|---|
| WT: | ALK - 5' |
| WT: | ALK - 3' |
| Fusion: | EML4/ALK - variant 1 |
| Fusion: | EML4/ALK - variant 2 |
| Fusion: | EML4/ALK - variant 3a |
| Fusion: | EML4/ALK - variant 3b |
| Fusion: | EML4/ALK - variant 4 |
| Fusion: | EML4/ALK - variant 5a |
| Fusion: | EML4/ALK - variant 5b |
| Fusion: | EML4/ALK - variant 6 |
| Fusion: | KIF5B-ALK |
| Fusion: | TFG-ALK |
| WT: | EML4 - 5' |
| WT: | KIF5B - 5' |
| WT: | TFG - 5" |

Insight ALK Screen is an RT-qPCR assay that detects the presence of ALK fusions and upregulation of ALK wild type (which is abnormal in adult tissue outside the central nervous system and can be indicative of ALK-driven disease). The assay uses a three tube reaction series (plus controls) to measure expression of the extracellular segment of ALK (ALK WT), ALK kinase domain expression (ALK Kinase), and expression of an internal reference gene, Cytochrome c oxidase subunit 5B (COX5B). By focusing on relative expression of the ALK gene, Insight ALK Screen can more accurately detect the presence of ALK fusions than a variant-specific PCR approach that targets the 10+ unique 5' gene partners, such as EML4.

Methods and procedures for the detection of wild type ALK and NPM-ALK fusions can be found in U.S. Pat. Nos. 5,529,925 and 5,770,421.

It is understood that diagnosis and treatment of a complex disease such as cancer is not performed by a single individual, test, agent, or intervention. For example, a subject may meet with a primary care physician to express a concern and be referred to an oncologist who will request tests that are designed, carried out, and analyzed by any of a number of individuals, but not limited to, radiologists, radiology technicians, physicists, phlebotomists, pathologists, laboratory technicians, and radiation, clinical, and surgical oncologists. Selection, dosing, and administration of agents to a subject diagnosed with cancer will be performed by any of a number of individuals including, but not limited to, radiologists, radiology technicians, physicists, pathologists, infusion nurses, pharmacists, and radiation, clinical, and surgical oncologists. Therefore, it is understood that within the terms of the invention, identifying a subject as having a mutation in ALK can include any of a number of acts including, but not limited to, performing a test and observing a result that is indicative of a subject having a mutation in ALK; reviewing a test result of a subject and identifying the subject as having a mutation in ALK; reviewing documentation on a subject stating that the subject has a mutation in ALK and identifying the subject as the one discussed in the documentation by confirming the identity of the subject, e.g., by an identification card, hospital bracelet, asking the subject for his/her name and/or other personal information to confirm the subject's identity.

Similarly, administering an agent can be performed by a number of people working in concert. Administering an agent includes, for example, prescribing an agent to be administered to a subject and/or providing instructions, directly or through another, to take a specific agent, either by self-delivery, e.g., as by oral delivery, subcutaneous delivery, intravenous delivery through a central line, etc; or for delivery by a trained professional, e.g., intravenous delivery, intramuscular delivery, intratumoral delivery, etc.

As used herein, "detecting", "detection" and the like are understood that an assay performed for identification of a specific analyte in a sample, e.g., a gene or gene product with a mutation, or the expression level of a gene or gene product in a sample, typically as compared to an appropriate control cell or tissue. The specific method of detection used is not a limitation of the invention. The detection method will typically include comparison to an appropriate control sample.

The term "control sample," as used herein, refers to any clinically relevant comparative sample, including, for example, a sample from a healthy subject not afflicted with cancer, a sample from a subject having a less severe or slower progressing cancer than the subject to be assessed, a sample from a subject having some other type of cancer or disease, a sample from a subject prior to treatment, a sample of non-diseased tissue (e.g., non-tumor tissue), a sample from the same origin and close to the tumor site, and the like. A control sample can be a purified sample, protein, and/or nucleic acid provided with a kit. Such control samples can be diluted, for example, in a dilution series to allow for quantitative measurement of analytes in test samples. A control sample may include a sample derived from one or more subjects. A control sample may also be a sample made at an earlier time point from the subject to be assessed. For example, the control sample could be a sample taken from the subject to be assessed before the onset of the cancer, at an earlier stage of disease, or before the administration of treatment or of a portion of treatment. The control sample may also be a sample from an animal model, or from a tissue or cell lines derived from the animal model, of the cancer. The level of signal detected or protein expression in a control sample that consists of a group of measurements may be determined, e.g., based on any appropriate statistical measure, such as, for example, measures of central tendency including average, median, or modal values.

The term "effective amount" includes an amount of at least one of these Hsp90 inhibitory compounds (such as ganetespib) which is sufficient to treat the cancer, to reduce or ameliorate the severity, duration, or progression of cancer, to retard or halt the advancement of cancer, to cause the regression of cancer, to delay the recurrence, development, onset, or progression of a symptom associated with cancer, or to enhance or improve the therapeutic effect(s) of another therapy. For example, an effective amount can induce, for example, a complete response, a partial response, or stable disease; as determined, for example, using RESIST criteria.

An "effective amount" of a therapeutic agent produces a desired response. Having a positive response to treatment with a therapeutic agent is understood as having a decrease in at least one sign or symptom of a disease or condition (e.g., tumor shrinkage, decrease in tumor burden, inhibition or decrease of metastasis, improving quality of life ("QOL"), delay of time to progression ("TTP"), increase of overall survival ("OS"), etc.), or slowing or stopping of disease progression (e.g., halting tumor growth or metastasis, or slowing the rate of tumor growth or metastasis). It is understood that an "effective amount" need not be curative.

An effective amount of at least one of these Hsp90 inhibitory compounds (such as ganetespib) is understood as an amount of at least one of these Hsp90 inhibitory compounds (such as ganetespib) to improve outcome relative to an appropriate control group, e.g., an untreated group, a group treated with a combination of therapies not including at least one of these Hsp90 inhibitory compounds (such as ganetespib). Methods to select appropriate control groups and perform comparative analyses is within the ability of those of skill in the art.

The precise amount of compound administered to provide an "effective amount" of at least one of these Hsp90 inhibitory compounds (such as ganetespib) to the subject will depend on the mode of administration, the type and severity of the cancer and on the characteristics of the subject, such as general health, age, sex, body weight and tolerance to drugs. The skilled artisan will be able to determine appropriate dosages depending on these and other factors. When administered in combination with other therapeutic agents, e.g., when administered in combination with an anti-cancer agent, an "effective amount" of any additional therapeutic agent(s) will depend on the type of drug used. Suitable dosages are known for approved therapeutic agents and can be adjusted by the skilled artisan according to the condition of the subject, the type of condition(s) being treated and the amount of a compound of the invention being used by following, for example, dosages reported in the literature and recommended in the Physician's Desk Reference (57th ed., 2003).

In an embodiment, the amount of at least one of these Hsp90 inhibitory compounds (such as ganetespib) administered is from about 2 mg/m$^2$ to about 500 mg/m$^2$, for example, from about 100 mg/m$^2$ to about 500 mg/m$^2$, from about 125 mg/m$^2$ to about 500 mg/m$^2$, from about 150 mg/m$^2$ to about 500 mg/m$^2$ or from about 175 mg/m$^2$ to about 500 mg/m$^2$. In an embodiment, the amount of at least one of these Hsp90 inhibitory compounds (such as ganetespib) administered is about 100 mg/m$^2$ to about 300 mg/m$^2$, from about 125 mg/m$^2$ to about 300 mg/m$^2$, from about 150 mg/m$^2$ to about 300 m g/m$^2$ or from about 175 mg/m$^2$ to about 300 mg/m$^2$. In some embodiments, the amount of at least one of these Hsp90 inhibitory compounds (such as ganetespib) administered is about 2 mg/m$^2$, 4 mg/m$^2$, about 7 mg/m$^2$, about 10 mg/m$^2$, about 14 mg/m$^2$, about 19 mg/m$^2$, about 23 mg/m$^2$, about 25 mg/m$^2$, about 33 mg/m$^2$, about 35 mg/m$^2$, about 40 mg/m$^2$, about 48 mg/m$^2$, about 49 mg/m$^2$, about 50 mg/m$^2$, about 65 mg/m$^2$, about 75 mg/m$^2$, about 86 mg/m$^2$, about 100 mg/m$^2$, about 110 mg/m$^2$, about 114 mg/m$^2$, about 120 mg/m$^2$, about 144 mg/m$^2$, about 150 mg/m$^2$, about 173 mg/m$^2$, about 180 mg/m$^2$, about 200 mg/m$^2$, about 216 mg/m$^2$ or about 259 mg/m$^2$.

The language "twice-weekly" includes administration of at least one of these Hsp90 inhibitory compounds (such as ganetespib) two times in about 7 days. For example, the first dose of at least one of these Hsp90 inhibitory compounds (such as ganetespib) is administered on day 1, and the second dose of at least one of these Hsp90 inhibitory compounds (such as ganetespib) may be administered on day 2, day 3, day 4, day 5, day 6 or day 7. In some embodiments, the twice-weekly administration occurs on days 1 and 3 or days 1 and 4.

In some embodiments, at least one of these Hsp90 inhibitory compounds (such as ganetespib) is cyclically administered twice-weekly. For example, at least one of these Hsp90 inhibitory compounds (such as ganetespib) is administered for a first period of time, followed by a "dose-free" period, then administered for a second period of time. The language "dose-free" includes the period of time in between the first dosing period and the second dosing period in which no compound is administered to the subject. A preferred cycle is administering at least one of these Hsp90 inhibitory compounds (such as ganetespib) at a dose described above two times during the week for three consecutive weeks followed by one dose-free week. This cycle is then repeated, as described below.

The language "one cycle" includes the first period of time during which at least one of these Hsp90 inhibitory compounds (such as ganetespib) is administered, followed by a dose-free period of time. The dosing cycle can be repeated and one of skill in the art will be able to determine the appropriate length of time for such a cyclical dosing regimen. In an embodiment, the cycle is repeated at least once. In an embodiment, the cycle is repeated two or more times. In an embodiment, the cycle is repeated 3, 4, 5, 6, 7, 8, 9, 10, 11, 12, 13, 14, 15 or more times, or as many times as medically necessary as determined by one of skill in the art, e.g., as long as the subject exhibits a response with no dose limiting toxicities. In an embodiment, the cycle is repeated until the patient has been determined to be in partial remission (e.g., 50% or greater reduction in the measurable parameters of tumor growth) or complete remission (e.g., absence of cancer). One of skill in the art can determine a patient's remission status using routine methods well known in the art.

As used herein, the term "pharmaceutically acceptable salt" refers to a salt prepared from a compound of formulae (I) or (Ia) or a compound in Tables 1 or 2 having an acidic functional group, such as a carboxylic acid functional group, and a pharmaceutically acceptable inorganic or organic base. Suitable bases include hydroxides of alkali metals such as sodium, potassium, and lithium; hydroxides of alkaline earth metal such as calcium and magnesium; hydroxides of other metals, such as aluminum and zinc; ammonia, and organic amines, such as unsubstituted or hydroxy-substituted mono-, di-, or trialkylamines; dicyclohexylamine; tributyl amine; pyridine; N-methyl,N-ethylamine; diethylamine; triethylamine; mono-, bis-, or tris-(2-hydroxy-lower alkyl amines), such as mono-, bis-, or tris-(2-hydroxyethyl)amine, 2-hydroxy-tert-butylamine, or tris-(hydroxymethyl)methylamine, N,N,-di-lower alkyl-N-(hydroxy lower alkyl)-amines, such as N,N-dimethyl-N-(2-hydroxyethyl)amine, or tri-(2-hydroxyethyl)amine; N-methyl-D-glucamine; and amino acids such as arginine, lysine, and the like. The term "pharmaceutically acceptable salt" also refers to a salt prepared from a compound of formulae (I) or (Ia) or a compound in Tables 1 or 2 having a basic functional group, such as an amine functional group, and a pharmaceutically acceptable inorganic or organic acid. Suitable acids include hydrogen sulfate, citric acid, acetic acid, oxalic acid, hydrochloric acid (HCl), hydrogen bromide (HBr), hydrogen iodide (HI), nitric acid, hydrogen bisulfide, phosphoric acid, isonicotinic acid, oleic acid, tannic acid, pantothenic acid, saccharic acid, lactic acid, salicylic acid, tartaric acid, bitartratic acid, ascorbic acid, succinic acid, maleic acid, besylic acid, fumaric acid, gluconic acid, glucaronic acid, formic acid, benzoic acid, glutamic acid, methanesulfonic acid, ethanesulfonic acid, benzenesulfonic acid, pamoic acid and p-toluenesulfonic acid.

As used herein, the term "in combination" refers to the use of more than one therapeutic agent (e.g., 2, 3, 4, 5, 6, 7, 8, 9, 10, or more). The use of the term "in combination" does not restrict the order in which the therapeutic agents are administered to a subject afflicted with cancer. A first therapeutic agent, such as a compound described herein, can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of a second therapeutic agent or treatment, such as an anti-cancer agent, to a subject with cancer. In certain embodiments, one agent may be administered more frequently than the other agent such that multiple doses of one agent are administered for each dose of the other agent(s). In an embodiment, the Hsp90 inhibitor and the one or more additional therapeutic agents are dosed on independent schedules. In another embodiment, the Hsp90 inhibitor and the one or more additional therapeutic agents are dosed on approximately the same schedule. In another embodiment, the Hsp90 inhibitor and the one or more additional therapeutic agents are dosed concurrently or sequentially on the same day. In another embodiment, the Hsp90 inhibitor and the one or more additional therapeutic agents are dosed sequentially on different days.

In an embodiment, the method comprises administering to the subject with a cancer with a mutation in ALK an effective amount of a combination of at least one of these Hsp90 inhibitory compounds (such as ganetespib), or a tautomer or pharmaceutically acceptable salt thereof, and one or more of BEZ235, AZD6244, AZD8055, SN-38, gemcitabine, camptothecin, docetaxel, cisplatin, oxaliplatin, crizotinib, paclitaxel, trastuzumab, or pemetrexed. In an embodiment, the combination is with BEZ235. In an embodiment, the combination is with AZD6244. In an embodiment, the combination is with AZD8055. In an embodiment, the combination is with SN-38. In an embodiment, the combination is with gemcitabine. In an embodiment, the combination is with camptothecin. In an embodiment, the combination is with docetaxel. In an embodiment, the combination is with cisplatin. In an embodiment, the combination is with oxaliplatin. In an embodiment, the combination is with crizotinib. In an embodiment, the combination is with trastuzumab. In an embodiment, the combination is with pemetrexed.

In an embodiment, at least one of these Hsp90 inhibitory compounds (such as ganetespib) may be administered for treating NSCLC with a mutation in ALK in a subject in combination with one or more additional anti-cancer agents. In an embodiment, the method comprises administering to the subject with NSCLC with a mutation in ALK an effective amount of a combination of at least one of these Hsp90 inhibitory compounds (such as ganetespib), or a tautomer or pharmaceutically acceptable salt thereof, and one or more of BEZ235, AZD6244, AZD8055, SN-38, gemcitabine, camptothecin, docetaxel, cisplatin, oxaliplatin, crizotinib, paclitaxel, trastuzumab, or pemetrexed. In an embodiment, the combination with BEZ235. In an embodiment, the combination is with AZD6244. In an embodiment, the combination is with AZD8055. In an embodiment, the combination is with SN-38. In an embodiment, the combination is with gemcitabine. In an embodiment, the combination is with camptothecin. In an embodiment, the combination is with docetaxel. In an embodiment, the combination is with cisplatin. In an embodiment, the combination is with oxaliplatin. In an embodiment, the combination is with crizotinib. In an embodiment, the combination with trastuzumab. In an embodiment, the combination is with pemetrexed.

In an embodiment, the one or more additional anti-cancer agents include one or more of VEGF inhibitors (e.g., bevacizumab, sunitinib, or sorafenib), EGFR inhibitors (e.g., erlotinib, gefitinib or cetuximab), tyrosine kinase inhibitors (e.g., imatinib), proteosome inhibitors (e.g., bortezomib), taxanes (e.g., paclitaxel and paclitaxel analogues), and ALK inhibitors (e.g., crizotinib). In an embodiment, the additional anti-cancer drug is trastuzumab.

At least one of these Hsp90 inhibitory compounds (such as ganetespib) and optionally, one or more additional anti-cancer agents, can be administered to a subject by routes known to one of skill in the art. Examples of routes of administration include, but are not limited to, parenteral, e.g., intravenous, intradermal, subcutaneous, oral, intranasal (e.g., inhalation), transdermal, topical, transmucosal, and rectal administration. The agents can be administered by different routes of administration.

The triazolone compounds described herein can be formulated into or administered by controlled release means or by delivery devices that are well known to those of ordinary skill in the art. Examples include those described in U.S. Pat. Nos. 3,845,770; 3,916,899; 3,536,809; 3,598,123; and 4,008,719, 5,674,533, 5,059,595, 5,591,767, 5,120,548, 5,073,543, 5,639,476, 5,354,556, and 5,733,566.

At least one of these Hsp90 inhibitory compounds (such as ganetespib), and optionally, one or more additional anti-cancer agents, may be formulated with a pharmaceutically acceptable carrier, diluent, or excipient as a pharmaceutical composition. Pharmaceutical compositions and dosage forms of the invention comprise one or more active ingredients in relative amounts and formulated in such a way that a given pharmaceutical composition or dosage form can be used to treat cancer. Administration in combination does not require co-formulation.

A pharmaceutical composition of the invention is formulated to be compatible with its intended route of administration. In an embodiment, the composition is formulated in accordance with routine procedures as a pharmaceutical composition adapted for intravenous, subcutaneous, intramuscular, oral, intranasal, or topical administration to human beings. In some embodiments, at least one of these Hsp90 inhibitory compounds (such as ganetespib) is formulated at a concentration of 8 mg/mL in 90% v/v PEG 300 and 10% v/v Polysorbate 80 for intravenous administration.

The invention also provides the use of at least one of these Hsp90 inhibitory compounds (such as ganetespib) or a pharmaceutically acceptable salt thereof for the manufacture of a medicament for the treatment of a subject with cancer with a mutation in ALK. The invention further provides the use of at least one of these Hsp90 inhibitory compounds (such as ganetespib) or a pharmaceutically acceptable salt thereof for the manufacture of a medicament for the treatment of a subject with a cancer with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides the use of at least one of these Hsp90 inhibitory compounds (such as ganetespib) or a pharmaceutically acceptable salt thereof for the manufacture of a medicament for the treatment of a subject with NSCLC cancer with a mutation in ALK. The invention further provides the use of at least one of these Hsp90 inhibitory compounds (such as ganetespib) or a pharmaceutically acceptable salt thereof for the manufacture of a medicament for the treatment of a subject with an ALK+NSCLC in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides at least one of these Hsp90 inhibitory compounds (such as ganetespib) or a pharmaceutically acceptable salt thereof for use in treating a subject with cancer with a mutation in ALK. The invention also provides at least one of these Hsp90 inhibitory compounds (such as ganetespib) or a pharmaceutically acceptable salt thereof for use in treating a subject with cancer with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides at least one of these Hsp90 inhibitory compounds (such as ganetespib) or a pharmaceutically acceptable salt thereof for use in treating a subject with a cancer with a mutation in ALK. The invention also provides at least one of these Hsp90 inhibitory compounds (such as ganetespib) or a pharmaceutically acceptable salt thereof for use in treating a subject with NSCLC with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides the use of at least one of these Hsp90 inhibitory compounds (such as ganetespib) or a pharmaceutically acceptable salt thereof for the manufacture of a medicament for the treatment of a subject with cancer with a mutation in ALK. The invention further provides the use of at least one of these Hsp90 inhibitory compounds (such as ganetespib) or a pharmaceutically acceptable salt thereof for the manufacture of a medicament for the treatment of a subject with a cancer with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides the use of at least one of these Hsp90 inhibitory compounds (such as ganetespib) or a pharmaceutically acceptable salt thereof for the manufacture of a medicament for the treatment of a subject with NSCLC cancer with a mutation in ALK. The invention further provides the use of at least one of these Hsp90 inhibitory compounds (such as ganetespib) or a pharmaceutically acceptable salt thereof for the manufacture of a medicament for the treatment of a subject with an ALK+NSCLC in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides at least one of these Hsp90 inhibitory compounds (such as ganetespib) or a pharmaceutically acceptable salt thereof for use in treating a subject with cancer with a mutation in ALK. The invention also provides at least one of these Hsp90 inhibitory compounds (such as ganetespib) or a pharmaceutically acceptable salt thereof for use in treating a subject with cancer with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

The invention also provides at least one of these Hsp90 inhibitory compounds (such as ganetespib) or a pharmaceutically acceptable salt thereof for use in treating a subject with a cancer with a mutation in ALK. The invention also provides at least one of these Hsp90 inhibitory compounds (such as ganetespib) or a pharmaceutically acceptable salt thereof for use in treating a subject with NSCLC with a mutation in ALK in combination with one or more of BEZ235, AZD6244, AZD8055, SN-38, gemcitabine, camptothecin, docetaxel, cisplatin, oxaliplatin, crizotinib, paclitaxel, trastuzumab, and pemetrexed.

ALK inhibitors described herein are those compounds that can inhibit anaplastic lymphoma kinase. Examples of ALK inhibitors include crizotinib (Pfizer, CAS Registry No. 877399-52-5), LDK-378 (Novartis), AF-802 (Chugai) and ASP-3026

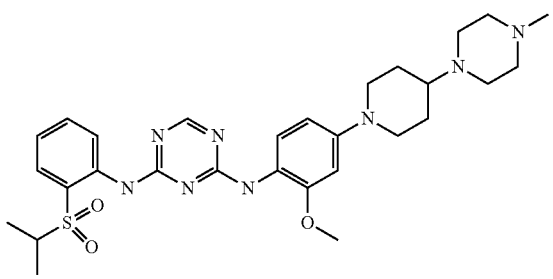 [SMILES: COc1cc(N2CCC(N3CCN(C)CC3)CC2)ccc1Nc1ncnc(Nc2ccccc2S(=O)(=O)C(C)C)n1]

(Astellas,).

c-Met is a receptor tyrosine kinase that is a client protein of Hsp90 and is encoded by the Met protooncogene. Hepatocyte growth factor (HGF) (also referred to as scatter factor (SF)) is the natural ligand of c-Met which binds to c-Met and leads to a variety of cellular responses such as proliferation, survival, angiogenesis, wound healing, tissue regeneration, scattering, motility, invasion and branching morphogenesis (Ma et al., *Cancer and Metastasis Reviews* (2003), 22: 309-325). c-Met and HGF are expressed in numerous tissues, although their expression is normally confined predominantly to cells of epithelial and mesenchymal origin, respectively. c-Met and HGF are required for normal mammalian development and have been shown to be important in cell migration, cell proliferation and survival, morphogenic differentiation, and organization of 3-dimensional tubular structures (e.g., renal tubular cells, gland formation, etc.). However, dysregulation of c-Met and/or HGF is believed to contribute to tumor growth, dissemination and invasion in several human cancers. c-Met and/or HGF are highly expressed in numerous cancers and their expression correlates with poor prognosis (Christensen, et al., *Cancer Research* (2003), 63:7345-7355). For example, c-Met receptor mutations have been shown to be expressed in a number of human cancers including hereditary and sporadic human papillary renal carcinomas, ovarian cancer, childhood hepatocellular carcinoma, metastatic head and neck squamous cell carcinomas, esophageal cancer and gastric cancer. Met gene amplification and over expression of c-Met has been shown to be associated with both non-small cell lung cancer (NSCLC) and small cell lung cancer (SCLC), as well as colorectal cancer, and the Tpr/Met fusion protein has been shown to be present in human osteogenic sarcoma and gastric cancer. Families with germine mutations that activate c-Met kinase are prone to multiple kidney tumors as well as tumors in other tissues. Numerous studies have correlated the expression of c-Met and/or HGF with the state of disease progression of different types of cancer (including lung, colon, breast, prostate, liver, pancreas, brain, kidney, ovarian, stomach, skin, and bone cancers).

The validity of targeting receptor tyrosine kinases (RTK) that are dysregulated in human cancers is illustrated by the successes of Gleevec targeting Bcr-Abl in chronic myelogenous leukemia and c-Kit in gastroinstinal stromal tumors, Herceptin in Her-2 overexpressing breast cancers, and Iressa in select NSCLC that have dysregulated EGFR. Compelling evidence exists for targeting c-Met in the treatment of human cancers and several small drug molecules that inhibit c-Met are currently in development. However, therapies that target specific RTK often work well initially for treating cancer but eventually fail due to additional mutations which allow RTK to maintain its activity in the presence of the drug. Moreover, the selective c-Met inhibitor SU11274, while highly affected against wild type c-Met and some mutants of c-Met, has been shown to be ineffective against other c-Met mutants (Berthou, et al., *Oncogene* (2004), 23:5387-5393). Therefore, a need exists to develop new anticancer therapeutics that reduce the expression and/or activity of c-Met via a different mechanism than therapeutics that directly inhibit c-Met.

Mutations or protein expression levels are preferably detected in a subject sample from the cancer tissue or tumor tissue, e.g., cells, extracellular matrix, and other naturally occurring components associated with the tumor. The mutation or expression level can be detected in a biopsy sample or in a surgical sample after resection of the tumor. The term "sample" as used herein refers to a collection of similar fluids, cells, or tissues isolated from a subject. The term "sample" includes any body fluid (e.g., urine, serum, blood fluids, lymph, gynecological fluids, cystic fluid, ascetic fluid, ocular fluids, and fluids collected by bronchial lavage and/or peritoneal rinsing), ascites, tissue samples (e.g., tumor samples) or a cell from a subject. Other subject samples include tear drops, serum, cerebrospinal fluid, feces, sputum, and cell extracts. In an embodiment, the sample is removed from the subject. In a particular embodiment, the sample is urine or serum. In an embodiment, the sample comprises cells. In another embodiment, the sample does not comprise cells. In certain embodiments, the sample can be the portion of the subject that is imaged. Samples are typically removed from the subject prior to analysis; however, tumor samples can be analyzed in the subject, for example, using imaging or other detection methods.

As used herein, the terms "identify" or "select" refer to a choice in preference to another. In other words, to identify a subject or select a subject is to perform the active step of picking out that particular subject from a group and confirming the identity of the subject by name or other distinguishing feature. With respect to the instant invention, it is understood that identifying a subject or selecting a subject as having one or more mutations in one or more genes of interest, having a wild-type gene, or having a change in the expression level of a protein, and can include any of a number of acts including, but not limited to, performing a test and observing a result that is indicative of a subject having a specific mutation; reviewing a test result of a subject and identifying the subject as having a specific mutation; reviewing documentation on a subject stating that the subject has a specific mutation and identifying the subject as the one discussed in the documentation by confirming the identity of the subject e.g., by an identification card, hospital bracelet, asking the subject for his/her name and/or other personal information to confirm the subjects identity.

As used herein, the term "refractory" cancer or tumor is understood as a malignancy which is either initially unresponsive to chemo- or radiation therapy, or which becomes unresponsive over time. A cancer refractory to on intervention may not be refractory to all interventions. A refractory cancer is typically not amenable to treatment with surgical interventions.

As used herein, "relapse" is understood as the return of a cancer or the signs and symptoms of a cancer after a period of improvement.

As used herein, "detecting", "detection" and the like are understood that an assay performed for identification of a specific analyte in a sample, e.g., a gene or gene product with a mutation, or the expression level of a gene or gene product in a sample, typically as compared to an appropriate control cell or tissue. The specific method of detection used is not a limitation of the invention. The detection method will typically include comparison to an appropriate control sample.

As used herein, the terms "treat", "treatment" and "treating" refer to the reduction or amelioration of the progression, severity and/or duration of a disease or disorder, delay of the onset of a disease or disorder, or the amelioration of one or more symptoms (preferably, one or more discernible symptoms) of a disease or disorder, resulting from the administration of one or more therapies (e.g., one or more therapeutic agents such as a compound of the invention). The terms "treat", "treatment" and "treating" also encompass the reduction of the risk of developing a disease or disorder, and the delay or inhibition of the recurrence of a disease or disorder. In one embodiment, the disease or disorder being treated is a proliferative disorder such as cancer. In specific embodiments, the terms "treat", "treatment" and "treating" refer to the amelioration of at least one measurable physical parameter of a disease or disorder, such as growth of a tumor, not necessarily discernible by the patient. In other embodiments the terms "treat", "treatment" and "treating" refer to the inhibition of the progression of a disease or disorder, e.g., a proliferative disorder, either physically by the stabilization of a discernible symptom, physiologically by the stabilization of a physical parameter, or both. In another embodiment, the terms "treat", "treatment" and "treating" of a proliferative disease or disorder refers to the reduction or stabilization of tumor size or cancerous cell count, and/or delay of tumor formation. In another embodiment, the terms "treat", "treating" and "treatment" also encompass the administration of a compound described herein as a prophylactic measure to patients with a predisposition (genetic or environmental) to any disease or disorder described herein.

As used herein, the terms "therapeutic agent" and "therapeutic agents" refer to any agent(s) that can be used in the treatment of a disease or disorder, e.g. a proliferative disorder, or one or more symptoms thereof. In certain embodiments, the term "therapeutic agent" refers to a compound described herein. In certain other embodiments, the term "therapeutic agent" does not refer to a compound described herein. Preferably, a therapeutic agent is an agent that is known to be useful for, or has been or is currently being used for the treatment of a disease or disorder, e.g., a proliferative disorder, or one or more symptoms thereof.

As used herein, the term "synergistic" refers to a combination of a compound described herein and another therapeutic agent, which, when taken together, is more effective than the additive effects of the individual therapies. A synergistic effect of a combination of therapies (e.g., a combination of therapeutic agents) permits the use of lower dosages of one or more of the therapeutic agent(s) and/or less frequent administration of the agent(s) to a subject with a disease or disorder, e.g., a proliferative disorder. The ability to utilize lower the dosage of one or more therapeutic agent and/or to administer the therapeutic agent less frequently reduces the toxicity associated with the administration of the agent to a subject without reducing the efficacy of the therapy in the treatment of a disease or disorder. In addition, a synergistic effect can result in improved efficacy of agents in the prevention, management or treatment of a disease or disorder, e.g. a proliferative disorder. Finally, a synergistic effect of a combination of therapies may avoid or reduce adverse or unwanted side effects associated with the use of either therapeutic agent alone.

As used herein, the phrase "side effects" encompasses unwanted and adverse effects of a therapeutic agent. Side effects are always unwanted, but unwanted effects are not necessarily adverse. An adverse effect from a therapeutic agent might be harmful or uncomfortable or risky to a subject. Side effects include fever, chills, lethargy, gastrointestinal toxicities (including gastric and intestinal ulcerations and erosions), nausea, vomiting, neurotoxicities, nephrotoxicities, renal toxicities (including such conditions as papillary necrosis and chronic interstitial nephritis), hepatic toxicities (including elevated serum liver enzyme levels), myelotoxicities (including leukopenia, myelosuppression, thrombocytopenia and anemia), dry mouth, metallic taste, prolongation of gestation, weakness, somnolence, pain (including muscle pain, bone pain and headache), hair loss, asthenia, dizziness, extra-pyramidal symptoms, akathisia, cardiovascular disturbances and sexual dysfunction.

As used herein, the terms "therapies" and "therapy" can refer to any protocol(s), method(s), and/or agent(s) that can be used in the prevention, treatment, management, or amelioration of a disease or disorder, e.g., a proliferative disorder, or one or more symptoms thereof.

A used herein, a "protocol" includes dosing schedules and dosing regimens. The protocols herein are methods of use and include therapeutic protocols.

As used herein, a composition that "substantially" comprises a compound means that the composition contains more than about 80% by weight, more preferably more than about 90% by weight, even more preferably more than about 95% by weight, and most preferably more than about 97% by weight of the compound.

When administered to a subject (e.g., a non-human animal for veterinary use or for improvement of livestock or to a human for clinical use), the compounds described herein are administered in an isolated form, or as the isolated form in a pharmaceutical composition. As used herein, "isolated" means that the compounds described herein are separated from other components of either: (a) a natural source, such as a plant or cell, preferably bacterial culture, or (b) a synthetic organic chemical reaction mixture. Preferably, the compounds described herein are purified via conventional techniques. As used herein, "purified" means that when isolated, the isolate contains at least 95%, preferably at least 98%, of a compound described herein by weight of the isolate either as a mixture of stereoisomers, or as a diastereomeric or enantiomeric pure isolate.

The invention, in an embodiment, provides the use of an Hsp90 inhibitors described herein, such as ganetespib, or a pharmaceutically acceptable salt or tautomer thereof:

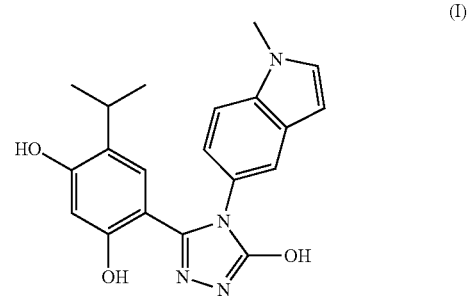 [SMILES: CC(C)c1cc(-c2nnc(O)n2-c2ccc3c(ccn3C)c2)c(O)cc1O]

(I)

for the treatment of cancer.

In an embodiment, the treatment method includes administering to a subject an effective amount of the compounds described herein, e.g., ganetespib, from about 2 mg/m² to about 260 mg/m². In an embodiment, the compound is administered once weekly. In an embodiment, compound is administered twice-weekly. In an embodiment, the compound is administered for about 3 weeks. In another embodiment, the administration for 3 weeks is repeated after about 7 days dose-free. In an embodiment, the administration after 7 days dose-free is repeated at two or more times. In an embodiment, the compound is administered by intravenous infusion, such as peripheral intravenous infusion. In an embodiment, the compound is infused over 60 minutes.

The invention provides methods for the treatment of subjects with a mutation in ALK. Cancers with a mutation in ALK are difficult to treat. The methods provided herein allow for treatment of such cancers that are typically resistant to treatment.

In an embodiment, the method is used for treating a subject with NSCLC. In an embodiment, the NSCLC is ALK+ (i.e., has a mutation in ALK.) In an embodiment, the NSCLC is refractory. In an embodiment, the NSCLC was previously treated with other anticancer agents. In an embodiment, the NSCLC was previously treated with crizotinib. In an embodiment, the NSCLC was treated with and became resistant to the crizotinib treatment. In an embodiment, the cancer is stage IIIB or IV NSCLC.

In an embodiment, the Hsp90 inhibitors described herein are used for treating a subject with NSCLC with a mutation in ALK. In an embodiment, the treatment method includes administering to the subject with NSCLC with a mutation in ALK an effective amount of the compounds described herein, e.g., ganetespib, or a pharmaceutically acceptable salt or tautomer thereof. In an embodiment, the compound is used for treating a subject with NSCLC with a mutation in ALK in combination with one or more additional anticancer agents.

In an embodiment, the compound is used for treating ALK+ NSCLC in combination with one or more of BEZ235, AZD6244, AZD8055, SN-38, gemcitabine, camptothecin, docetaxel, cisplatin, oxaliplatin, crizotinib, paclitaxel, trastuzumab, pemetrexed, erlotinib, bevacizumab, carboplatin, bortezomib, topotecan, cetuximab, gemcitabine, and tetracycline.

In an embodiment, the method of treating a subject with a cancer with a mutation in ALK includes:
 a) identifying a subject with a mutation in an ALK gene; and
 b) administering to the subject an effective amount of one the compounds described herein, e.g., ganetespib, or a pharmaceutically acceptable salt or tautomer thereof. In an embodiment, the method further comprises administering one or more additional anticancer drugs. In an embodiment, the one or more drugs are selected from the group consisting of BEZ235, AZD6244, AZD8055, SN-38, gemcitabine, camptothecin, docetaxel, cisplatin, oxaliplatin, crizotinib, paclitaxel, trastuzumab, and pemetrexed.

In an embodiment, the method of treating a subject with a NSCLC with a mutation in ALK includes:
 a) identifying a subject with a mutation in an ALK gene; and
 b) administering to the subject an effective amount of one of the compounds described herein or a pharmaceutically acceptable salt or tautomer thereof. In an embodiment, the method further comprises administering one or more additional anticancer drugs. In an embodiment, the one or more drugs are selected from the group consisting of BEZ235, AZD6244, AZD8055, SN-38, gemcitabine, camptothecin, docetaxel, cisplatin, oxaliplatin, crizotinib, paclitaxel, trastuzumab, and pemetrexed.

In one aspect, the method includes treating cancer in a subject, wherein the subject has cancer with a mutation in ALK, the method comprising administering to the subject an effective amount of an Hsp90 inhibitory compound shown in Tables 1 or 2, or according to formula (I) or (Ia) as set forth below:

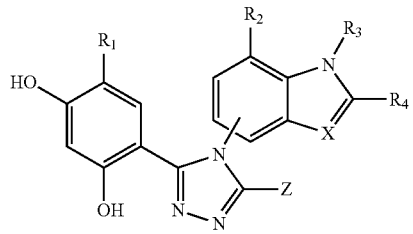

(I)

or

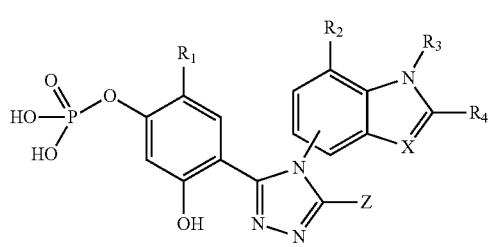

(Ia)

or a tautomer, or a pharmaceutically acceptable salt thereof; wherein:
Z is OH, SH, or $NH_2$;
X is $CR_4$ or N;
$R_1$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanidino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$OS(O)_pNR_{10}R_{11}$, —$S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;
$R_2$ is —H, —OH, —SH, —$NR_7H$, —$OR_{15}$, —$SR_{15}$, —$NHR_{15}$, —$O(CH_2)_mOH$, —$O(CH_2)_mSH$, —$O(CH_2)_mNR_7H$, —$S(CH_2)_mOH$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$;
$R_3$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —$C(O)R_7$, —$(CH_2)_mC(O)OR_7$, —$C(O)OR_7$, —$OC(O)R_7$, —$C(O)NR_{10}R_{11}$, —$S(O)_pR_7$, —$S(O)_pOR_7$, or —$S(O)_pNR_{10}R_{11}$;
$R_4$ is —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanidino, a haloalkyl, a heteroalkyl, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, —S(O)$_p$NR$_{10}$R$_{11}$, or R$_3$ and R$_4$ taken together with the carbon atoms to which they are attached form an optionally substituted cycloalkenyl, an optionally substituted aryl, an optionally substituted heterocyclyl, or an optionally substituted heteroaryl;

R$_7$ and R$_8$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{15}$, for each occurrence, is independently, a lower alkyl;

p, for each occurrence, is, independently, 1 or 2; and m, for each occurrence, is independently, 1, 2, 3, or 4.

In an embodiment, in formula (I) or (Ia), X is CR$_4$. In another embodiment, X is N.

In another embodiment, in formula (I) or (Ia), R$_1$ may be —H, lower alkyl, lower alkoxy, lower cycloalkyl, and lower cycloalkoxy.

In another embodiment, in formula (I) or (Ia), R$_1$ may be —H, methyl, ethyl, propyl, isopropyl, cyclopropyl, methoxy, ethoxy, propoxy, and cyclopropoxy.

In another embodiment, in formula (I) or (Ia), R$_3$ may be —H, a lower alkyl, a lower cycloalkyl, —C(O)N(R$_{27}$)$_2$, and —C(O)OH, wherein R$_{27}$ is —H or a lower alkyl.

In another embodiment, in formula (I) or (Ia), R$_3$ may be —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$.

In another embodiment, R$_4$ is H or a lower alkyl. In another embodiment, in formula (I) or (Ia), R$_4$ may be —H, methyl, ethyl, propyl, isopropyl or cyclopropyl.

In another embodiment, in formula (I) or (Ia), R$_1$ may be —H, —OH, —SH, —NH$_2$, a lower alkoxy and a lower alkyl amino. In another embodiment, in formula (I) or (Ia), R$_1$ may be —H, —OH, methoxy and ethoxy.

In another embodiment, in formula (I) or (Ia), Z is —OH. In another embodiment, in formula (I) or (Ia), Z is —SH.

In another embodiment, in formula (I) or (Ia), R$_2$ may be —H, —OH, —SH, —NH$_2$, a lower alkoxy and a lower alkyl amino. In another embodiment, in formula (I) or (Ia), R$_2$ may be —H, —OH, methoxy, and ethoxy.

In another embodiment, in formula (I) or (Ia), R$_1$ may be —H, methyl, ethyl, propyl, isopropyl, cyclopropyl, methoxy, ethoxy, propoxy, and cyclopropoxy; R$_3$ may be —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$; R$_4$ may be —H, methyl, ethyl, propyl, isopropyl or cyclopropyl; R$_2$ may be —H, —OH, —SH, —NH$_2$, a lower alkoxy and a lower alkyl amino; and Z may be OH.

In another embodiment, in formula (I) or (Ia), R$_1$ may be —H, methyl, ethyl, propyl, isopropyl, cyclopropyl, methoxy, ethoxy, propoxy, and cyclopropoxy; R$_3$ may be —H, methyl, ethyl, n-propyl, isopropyl, cyclopropyl, n-butyl, sec-butyl, tert-butyl, n-pentyl, n-hexyl, —C(O)OH, —(CH$_2$)$_m$C(O)OH, —CH$_2$OCH$_3$, —CH$_2$CH$_2$OCH$_3$, and —C(O)N(CH$_3$)$_2$; R$_4$ may be —H, methyl, ethyl, propyl, isopropyl or cyclopropyl; R$_2$ may be —H, —OH, —SH, —NH$_2$, a lower alkoxy and a lower alkyl amino; and Z may be SH.

In another embodiment, the compound may be:

3-(2,4-dihydroxy-5-ethyl-phenyl)-4-(1,3-dimethyl-indol-5-yl)-5-hydroxy-[1,2,4]triazole,
3-(2,4-dihydroxy-5-isopropyl-phenyl)-4-(1,3-dimethyl-indol-5-yl)-5-hydroxy-[1,2,4]triazole,
3-(2,4-dihydroxy-5-isopropyl-phenyl)-4-(1-methyl-indol-5-yl)-5-hydroxy-[1,2,4]triazole,
3-(2,4-dihydroxy-5-isopropyl-phenyl)-4-(1-isopropyl-indol-4-yl)-5-hydroxy-[1,2,4]triazole,
3-(2,4-dihydroxy-5-isopropyl-phenyl)-4-(1-methyl-indazol-5-yl)-5-mercapto-[1,2,4]triazole,
3-(2,4-dihydroxy-5-isopropyl-phenyl)-4-(1-methyl-indazol-6-yl)-5-mercapto-[1,2,4]triazole,
3-(2,4-dihydroxyphenyl)-4-(1-ethyl-indol-4-yl)-5-mercapto-[1,2,4]triazole,
3-(2,4-dihydroxyphenyl)-4-(1-isopropyl-indol-4-yl)-5-mercapto-[1,2,4]triazole,
3-(2,4-dihydroxyphenyl)-4-(indol-4-yl)-5-mercapto-[1,2,4]triazole,
3-(2,4-dihydroxyphenyl)-4-(1-methoxyethyl-indol-4-yl)-5-mercapto-[1,2,4]triazole,
3-(2,4-dihydroxy-5-ethyl-phenyl)-4-(1-isopropyl-indol-4-yl)-5-mercapto-[1,2,4]triazole,
3-(2,4-dihydroxyphenyl)-4-(1-dimethylcarbamoyl-indol-4-yl)-5-mercapto-[1,2,4]triazole,
3-(2,4-dihydroxy-5-ethyl-phenyl)-4-(1-propyl-indol-4-yl)-5-mercapto-[1,2,4]triazole,
3-(2,4-dihydroxy-5-ethyl-phenyl)-4-(1,2,3-trimethyl-indol-5-yl)-5-mercapto-[1,2,4]triazole,
3-(2,4-dihydroxy-5-ethyl-phenyl)-4-(2,3-dimethyl-indol-5-yl)-5-mercapto-[1,2,4]triazole,
3-(2,4-dihydroxy-5-ethyl-phenyl)-4-(1-acetyl-2,3-dimethyl-indol-5-yl)-5-mercapto-[1,2,4]triazole,
3-(2,4-dihydroxy-5-ethyl-phenyl)-4-(1-propyl-2,3-dimethyl-indol-5-yl)-5-mercapto-[1,2,4]triazole,
3-(2,4-dihydroxy-5-ethyl-phenyl)-4-(1-n-butyl-indol-4-yl)-5-mercapto-[1,2,4]triazole,
3-(2,4-dihydroxy-5-ethyl-phenyl)-4-(1-n-pentyl-indol-4-yl)-5-mercapto-[1,2,4]triazole,
3-(2,4-dihydroxy-5-ethyl-phenyl)-4-(1-n-hexyl-indol-4-yl)-5-mercapto-[1,2,4]triazole,
3-(2,4-dihydroxy-5-cyclopropyl-phenyl)-4-(1-(1-methylcyclopropyl)-indol-4-yl)-5-mercapto-[1,2,4]-triazole,
3-(2,4-dihydroxy-5-cyclopropyl-phenyl)-4-(1,2,3-trimethyl-indol-5-yl)-5-mercapto-[1,2,4]triazole,
3-(2,4-dihydroxy-5-ethyl-phenyl)-4-(1-methyl-3-ethyl-indol-5-yl)-5-mercapto-[1,2,4]triazole,
3-(2,4-dihydroxy-5-ethyl-phenyl)-4-(1,3-dimethyl-indol-5-yl)-5-mercapto-[1,2,4]triazole,
3-(2,4-dihydroxy-5-ethyl-phenyl)-4-(1-methyl-3-isopropyl-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-ethyl-phenyl)-4-(N-methyl-indol-5-yl)-5-mercapto-[1,2,4]triazole, 3-(2,4-dihydroxy-5-isopropyl-phenyl)-4-(1,3-dimethyl-indol-5-yl)-5-mercapto-[1,2,4]triazole,
3-(2,4-dihydroxy-5-cyclopropyl-phenyl)-4-(1,3-dimethyl-indol-5-yl)-5-mercapto-[1,2,4]triazole,
3-(2,4-dihydroxy-5-cyclopropyl-phenyl)-4-(1-methyl-indol-5-yl)-5-mercapto-[1,2,4]triazole,
3-(2,4-dihydroxy-5-isopropyl-phenyl)-4-(1H-indol-5-yl)-5-mercapto-[1,2,4]triazole,
3-(2,4-dihydroxy-5-ethyl-phenyl)-4-(1,2-dimethyl-indol-5-yl)-5-mercapto-[1,2,4]triazole,
3-(2,4-dihydroxy-5-isopropyl-phenyl)-4-(1-ethyl-indol-5-yl)-5-mercapto-[1,2,4]triazole,
3-(2,4-dihydroxy-5-isopropyl-phenyl)-4-(1-propyl-indol-5-yl)-5-mercapto-[1,2,4]triazole, or a tautomer, or a pharmaceutically acceptable salt thereof.

In another embodiment, the compound may be:
3-(2,4-dihydroxy-5-ethyl-phenyl)-4-(1-ethyl-benzimidazol-4-yl)-5-mercapto-[1,2,4]triazole,
3-(2,4-dihydroxy-5-ethyl-phenyl)-4-(1-ethyl-benzimidazol-4-yl)-5-mercapto-[1,2,4]triazole HCL salt,
3-(2,4-dihydroxy-5-ethyl-phenyl)-4-(2-methyl-3-ethyl-benzimidazol-5-yl)-5-mercapto-[1,2,4]triazole,
3-(2,4-dihydroxy-5-ethyl-phenyl)-4-(1-ethyl-2-methyl-benzimidazol-5-yl)-5-mercapto-[1,2,4]triazole,
3-(2,4-dihydroxy-5-isopropyl-phenyl)-4-(1-methyl-2-trifluoromethyl-benzimidazol-5-yl)-5-mercapto-[1,2,4]triazole, or a tautomer, or a pharmaceutically acceptable salt thereof.

In another embodiment, the compound may be:
5-hydroxy-4-(5-hydroxy-4-(1-methyl-1H-indol-5-yl)-4H-1,2,4-triazol-3-yl)-2-isopropylphenyl dihydrogen phosphate,
sodium 5-hydroxy-4-(5-hydroxy-4-(1-methyl-1H-indol-5-yl)-4H-1,2,4-triazol-3-yl)-2-isopropylphenyl phosphate,
2-(3,4-dimethoxyphenethyl)-5-hydroxy-4-(5-hydroxy-4-(1-methyl-1H-indol-5-yl)-4H-1,2,4-triazol-3-yl)phenyl dihydrogen phosphate,
5-hydroxy-2-isopropyl-4-(5-mercapto-4-(4-methoxybenzyl)-4H-1,2,4-triazol-3-yl)phenyl dihydrogen phosphate,
5-hydroxy-4-(5-hydroxy-4-(4-methoxybenzyl)-4H-1,2,4-triazol-3-yl)-2-isopropylphenyl dihydrogen phosphate,
4-(4-(1,3-dimethyl-1H-indol-5-yl)-5-hydroxy-4H-1,2,4-triazol-3-yl)-2-ethyl-5-hydroxyphenyl dihydrogen phosphate, or a tautomer, or a pharmaceutically acceptable salt thereof.

Hsp90 inhibitory compounds, as well as tautomers or pharmaceutically acceptable salts thereof, that may be used in the methods described herein are depicted in Tables 1 or 2.

TABLE 1

| | STRUCTURE | TAUTOMERIC STRUCTURE | NAME |
|---|---|---|---|
| 1 | 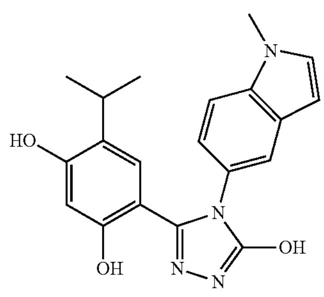 [SMILES: CC(C)c1cc(-c2nnc(O)n2-c2ccc3c(ccn3C)c2)c(O)cc1O] | | 3-(2,4-dihydroxy-5-isopropyl-phenyl)-4-(1-methyl-indol-5-yl)-5-hydroxy-[1,2,4]triazole (ganetespib) |
| 2 | 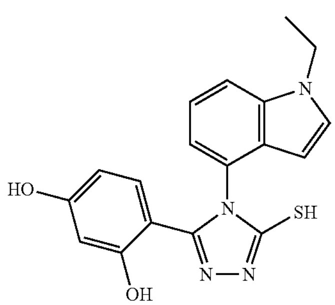 [SMILES: CCn1ccc2c(-n3c(S)nnc3-c3ccc(O)cc3O)cccc21] | | 3-(2,4-Dihydroxyphenyl)-4-(1-ethyl-indol-4-yl)-5-mercapto-[1,2,4] triazole |
| 3 | 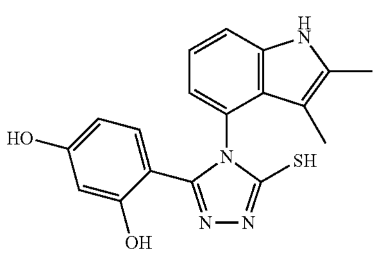 [SMILES: Cc1[nH]c2cccc(-n3c(S)nnc3-c3ccc(O)cc3O)c2c1C] | | 3-(2,4-Dihydroxyphenyl)-4-(2,3-dimethyl-1H-indol-4-yl)-5-mercapto-[1,2,4] triazole |

TABLE 1-continued

| | STRUCTURE | TAUTOMERIC STRUCTURE | NAME |
|---|---|---|---|
| 4 | 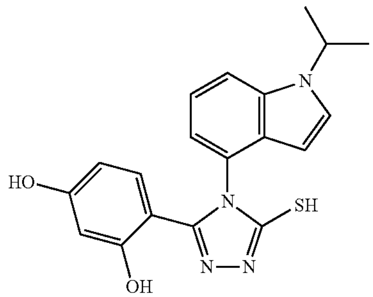 [SMILES: CC(C)n1ccc2c(-n3c(S)nnc3-c3ccc(O)cc3O)cccc21] | | 3-(2,4-Dihydroxyphenyl)-4-(1-isopropyl-indol-4-yl)-5-mercapto-[1,2,4] triazole |
| 5 | 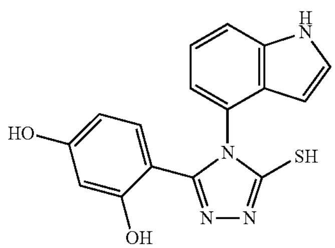 [SMILES: Oc1ccc(-c2nnc(S)n2-c2cccc3[nH]ccc23)c(O)c1] | | 3-(2,4-Dihydroxy-phenyl)-4-(indol-4-yl)-5-mercapto-[1,2,4] triazole |
| 6 | 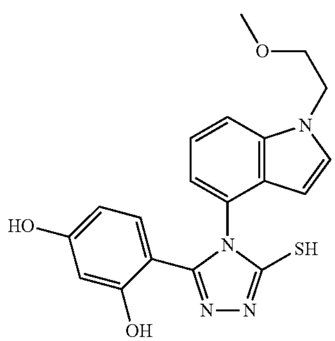 [SMILES: COCCn1ccc2c(-n3c(S)nnc3-c3ccc(O)cc3O)cccc21] | | 3-(2,4-Dihydroxy-phenyl)-4-[1-(2-methoxyethoxy)-indol-4-yl]-5-mercapto-[1,2,4] triazole |
| 7 | 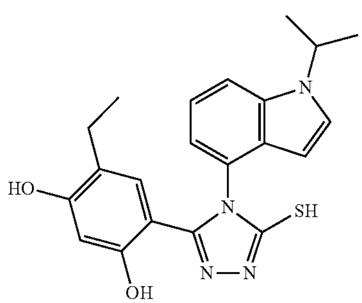 [SMILES: CCc1cc(-c2nnc(S)n2-c2cccc3c2ccn3C(C)C)c(O)cc1O] | | 3-(2,4-Dihydroxy-5-ethyl-phenyl)-4-(1-isopropyl-indol-4-yl)-5-mercapto-[1,2,4] triazole |
| 8 | 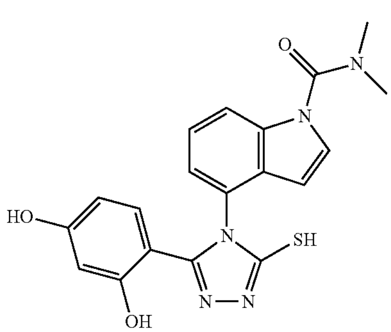 [SMILES: CN(C)C(=O)n1ccc2c(-n3c(S)nnc3-c3ccc(O)cc3O)cccc21] | | 3-(2,4-Dihydroxy-5-ethyl-phenyl)-4-[1-(dimethyl-carbamoyl)-indol-4-yl]-5-mercapto-[1,2,4] triazole |

TABLE 1-continued

| STRUCTURE | TAUTOMERIC STRUCTURE | NAME |
|---|---|---|
| 9 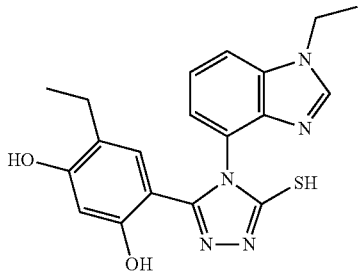 [SMILES: CCc1cc(-c2nnc(S)n2-c2cccc3c2ncn3CC)c(O)cc1O] | 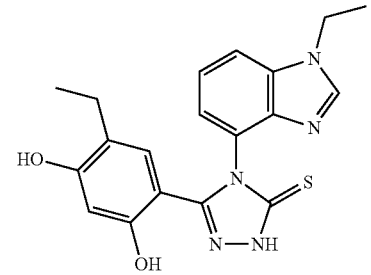 [SMILES: CCc1cc(-c2n[nH]c(=S)n2-c2cccc3c2ncn3CC)c(O)cc1O] | 3-(2,4-Dihydroxy-5-ethyl-phenyl)-4-(1-ethyl-benzoimidazol-4-yl)-5-mercapto-[1,2,4]triazole |
| 10 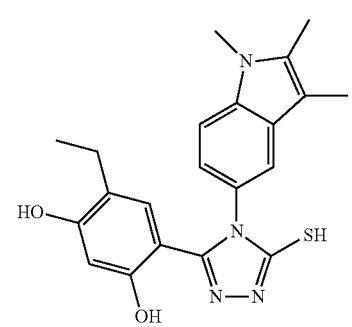 [SMILES: CCc1cc(-c2nnc(S)n2-c2ccc3c(c2)c(C)c(C)n3C)c(O)cc1O] | 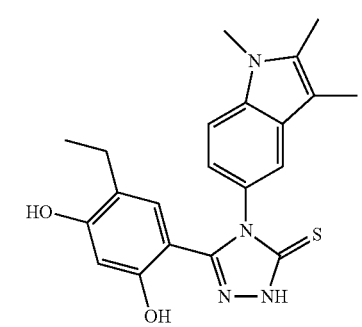 [SMILES: CCc1cc(-c2n[nH]c(=S)n2-c2ccc3c(c2)c(C)c(C)n3C)c(O)cc1O] | 3-(2,4-Dihydroxy-5-ethyl-phenyl)-4-(1,2,3-trimethyl-indol-5-yl)-5-mercapto-[1,2,4]triazole |
| 11 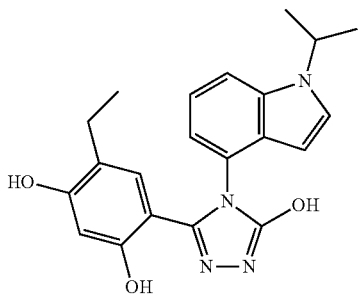 [SMILES: CCc1cc(-c2nnc(O)n2-c2cccc3c2ccn3C(C)C)c(O)cc1O] | 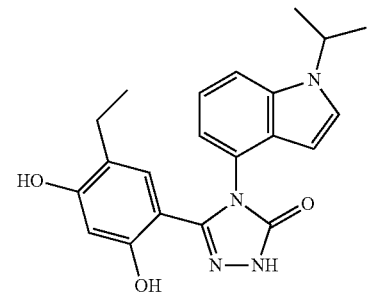 [SMILES: CCc1cc(-c2n[nH]c(=O)n2-c2cccc3c2ccn3C(C)C)c(O)cc1O] | 3-(2,4-Dihydroxy-5-ethyl-phenyl)-4-(1-isopropyl-indol-3-yl)-5-hydroxy-[1,2,4]triazole |
| 12 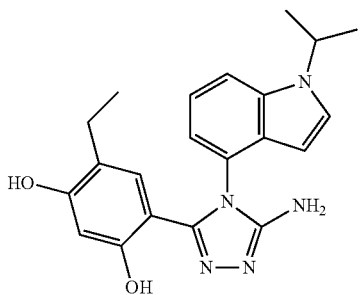 | 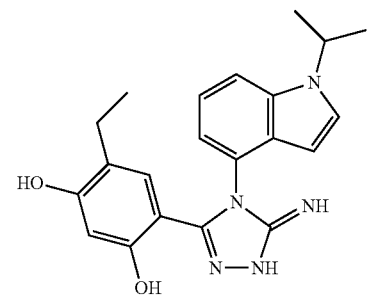 [SMILES: CCc1cc(-c2n[nH]c(=N)n2-c2cccc3c2ccn3C(C)C)c(O)cc1O] | 3-(2,4-Dihydroxy-5-ethyl-phenyl)-4-(1-isopropyl-indol-4-yl)-5-amino-[1,2,4]triazole |
| 15 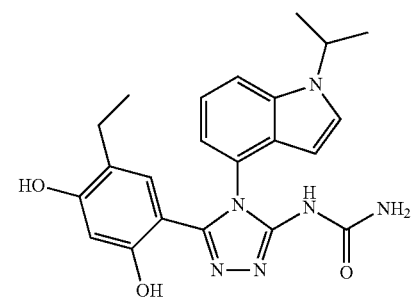 [SMILES: CCc1cc(-c2nnc(NC(N)=O)n2-c2cccc3c2ccn3C(C)C)c(O)cc1O] |  | 3-(2,4-Dihydroxy-5-ethyl-phenyl)-4-(1-isopropyl-indol-4-yl)-5-ureido-[1,2,4]triazole |

TABLE 1-continued

| | STRUCTURE | TAUTOMERIC STRUCTURE | NAME |
|---|---|---|---|
| 16 | 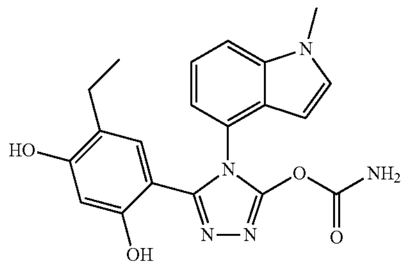 [SMILES: CCc1cc(-c2nnc(OC(N)=O)n2-c2cccc3c2ccn3C)c(O)cc1O] | | 3-(2,4-Dihydroxy-5-ethyl-phenyl)-4-(1-methyl-indol-4-yl)-5-carbamoyloxy-[1,2,4] triazole |
| 17 | 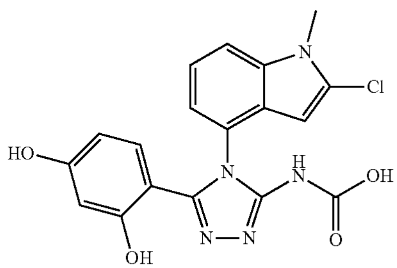 [SMILES: Cn1c(Cl)cc2c(-n3c(NC(=O)O)nnc3-c3ccc(O)cc3O)cccc21] | | 3-(2,4-Dihydroxy-phenyl)-4-(1-methyl-2-chloro-indol-4-yl)-5-carbamoyloxy-[1,2,4] triazole |
| 18 | 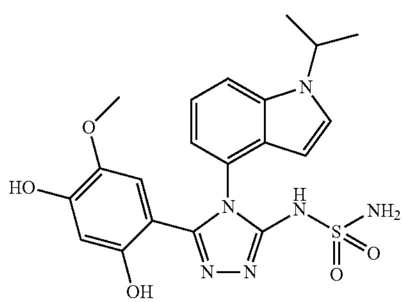 [SMILES: COc1cc(-c2nnc(NS(N)(=O)=O)n2-c2cccc3c2ccn3C(C)C)c(O)cc1O] | | 3-(2,4-Dihydroxy-5-methoxy-phenyl)-4-(1-isopropyl-benzoimidazol-4-yl)-5-(sulfamoylamino)-[1,2,4] triazole |
| 20 | 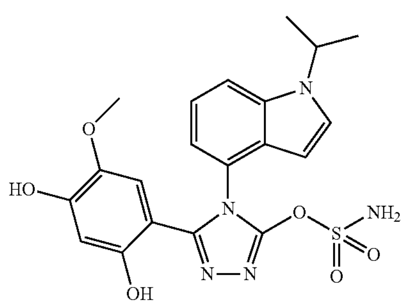 [SMILES: COc1cc(-c2nnc(OS(N)(=O)=O)n2-c2cccc3c2ccn3C(C)C)c(O)cc1O] | | 3-(2,4-Dihydroxy-5-methoxy-phenyl)-4-(1-isopropyl-benzoimidazol-4-yl)-5-(sulfamoyloxy)-[1,2,4] triazole |
| 21 | 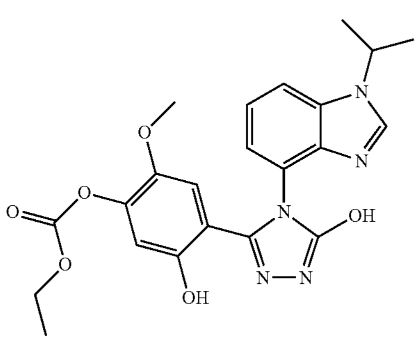 [SMILES: CCOC(=O)Oc1cc(O)c(-c2nnc(O)n2-c2cccc3c2ncn3C(C)C)cc1OC] | | 3-(2-Hydroxy-4-ethoxycarbonyoxy-5-methoxy-phenyl)-4-(1-isopropyl-benzoimidazol-4-yl)-5-hydroxy-[1,2,4] triazole |

TABLE 1-continued

| STRUCTURE | TAUTOMERIC STRUCTURE | NAME |
|---|---|---|
| 22 | | 3-[2-Hydroxy-4-isobutyryloxy-5-ethyl-phenyl]-4-(1-methyl-benzo-imidazol-4-yl)-5-hydroxy-[1,2,4] triazole |
| 23 | | 3-(2,4-Dihydroxy-phenyl)-4-(1-dimethylcarbamoyl-indol-4-yl)-5-mercapto-[1,2,4] triazole |
| 24 | | 3-(2,4-Dihydroxy-5-ethyl-phenyl)-4-(2,3-dimethyl-indol-5-yl)-5-mercapto-[1,2,4] triazole |
| 25 | | 3-(2,4-Dihydroxy-5-ethyl-phenyl)-4-(1-ethyl-1H-benzoimidazol-4-yl)-5-mercapto-[1,2,4] triazole, HCl salt |
| 26 | | 3-(2,4-Dihydroxy-5-ethyl-phenyl)-4-(1-isopropyl-7-methoxy-indol-4-yl)-5-mercapto-[1,2,4] triazole |

TABLE 1-continued

| | STRUCTURE | TAUTOMERIC STRUCTURE | NAME |
|---|---|---|---|
| 27 | 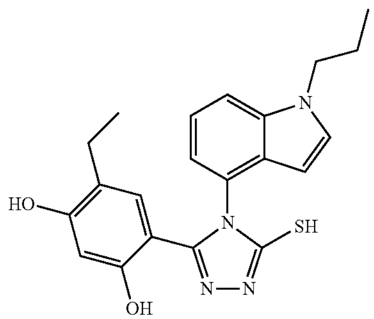 [SMILES: CCCn1ccc2c(-n3c(S)nnc3-c3cc(CC)c(O)cc3O)cccc21] | | 3-(2,4-dihydroxy-5-ethyl-phenyl)-4-(1-propyl-indol-4-yl)-5-mercapto-[1,2,4] triazole |
| 28 | 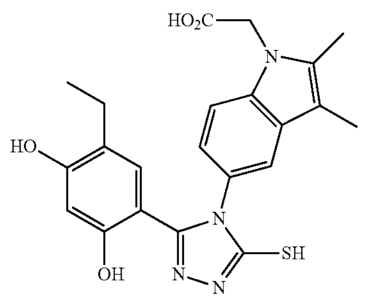 [SMILES: CCc1cc(-c2nnc(S)n2-c2ccc3c(c2)c(C)c(C)n3CC(=O)O)c(O)cc1O] | | 3-(2,4-dihydroxy-5-ethyl-phenyl)-4-(1-acetyl-2,3-dimethyl-indol-5-yl)-5-mercapto-[1,2,4] triazole |
| 29 | 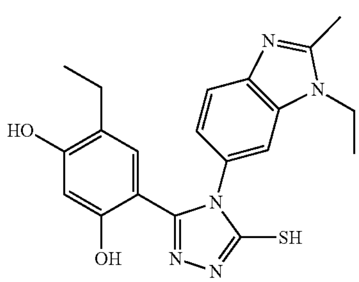 [SMILES: CCc1cc(-c2nnc(S)n2-c2ccc3nc(C)n(CC)c3c2)c(O)cc1O] | | 3-(2,4-dihydroxy-5-ethyl-phenyl)-4-(2-methyl-3-ethyl-benzimidazol-5-yl)-5-mercapto-[1,2,4] triazole |
| 30 | 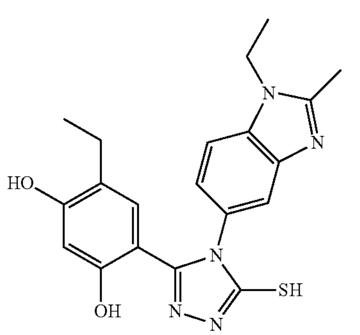 [SMILES: CCc1cc(-c2nnc(S)n2-c2ccc3c(c2)nc(C)n3CC)c(O)cc1O] | | 3-(2,4-dihydroxy-5-ethyl-phenyl)-4-(1-ethyl-2-methyl-benzimidazol-5-yl)-5-mercapto-[1,2,4] triazole |

TABLE 1-continued

| | STRUCTURE | TAUTOMERIC STRUCTURE | NAME |
|---|---|---|---|
| 31 | 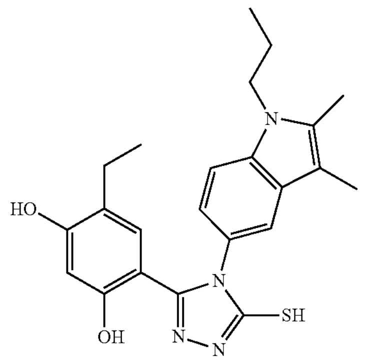 [SMILES: CCCn1c(C)c(C)c2cc(-n3c(S)nnc3-c3cc(CC)c(O)cc3O)ccc21] | | 3-(2,4-dihydroxy-5-ethyl-phenyl)-4-(1-propyl-2,3-dimethyl-indol-5-yl)-5-mercapto-[1,2,4] triazole |
| 34 | 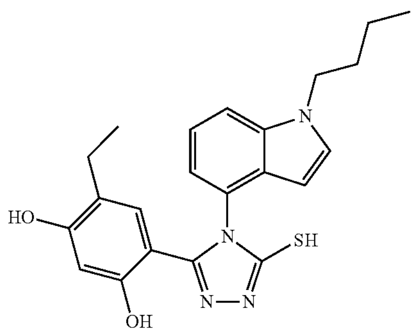 [SMILES: CCCCn1ccc2c(-n3c(S)nnc3-c3cc(CC)c(O)cc3O)cccc21] | | 3-(2,4-dihydroxy-5-ethyl-phenyl)-4-(1-n-butyl-indol-4-yl)-5-mercapto-[1,2,4] triazole |
| 35 | 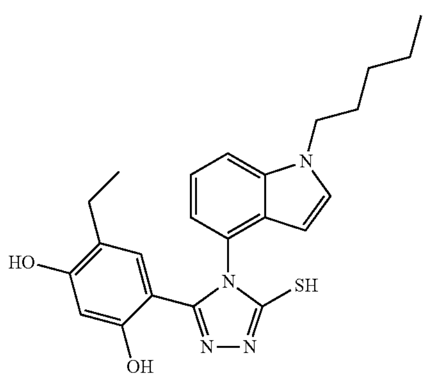 [SMILES: CCCCCn1ccc2c(-n3c(S)nnc3-c3cc(CC)c(O)cc3O)cccc21] | | 3-(2,4-dihydroxy-5-ethyl-phenyl)-4-(1-n-pentyl-indol-4-yl)-5-mercapto-[1,2,4] triazole |
| 36 | 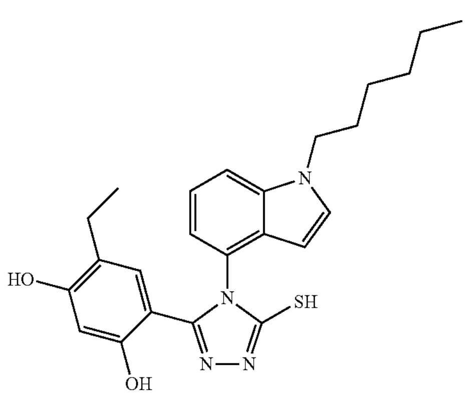 [SMILES: CCCCCCn1ccc2c(-n3c(S)nnc3-c3cc(CC)c(O)cc3O)cccc21] | | 3-(2,4-dihydroxy-5-ethyl-phenyl)-4-(1-n-hexyl-indol-4-yl)-5-mercapto-[1,2,4] triazole |

TABLE 1-continued

| STRUCTURE | TAUTOMERIC STRUCTURE | NAME |
|---|---|---|
| 37 | | 3-(2,4-dihydroxy-5-cyclopropyl-phenyl)-4-(1-(1-methylcyclopropyl)-indol-4-yl)-5-mercapto-[1,2,4] triazole |
| 38 | | 3-(2,4-dihydroxy-5-cyclopropyl-phenyl)-4-(1-isopropyl-7-methoxy-indol-4-yl)-5-mercapto-[1,2,4] triazole |
| 39 | | 3-(2,4-dihydroxy-5-cyclopropyl-phenyl)-4-(1,2,3-trimethyl-indol-5-yl)-5-mercapto-[1,2,4] triazole |
| 40 | | 3-(2,4-dihydroxy-5-ethyl-phenyl)-4-(1-isopropyl-7-methoxy-indol-4-yl)-5-mercapto-[1,2,4] triazole disodium salt |
| 41 | | 3-(2,4-dihydroxy-5-tert-butyl-phenyl)-4-(1-isopropyl-7-methoxy-indol-4-yl)-5-mercapto-[1,2,4] triazole |

TABLE 1-continued

| STRUCTURE | TAUTOMERIC STRUCTURE | NAME |
|---|---|---|
| 42 | | 3-(2,4-dihydroxy-5-cyclopropyl-phenyl)-4-(1-propyl-7-methoxy-indol-4-yl)-5-mercapto-[1,2,4] triazole |
| 43 | | 3-(2,4-dihydroxy-5-ethyl-phenyl)-4-(1-methyl-3-ethyl-indol-5-yl)-5-mercapto-[1,2,4] triazole |
| 44 | | 3-(2,4-dihydroxy-5-ethyl-phenyl)-4-(1,3-dimethyl-indol-5-yl)-5-mercapto-[1,2,4] triazole |
| 45 | | 3-(2,4-dihydroxy-5-isopropyl-phenyl)-4-(1-isopropyl-7-methoxy-indol-4-yl)-5-mercapto-[1,2,4] triazole |
| 46 | | 3-(2,4-dihydroxy-5-ethyl-phenyl)-4-(1-methyl-3-isopropyl-indol-5-yl)-5-mercapto-[1,2,4] triazole |

TABLE 1-continued

| | STRUCTURE | TAUTOMERIC STRUCTURE | NAME |
|---|---|---|---|
| 48 | 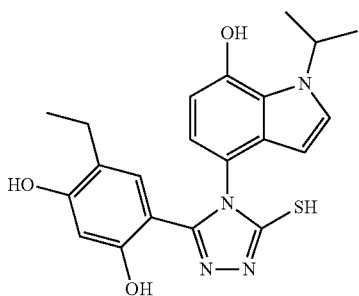 [SMILES: CCc1cc(-c2nnc(S)n2-c2ccc(O)c3c2ccn3C(C)C)c(O)cc1O] | 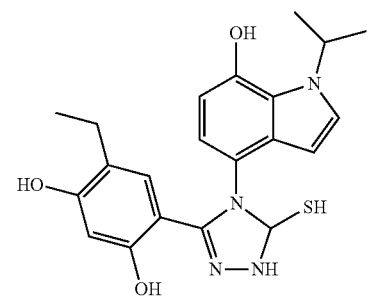 [SMILES: CCc1cc(C2=NNC(S)N2c2ccc(O)c3c2ccn3C(C)C)c(O)cc1O] | 3-(2,4-dihydroxy-5-ethyl-phenyl)-4-(1-isopropyl-7-hydroxy-indol-4-yl)-5-mercapto-[1,2,4] triazole |
| 49 | 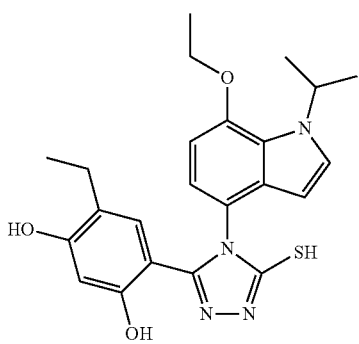 [SMILES: CCOc1ccc(-n2c(S)nnc2-c2cc(CC)c(O)cc2O)c2ccn(C(C)C)c12] | 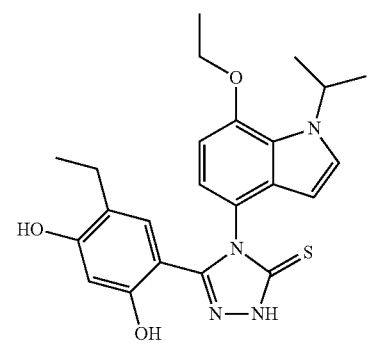 [SMILES: CCOc1ccc(-n2c(-c3cc(CC)c(O)cc3O)n[nH]c2=S)c2ccn(C(C)C)c12] | 3-(2,4-dihydroxy-5-ethyl-phenyl)-4-(1-isopropyl-7-ethoxy-indol-4-yl)-5-mercapto-[1,2,4] triazole |
| 50 | 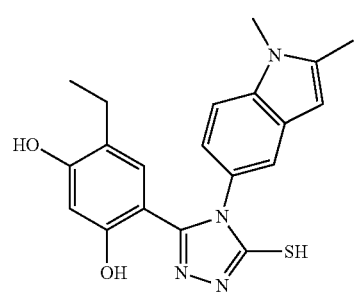 [SMILES: CCc1cc(-c2nnc(S)n2-c2ccc3c(c2)cc(C)n3C)c(O)cc1O] | 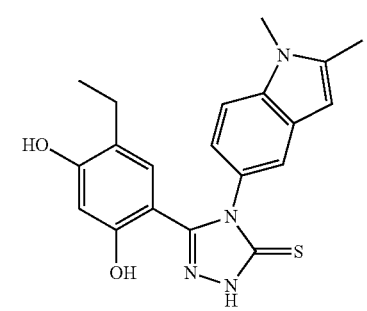 [SMILES: CCc1cc(-c2n[nH]c(=S)n2-c2ccc3c(c2)cc(C)n3C)c(O)cc1O] | 3-(2,4-dihydroxy-5-ethyl-phenyl)-4-(1,2-dimethyl-indol-5-yl)-5-mercapto-[1,2,4] triazole |
| 51 | 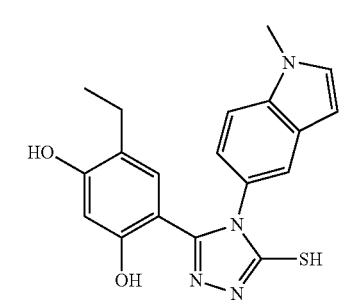 [SMILES: CCc1cc(-c2nnc(S)n2-c2ccc3c(ccn3C)c2)c(O)cc1O] | 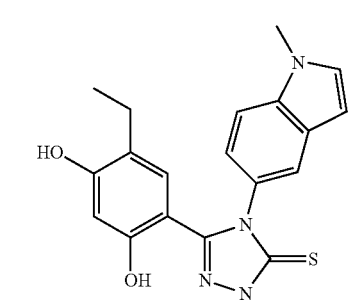 | 3-(2,4-dihydroxy-5-ethyl-phenyl)-4-(N-methyl-indol-5-yl)-5-mercapto-[1,2,4] triazole |
| 55 | 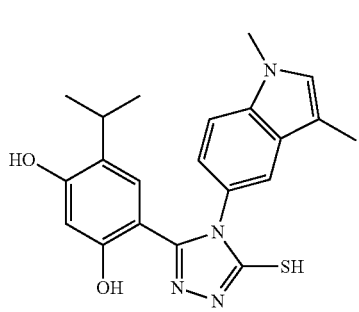 | 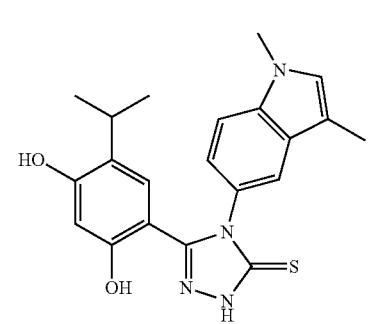 | 3-(2,4-dihydroxy-5-isopropyl-phenyl)-4-(1,3-dimethyl-indol-5-yl)-5-mercapto-[1,2,4] triazole |

TABLE 1-continued

| | STRUCTURE | TAUTOMERIC STRUCTURE | NAME |
|---|---|---|---|
| 56 | 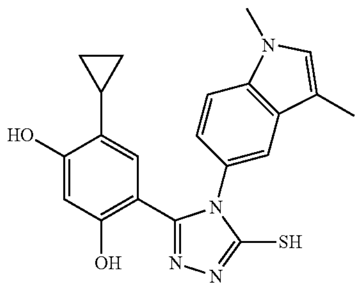 [SMILES: Cc1cn(C)c2ccc(-n3c(S)nnc3-c3cc(C4CC4)c(O)cc3O)cc12] | | 3-(2,4-dihydroxy-5-cyclopropyl-phenyl)-4-(1,3-dimethyl-indol-5-yl)-5-mercapto-[1,2,4] triazole |
| 57 | 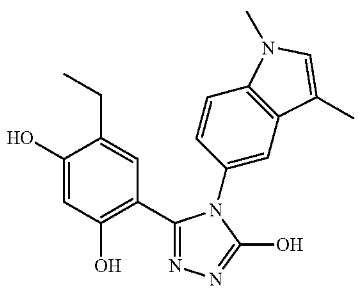 [SMILES: CCc1cc(-c2nnc(O)n2-c2ccc3c(c2)c(C)cn3C)c(O)cc1O] | | 3-(2,4-dihydroxy-5-ethyl-phenyl)-4-(1,3-dimethyl-indol-5-yl)-5-hydroxy-[1,2,4] triazole |
| 58 | 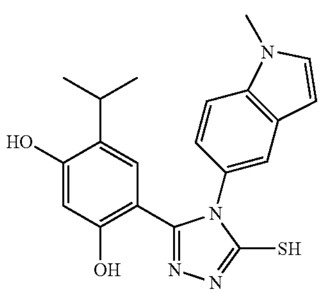 [SMILES: CC(C)c1cc(-c2nnc(S)n2-c2ccc3c(ccn3C)c2)c(O)cc1O] | | 3-(2,4-dihydroxy-5-isopropyl-phenyl)-4-(N-methyl-indol-5-yl)-5-mercapto-[1,2,4] triazole |
| 59 | 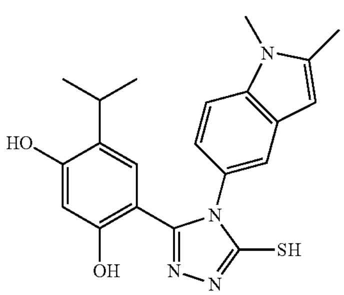 [SMILES: Cc1cc2cc(-n3c(S)nnc3-c3cc(C(C)C)c(O)cc3O)ccc2n1C] | | 3-(2,4-dihydroxy-5-isopropyl-phenyl)-4-(1,2-dimethyl-indol-5-yl)-5-mercapto-[1,2,4] triazole |
| 60 | 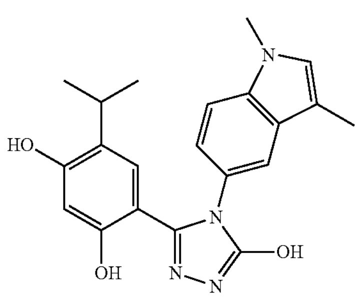 [SMILES: Cc1cn(C)c2ccc(-n3c(O)nnc3-c3cc(C(C)C)c(O)cc3O)cc12] | | 3-(2,4-dihydroxy-5-isopropyl-phenyl)-4-(1,3-dimethyl-indol-5-yl)-5-hydroxy-[1,2,4] triazole |

TABLE 1-continued

| | STRUCTURE | TAUTOMERIC STRUCTURE | NAME |
|---|---|---|---|
| 62 | 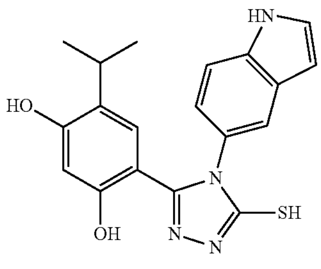 [SMILES: CC(C)c1cc(-c2nnc(S)n2-c2ccc3[nH]ccc3c2)c(O)cc1O] | | 3-(2,4-dihydroxy-5-isopropyl-phenyl)-4-(1H-indol-5-yl)-5-mercapto-[1,2,4] triazole |
| 63 | 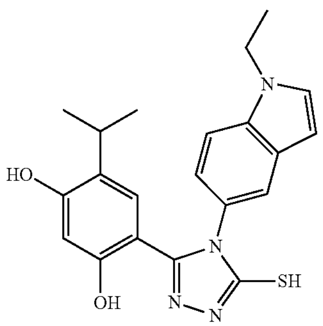 [SMILES: CCn1ccc2cc(-n3c(S)nnc3-c3cc(C(C)C)c(O)cc3O)ccc21] | | 3-(2,4-dihydroxy-5-isopropyl-phenyl)-4-(1-ethyl-indol-5-yl)-5-mercapto-[1,2,4] triazole |
| 64 | 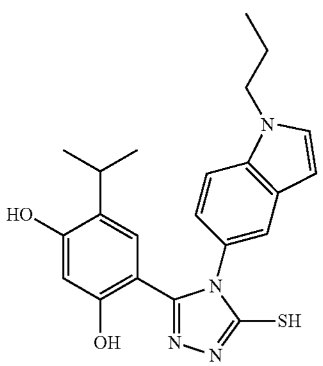 [SMILES: CCCn1ccc2cc(-n3c(S)nnc3-c3cc(C(C)C)c(O)cc3O)ccc21] | | 3-(2,4-dihydroxy-5-isopropyl-phenyl)-4-(1-propyl-indol-5-yl)-5-mercapto-[1,2,4] triazole |
| 65 | 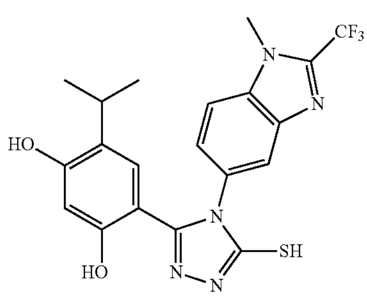 [SMILES: CC(C)c1cc(-c2nnc(S)n2-c2ccc3c(c2)nc(C(F)(F)F)n3C)c(O)cc1O] | | 3-(2,4-dihydroxy-5-isopropyl-phenyl)-4-(1-methyl-2-trifluoromethyl-benzimidazol-5-yl)-5-mercapto-[1,2,4] triazole |
| 66 | 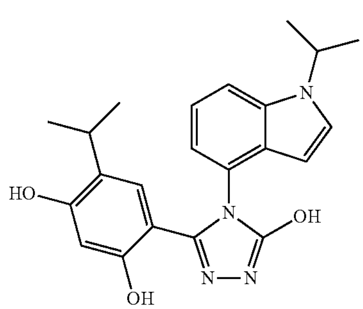 [SMILES: CC(C)c1cc(-c2nnc(O)n2-c2cccc3c2ccn3C(C)C)c(O)cc1O] | | 3-(2,4-dihydroxy-5-isopropyl-phenyl)-4-(1-isopropyl-indol-4-yl)-5-hydroxy-[1,2,4] triazole |

TABLE 2

Compounds according to Formula (Ia)

| NO. | STRUCTURE | TAUTOMERIC STRUCTURE | NAME |
|---|---|---|---|
| 1A | 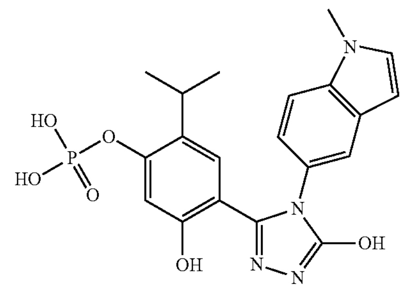 [SMILES: CC(C)c1cc(-c2nnc(O)n2-c2ccc3c(ccn3C)c2)c(O)cc1OP(=O)(O)O] | | 5-hydroxy-4-(5-hydroxy-4-(1-methyl-1H-indol-5-yl)-4H-1,2,4-triazol-3-yl)-2-isopropylphenyl dihydrogen phosphate |
| 2A | 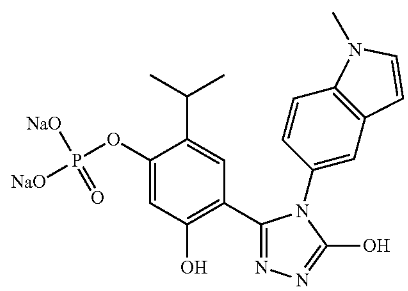 | | sodium 5-hydroxy-4-(5-hydroxy-4-(1-methyl-1H-indol-5-yl)-4H-1,2,4-triazol-3-yl)-2-isopropylphenyl phosphate |
| 3A | 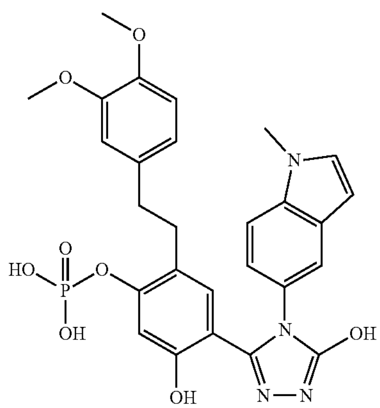 [SMILES: COc1ccc(CCc2cc(-c3nnc(O)n3-c3ccc4c(ccn4C)c3)c(O)cc2OP(=O)(O)O)cc1OC] | | 2-(3,4-dimethoxyphenethyl)-5-hydroxy-4-(5-hydroxy-4-(1-methyl-1H-indol-5-yl)-4H-1,2,4-triazol-3-yl)phenyl dihydrogen phosphate |
| 4A | 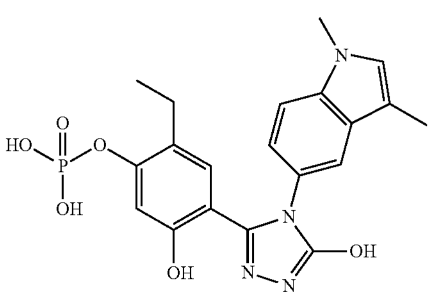 [SMILES: CCc1cc(-c2nnc(O)n2-c2ccc3c(c2)c(C)cn3C)c(O)cc1OP(=O)(O)O] | | 4-(4-(1,3-dimethyl-1H-indol-5-yl)-5-hydroxy-4H-1,2,4-triazol-3-yl)-2-ethyl-5-hydroxyphenyl dihydrogen phosphate |

The Hsp90 inhibitory compounds used in the disclosed methods can be prepared according to the procedures disclosed in U.S. Patent Publication No. 2006/0,167,070, and PCT Publication No. WO2009/023,211.

These triazolone compounds typically can form a tautomeric structure as shown below and as exemplified by the tautomeric structures shown in Tables 1 and 2:

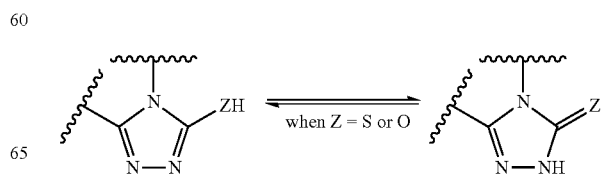

Other Hsp90 inhibitors include geldanamycin derivatives, e.g., a benzoquinone or hygroquinone ansamycin HSP90 inhibitor such as IPI-493 (CAS No. 64202-81-9) and/or IPI-504 (CAS No. 857402-63-2); 17-AAG CAS No. 75747-14-7), BIIB-021 (CNF-2024, CAS No. 848695-25-0), BIIB-028, AUY-922 (also known as VER-49009, CAS No. 747412-49-3), SNX-5422 (CAS No. 908115-27-5), AT-13387 (CAS No. 912999-49-6), XL-888, MPC-3100, CU-0305, 17-DMAG (CAS No. 467214-21-7), CNF-1010 (CAS No. 946090-39-7), Macbecin (e.g., Macbecin I (CAS No. 73341-72-7), Macbecin II (CAS No. 73341-73-8)), CCT-018159 (CAS No. 171009-07-7), CCT-129397 (CAS No. 940289-57-6), PU-H71 (CAS No. 873436-91-0), or PF-04928473 (SNX-2112, CAS No. 945626-71-1). These Hsp90 inhibitors may be used in the methods described herein.

The method described herein includes treating cancer in a subject, comprising administering to a subject an effective amount of an Hsp90 inhibitor according to formulae (I) or (Ia), or a compound in Tables 1 or 2, wherein the subject has cancer with a mutation in ALK. In one aspect, the method includes identifying a subject with cancer with a mutation in ALK and administering to the subject an effective amount of a compound of formulae (I) or (Ia), or a compound in Tables 1 or 2. In an embodiment, the Hsp90 inhibitor is ganetespib. In another embodiment, the Hsp90 inhibitor ganetespib is in combination with one or more additional therapeutic agents. In an embodiment, the Hsp90 inhibitor ganetespib is in combination with crizotinib. In an embodiment, the Hsp90 inhibitor is compound 1A. In another embodiment, the Hsp90 inhibitor compound 1A is in combination with one or more additional therapeutic agents. In another embodiment, the Hsp90 inhibitor compound IA is in combination with crizotinib.

In an embodiment, the method includes treating cancer in a subject, comprising administering to a subject an effective amount of an Hsp90 inhibitor according to formulae (I) or (Ia)), or a compound in Tables 1 or 2, wherein the subject has non-small cell lung cancer with a mutation in ALK. In one aspect, the method includes identifying a subject with non-small cell lung cancer with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating cancer in a subject, comprising administering to a subject an effective amount of an Hsp90 inhibitor according to formulae (I) or (Ia)), or a compound in Tables 1 or 2, wherein the subject has non-small cell lung cancer with a mutation in ALK. In one aspect, the method includes identifying a subject with non-small cell lung cancer with a mutation in ALK and administering to the subject an effective amount of a compound of formulae (I) or (Ia), or a compound in Tables 1 or 2. In an embodiment, the Hsp90 inhibitor compound 1A is in the amount from about 100 m g/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has an EML4-ALK translocation. In one aspect, the method includes identifying a subject with non-small cell lung cancer having an EML4-ALK translocation and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has an EML4-ALK translocation. In one aspect, the method includes identifying a subject with non-small cell lung cancer having an EML4-ALK translocation and administering to the subject an effective amount of a compound of formulae (I) or (Ia), or a compound in Tables 1 or 2. In an embodiment, the Hsp90 inhibitor compound 1A is in the amount from about 100 m g/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has an NPM-ALK translocation. In one aspect, the method includes identifying a subject with non-small cell lung cancer having an NPM-ALK translocation and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has an NPM-ALK translocation. In one aspect, the method includes identifying a subject with non-small cell lung cancer having an NPM-ALK translocation and administering to the subject an effective amount of a compound of formulae (I) or (Ia), or a compound in Tables 1 or 2. In an embodiment, the Hsp90 inhibitor compound 1A is in the amount from about 100 mg/m² to about 500 mg/m². In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating non-small cell lung cancer in a subject, comprising administering to a subject an effective amount of an Hsp90 inhibitor according to formulae (I) or (Ia), or a compound in Tables 1 or 2, wherein the non-small cell lung cancer has a KIF5B-ALK translocation. In one aspect, the method includes identifying a subject with non-small cell lung cancer having a KIF5B-ALK translocation and administering to the subject an effective amount of a compound of formulae (I) or (Ia), or a compound in Tables 1 or 2. In an embodiment, the Hsp90 inhibitor ganetespib is in the amount from about 100 mg/m² to about 500 mg/m². In an embodiment, the Hsp90 inhibitor ganetespib is in the amount of about 200 mg/m². In an embodiment, the Hsp90 inhibitor ganetespib is in the amount of about 150 mg/m². In an embodiment, the Hsp90 inhibitor ganetespib is administered at about 200 mg/m² once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has a KIF5B-ALK translocation. In one aspect, the method includes identifying a subject with non-small cell lung cancer having a KIF5B-ALK translocation and administering to the subject an effective amount of a compound of formulae (I) or (Ia), or a compound in Tables 1 or 2. In an embodiment, the Hsp90 inhibitor compound 1A is in the amount from about 100 m g/m² to about 500 mg/m². In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has a TFG-ALK translocation. In one aspect, the method includes identifying a subject with non-small cell lung cancer having a TFG-ALK translocation and administering to the subject an effective amount of a compound of formulae (I) or (Ia), or a compound in Tables 1 or 2. In an embodiment, the Hsp90 inhibitor ganetespib is in the amount from about 100 m g/m² to about 500 mg/m². In an embodiment, the Hsp90 inhibitor ganetespib is in the amount of about 200 mg/m². In an embodiment, the Hsp90 inhibitor ganetespib is in the amount of about 150 mg/m². In an embodiment, the Hsp90 inhibitor ganetespib is administered at about 200 mg/m² once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating non-small cell lung cancer in a subject, comprising administering to a subject an effective amount of an Hsp90 inhibitor according to formulae (I) or (Ia)), or a compound in Tables 1 or 2, wherein the non-small cell lung cancer has a TFG-ALK translocation. In one aspect, the method includes identifying a subject with non-small cell lung cancer having a TFG-ALK translocation and administering to the subject an effective amount of a compound of formulae (I) or (Ia), or a compound in Tables 1 or 2. In an embodiment, the Hsp90 inhibitor compound 1A is in the amount from about 100 m g/m² to about 500 mg/m². In another embodiment, the Hsp90 inhibitor compound 1A is in combination with one or more additional therapeutic agents. In another embodiment, the Hsp90 inhibitor compound 1A is in combination with crizotinib.

In one embodiment, the method includes treating diffuse large B-cell lymphoma (DLBCL) in a subject comprising administering to a subject an effective amount of an Hsp90 inhibitor according to formulae (I) or (Ia), or a compound in Tables 1 or 2, wherein the subject has DLBCL with a mutation in ALK. In one aspect, the method includes identifying a subject with DLBCL with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m² to about 500 mg/m². In an embodiment, the Hsp90 inhibitor ganetespib is in the amount of about 200 mg/m². In an embodiment, the Hsp90 inhibitor ganetespib is in the amount of about 150 mg/m². In an embodiment, the Hsp90 inhibitor ganetespib is administered at about 200 mg/m² once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating diffuse large B-cell lymphoma (DLBCL) in a subject comprising administering to a subject an effective amount of an Hsp90 inhibitor according to formulae (I) or (Ia), or a compound in Tables 1 or 2, wherein the subject has DLBCL with a mutation in ALK. In one aspect, the method includes identifying a subject with DLBCL with a mutation in ALK and administering to the subject an effective amount of a compound of formulae (I) or (Ia), or a compound in Tables 1 or 2. In an embodiment, the Hsp90 inhibitor compound 1A is in the amount from about 100 mg/m² to about 500 mg/m². In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating anaplastic large cell lymphoma (ALCL) in a subject comprising administering to a subject an effective amount of an Hsp90 inhibitor according to formulae (I) or (Ia), or a compound in Tables 1 or 2, wherein the subject has ALCL with a mutation in ALK. In one aspect, the method includes identifying a subject with ALCL with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m² to about 500 mg/m². In an embodiment, the Hsp90 inhibitor ganetespib is in the amount of about 200 mg/m². In an embodiment, the Hsp90 inhibitor ganetespib is in the amount of about 150 mg/m². In an embodiment, the Hsp90 inhibitor ganetespib is administered at about 200 mg/m² once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating anaplastic large cell lymphoma (ALCL) in a subject comprising administering to a subject an effective amount of an Hsp90 inhibitor according to formulae (I) or (Ia), or a compound in Tables 1 or 2, wherein the subject has ALCL with a mutation in ALK. In one aspect, the method includes identifying a subject with ALCL with a mutation in ALK and administering to the subject an effective amount of a compound of formulae (I) or (Ia), or a compound in Tables 1 or 2. In an embodiment, the Hsp90 inhibitor compound 1A is in the amount from about 100 mg/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating neuroblastoma (NBL) in a subject comprising administering to a subject an effective amount of an Hsp90 inhibitor according to formulae (I) or (Ia)), or a compound in Tables 1 or 2, wherein the subject has NBL with a mutation in ALK. In one aspect, the method includes identifying a subject with NBL with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating neuroblastoma (NBL) in a subject comprising administering to a subject an effective amount of an Hsp90 inhibitor according to formulae (I) or (Ia)), or a compound in Tables 1 or 2, wherein the subject has NBL with a mutation in ALK. In one aspect, the method includes identifying a subject with NBL with a mutation in ALK and administering to the subject an effective amount of a compound of formulae (I) or (Ia), or a compound in Tables 1 or 2. In an embodiment, the Hsp90 inhibitor compound 1A is in the amount from about 100 mg/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating inflammatory myofibroblastic tumors (IMT) in a subject comprising administering to a subject an effective amount of an Hsp90 inhibitor according to formulae (I) or (Ia), or a compound in Tables 1 or 2, wherein the subject has IMT with a mutation in ALK. In one aspect, the method includes identifying a subject with IMT with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating inflammatory myofibroblastic tumors (IMT) in a subject comprising administering to a subject an effective amount of an Hsp90 inhibitor according to formulae (I) or (Ia), or a compound in Tables 1 or 2, wherein the subject has IMT with a mutation in ALK. In one aspect, the method includes identifying a subject with IMT with a mutation in ALK and administering to the subject an effective amount of a compound of formulae (I) or (Ia), or a compound in Tables 1 or 2. In one embodiment, the Hsp90 inhibitor compound 1A is in the amount from about 100 mg/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating non-Hodgkin's lymphoma (NHL) in a subject comprising administering to a subject an effective amount of an Hsp90 inhibitor according to formulae (I) or (Ia), or a compound in Tables 1 or 2, wherein the subject has NHL with a mutation in ALK. In one aspect, the method includes identifying a subject with NHL with a mutation in ALK and administering to the subject an effective amount of a compound of formulae (I) or (Ia), or a compound in Tables 1 or 2. In an embodiment, the Hsp90 inhibitor ganetespib is in the amount from about 100 m g/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating non-Hodgkin's lymphoma (NHL) in a subject comprising administering to a subject an effective amount of an Hsp90 inhibitor according to formulae (I) or (Ia), or a compound in Tables 1 or 2, wherein the subject has NHL with a mutation in ALK. In one aspect, the method includes identifying a subject with NHL with a mutation in ALK and administering to the subject an effective amount of a compound of formulae (I) or (Ia), or a compound in Tables 1 or 2. In an embodiment, the Hsp90 inhibitor compound 1A is in the amount from about 100 mg/m$^2$ to about 500 mg/m$^2$. In another embodiment, the Hsp90 inhibitor compound 1A is in combination with one or more additional therapeutic agents. In another embodiment, the Hsp90 inhibitor compound 1A is in combination with crizotinib.

In an embodiment, the method includes treating esophageal squamous cell carcinoma (ESCC) in a subject comprising administering to a subject an effective amount of an Hsp90 inhibitor according to formulae (I) or (Ia), or a compound in Tables 1 or 2, wherein the subject has ESCC with a mutation in ALK. In one aspect, the method includes identifying a subject with ESCC with a mutation in ALK and administering to the subject an effective amount of a compound of formulae (I) or (Ia), or a compound in Tables 1 or 2. In an embodiment, the Hsp90 inhibitor ganetespib is in the amount from about 100 mg/m$^2$ to about 500 mg/m$^2$. In an embodiment, the Hsp90 inhibitor ganetespib is in the amount of about 200 mg/m$^2$. In an embodiment, the Hsp90 inhibitor ganetespib is in the amount of about 150 mg/m$^2$. In an embodiment, the Hsp90 inhibitor ganetespib is administered at about 200 mg/m$^2$ once weekly. In another embodiment, the Hsp90 inhibitor ganetespib is in combination with one or more additional therapeutic agents. In an embodiment, the Hsp90 inhibitor ganetespib is in combination with crizotinib.

In an embodiment, the method includes treating esophageal squamous cell carcinoma (ESCC) in a subject comprising administering to a subject an effective amount of an Hsp90 inhibitor according to formulae (I) or (Ia), or a compound in Tables 1 or 2, wherein the subject has ESCC with a mutation in ALK. In one aspect, the method includes identifying a subject with ESCC with a mutation in ALK and administering to the subject an effective amount of a compound of formulae (I) or (Ia), or a compound in Tables 1 or 2. In an embodiment, the Hsp90 inhibitor compound 1A is in the amount from about 100 mg/m² to about 500 mg/m². In another embodiment, the Hsp90 inhibitor compound 1A is in combination with one or more additional therapeutic agents. In another embodiment, the Hsp90 inhibitor compound 1A is in combination with crizotinib.

In one aspect, the method also includes treating cancer in a subject wherein the cancer has been previously treated with an ALK inhibitor and is no longer responsive to the earlier treatment (resistant to the treatment). In an embodiment, the ALK inhibitor may be crizotinib, LDK-378, AF-802, or ASP-3026. In an embodiment, the ALK inhibitor is crizotinib.

In an embodiment, the method includes treating NSCLC in a patient wherein the patient has been previously treated with an ALK inhibitor and is not responsive to the earlier treatment (resistant to further ALK inhibitor treatment) by administering an amount of from about 100 mg/m² to about 500 mg/m² of ganetespib. In one embodiment, the ALK inhibitor may be crizotinib, LDK-378, AF-802, or ASP-3026. In one embodiment, the ALK inhibitor is crizotinib.

In an embodiment, the method includes treating NSCLC in a patient wherein the patient has been previously treated with an ALK inhibitor and is no longer responsive to the earlier treatment (resistant to further ALK inhibitor treatment) by administering an amount of from about 100 mg/m² to about 500 mg/m² of compound 1A. In one embodiment, the ALK inhibitor may be crizotinib, LDK-378, AF-802, or ASP-3026. In one embodiment, the ALK inhibitor is crizotinib.

In an embodiment, the method also treating cancer in a subject comprising administering to a subject an effective amount of an Hsp90 inhibitor according to formulae (I) or (Ia) or a compound in Tables 1 or 2, in combination with crizotinib, wherein the subject has cancer with a c-MET mutation. In an embodiment, the Hsp90 inhibitor is ganetespib in combination with crizotinib. In an embodiment, the Hsp90 inhibitor is compound 1A in combination with crizotinib. In an embodiment, the cancer is non-small cell lung cancer with a c-MET mutation. In an embodiment, the cancer is breast cancer with a c-MET mutation. In an embodiment, the cancer is prostate cancer with a c-MET mutation. In an embodiment, the cancer is pancreatic cancer with a c-MET mutation.

In general, the recommended daily dose range of a triazolone compound described herein for the conditions described herein lie within the range of from about 0.01 mg to about 1000 mg per day, given as a single once-a-day dose preferably as divided doses throughout a day. In one embodiment, the daily dose is administered twice daily in equally divided doses. Specifically, a daily dose range should be from about 5 mg to about 500 mg per day, more specifically, between about 10 mg and about 200 mg per day. In managing the patient, the therapy should be initiated at a lower dose, perhaps about 1 mg to about 25 mg, and increased if necessary up to about 200 mg to about 1000 mg per day as either a single dose or divided doses, depending on the patient's global response. It may be necessary to use dosages of the active ingredient outside the ranges disclosed herein in some cases, as will be apparent to those of ordinary skill in the art. Furthermore, it is noted that the clinician or treating physician will know how and when to interrupt, adjust, or terminate therapy in conjunction with individual patient response.

Different therapeutically effective amounts may be applicable for different cancers, as will be readily known by those of ordinary skill in the art. Similarly, amounts sufficient to prevent, manage, treat or ameliorate such cancers, but insufficient to cause, or sufficient to reduce, adverse effects associated with the triazolone compounds described herein are also encompassed by the above described dosage amounts and dose frequency schedules. Further, when a patient is administered multiple dosages of a triazolone compound described herein, not all of the dosages need be the same. For example, the dosage administered to the patient may be increased to improve the prophylactic or therapeutic effect of the compound or it may be decreased to reduce one or more side effects that a particular patient is experiencing.

In specific embodiment, the amount of a compound of formulae (I) or (Ia), or a compound in Tables 1 or 2, administered is from about 2 mg/m² to about 500 mg/m², for example, from about 100 mg/m² to about 500 mg/m², from about 125 mg/m² to about 500 mg/m², from about 150 m g/m² to about 500 mg/m² or from about 175 mg/m² to about 500 mg/m². In one embodiment, the amount of the compound of formulae (I) or (Ia), or a compound in Tables 1 or 2 administered is about 100 mg/m² to about 300 mg/m², from about 125 mg/m² to about 300 mg/m², from about 150 mg/m² to about 300 mg/m² or from about 175 mg/m² to about 300 mg/m². In some embodiments, the amount of the compound of formulae (I) or (Ia), or a compound if Tables 1 or 2 administered is about 2 mg/m², 4 mg/m², about 7 mg/m², about 10 mg/m², about 14 mg/m², about 19 mg/m², about 23 mg/m², about 25 mg/m², about 33 mg/m², about 35 mg/m², about 40 mg/m², about 48 mg/m², about 49 mg/m², about 50 mg/m², about 65 mg/m², about 75 mg/m², about 86 mg/m², about 100 mg/m², about 110 mg/m², about 114 mg/m², about 120 mg/m², about 144 mg/m², about 150 mg/m², about 173 mg/m², about 180 mg/m², about 200 mg/m², about 216 mg/m² or about 259 mg/m². The compound of formulae (I) or (Ia) or in Tables 1 or 2, can be administered 1, 2, 3, 4 or more times daily, or once every 2, 3, 4, 5, 6 or 7 days, or once weekly, once every two weeks, once every three weeks or once monthly.

In certain embodiments, one or more compounds described herein and one or more other the therapies (e.g., therapeutic agents) are cyclically administered. Cycling therapy involves the administration of a first therapy (e.g., a first prophylactic or therapeutic agents) for a period of time, followed by the administration of a second therapy (e.g., a second prophylactic or therapeutic agents) for a period of time, followed by the administration of a third therapy (e.g., a third prophylactic or therapeutic agents) for a period of time and so forth, and repeating this sequential administration, i.e., the cycle in order to reduce the development of resistance to one of the agents, to avoid or reduce the side effects of one of the agents, and/or to improve the efficacy of the treatment.

In certain embodiments, administration of the same compound described herein may be repeated and the administrations may be separated by at least 1 day, 2 days, 3 days, 5 days, 10 days, 15 days, 30 days, 45 days, 2 months, 75 days, 3 months, or 6 months. In other embodiments, administration of the same prophylactic or therapeutic agent may be repeated and the administration may be separated by at least at least 1 day, 2 days, 3 days, 5 days, 10 days, 15 days, 30 days, 45 days, 2 months, 75 days, 3 months, or 6 months.

In a specific embodiment, the method includes preventing, treating, managing, or ameliorating a proliferative disorders, such as cancer, or one or more symptoms thereof, comprising administering to a subject in need thereof a dose of at least 150 µg/kg, preferably at least 250 µg/kg, at least 500 µg/kg, at least 1 mg/kg, at least 5 mg/kg, at least 10 mg/kg, at least 25 mg/kg, at least 50 mg/kg, at least 75 mg/kg, at least 100 mg/kg, at least 125 mg/kg, at least 150 mg/kg, or at least 200 mg/kg or more of one or more compounds described herein once every day, preferably, once every 2 days, once every 3 days, once every 4 days, once every 5 days, once every 6 days, once every 7 days, once every 8 days, once every 10 days, once every two weeks, once every three weeks, or once a month. Alternatively, the dose can be divided into portions (typically equal portions) administered two, three, four or more times a day.

The invention can be understood more fully by reference to the following detailed description and illustrative examples, which are intended to exemplify non-limiting embodiments of the invention.

EXAMPLES

Example 1

Of 23 patients in a Phase 2 trial tested for ALK translocation or rearrangement (ALK+), eight patients were ALK+ in at least one assay. Six of these eight patients (75%) showed tumor shrinkage in target lesions, one patient showed no change in tumor size, and one patient achieved stable disease (tumor growth <20%). The disease control rate in this population was 7/8 (88%), and the objective response rate (CR+PR) was 4/8 (50%). See FIG. 1.

This Phase 2 NSCLC trial was designed to enroll patients with advanced, metastatic disease (Stage IIIB and IV) who had failed prior therapy. Patients were grouped into one of three cohorts based on the genetic profile of their cancer—(A) EGFR mutation, (B) KRAS mutation, (C) neither EGFR nor KRAS mutation—and were treated with Compound 1, as a monotherapy, once-weekly at a dose of 200 mg/m². Based on initial encouraging signs of activity, the trial was expanded with two additional patient cohorts, including a cohort which allowed for combination treatment with ganetespib and docetaxel.

Approximately 45,000 patients each year are believed to develop advanced lung cancer with an ALK rearrangement. In clinical trials to date, patients treated with crizotinib have experienced disease progression after a median of 10 months. There is a clear medical need for a drug active in ALK+ NSCLC patients following crizotinib treatment failure.

Example 2

Case Study—Crizotinib Refractory Patient

Figure 2:
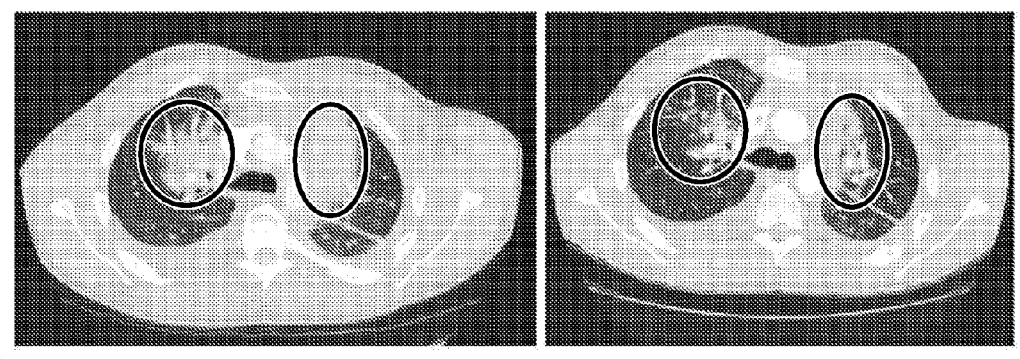
FIG. 2 depicts lung photographs of a 24 year old male with NSCLC, who was diagnosed, and treated with pemetrexed/cisplatinum with pemetrexed maintenance for thirteen months. The patient was EML4-ALK positive and previously on crizotinib for approximately 1 year. The picture on the left was taken on before commencing treatment with ganetespib. Treatment of ganetespib was initiated nine days later. The picture on the right was taken thirty-one days after the picture on the left.
Figure 3:
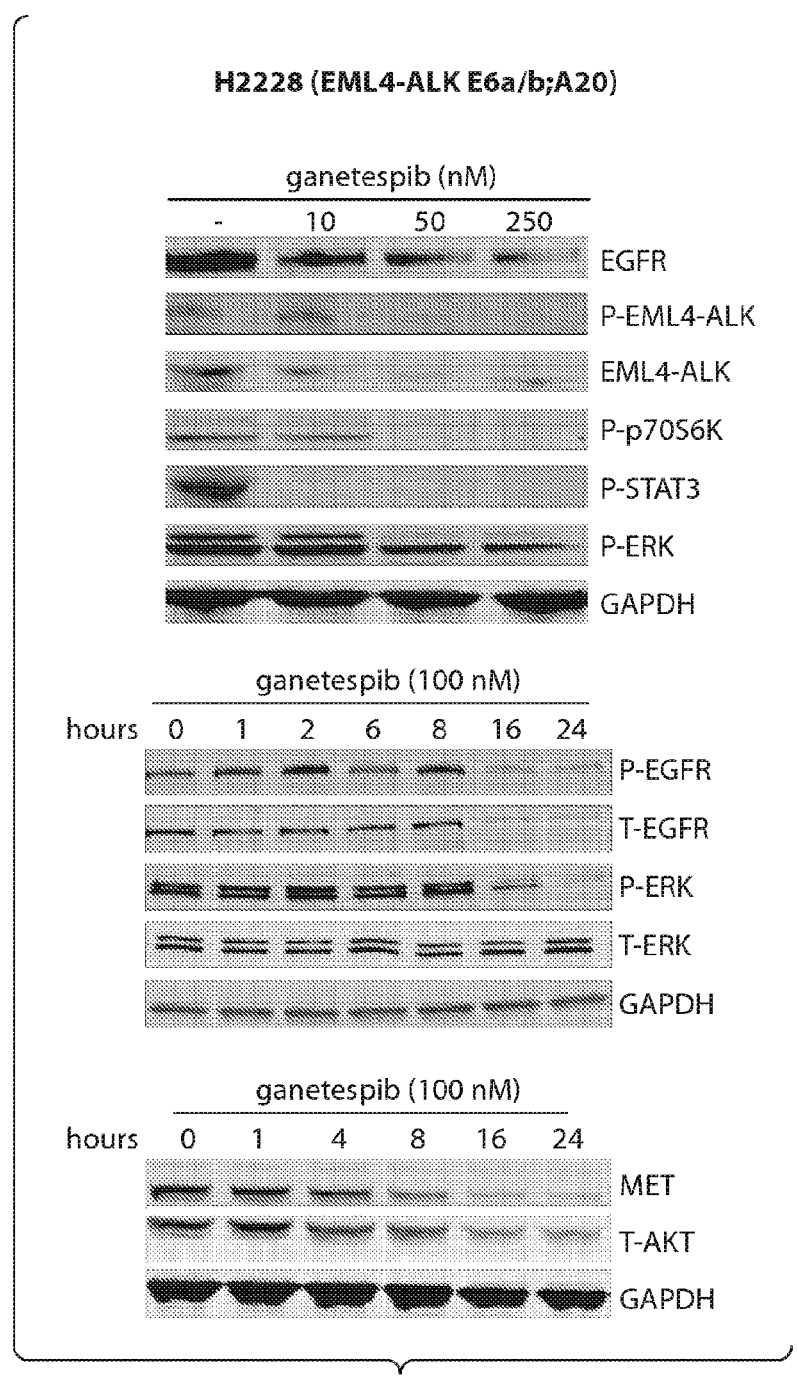
FIG. 3 displays SDS-PAGE images illustrating Hsp90 inhibition (24 hr) by ganetespib, leading to destabilization of EML4-ALK and abrogating several nodes of oncogenic signaling in H2228 NSCLC cells. H2228 cells were plated in 6-well plates at a density of 300,000 cells per well. Twenty four hours later, cells were dosed as shown with ganetespib, crizotinib or vehicle then disrupted in lysis buffer (CST) after the indicated period of time. Equivalent amounts of protein were resolved by SDS-PAGE followed by western blot analysis of signaling proteins.

FIG. 2 shows the treatment of a 24 year old male with NSCLC, who was diagnosed, and treated with pemetrexed/cisplatinum with pemetrexed maintenance for thirteen months. The patient was EML4-ALK positive and previously on crizotinib for approximately 1 year. A re-biopsy of the patient showed resistance mutation to crizotinib. The picture on the left was taken on before commencing treatment with ganetespib. Treatment of ganetespib was initiated nine days later. The picture on the right, showing visible and significant tumor shrinkage, was taken thirty-one days after the picture on the left, after three weeks of once-weekly injections of ganetespib.

Example 3

Materials and Methods

All tumor cell lines were obtained from the American Type Culture Collection (ATCC, Manassas, Va.) and maintained according to the suppliers' instructions. The ATCC cell lines were authenticated by the routine ATCC Cell Biology Program using short tandem repeat (STR) analysis (DNA profiling) and were used within 6 months of receipt for this study. Crizotinib (PF-02341066) was synthesized by the Medicinal Chemistry Core Facility, Department of Chemical Biology & Therapeutics, St. Jude Children's Research Hospital; ganetespib (STA-9090) was prepared by Synta Pharmaceuticals. Both compounds were dissolved in dimethyl sulfoxide (DMSO) to yield stock solutions of 10 mM and stored at −80° C. until their use in cell culture. BaF3 engineered to stably express NPM-ALK were used for inhibitor-resistance selection. Screening for inhibitor-resistant colonies was performed using a previously published protocol that employs continual exposure of kinase-dependent cells to various concentrations of an inhibitor until resistant cells emerge. No chemical mutagenesis to accelerate the emergence of resistant clones (e.g., with ENU) was performed. Limiting dilution was done to isolate clonally derived crizotinib-resistant NPM-ALK/BaF3 lines, and sequence analysis of the ALK KD was then performed to identify the inhibitor-resistance mutations. Cytotoxic $IC_{50}$ determinations were performed by XTT assay following 72-hr incubations with crizotinib on several NPM-ALK/BaF3 clones containing each of the identified inhibitor-resistance mutations. Each putative resistance mutation was confirmed to confer crizotinib resistance by engineering it into the NPM-ALK cDNA, generating clonal NPM-ALK/BaF3 cell lines expressing the mutation, and determining the cytotoxic $IC_{50}$ of the inhibitor against the clonal lines. Cytotoxic $IC_{50}$ values for ganetespib against crizotinib-resistant NPM-ALK/BaF3 cells were determined by XTT assay following 72-hr incubations with a range of compound concentrations. Immunoblotting to assess the degradation of NPM-ALK in response to ganetespib was performed with the ALK 11 rabbit polyclonal anti-serum at a dilution of 1:2000.

As for in vivo xenograft tumor models, female BALB/c, immunodeficient BALB/c nude and CB-17/Icr-Prkdcscid/Crl (SCID) mice (Charles River Laboratories, Wilmington, Mass.) at 7-12 weeks of age were maintained in a pathogen-free environment and all in vivo procedures were approved by the Synta Pharmaceuticals Corp. Statistical analyses were performed using a Kruskal-Wallace one-way ANOVA on ranks followed by the Tukey test.

H2228 and H3122 NSCLC cells, which express EML4-ALK, were treated with ganetespib, crizotinib or the combination, and cell viability and signaling cascades were assessed both in vitro and in vivo. To generate models of crizotinib resistance, H2228 NSCLC, H3122 NSCLC and NPM-ALK-expressing BaF3 cells were exposed to various crizotinib concentrations. Fifteen different ALK kinase domain substitutions were identified in the BaF3 cells; clonal NPM-ALK/BaF3 cells were made for each resistance mutation and assayed for sensitivity to ganetespib.

Figure 5:
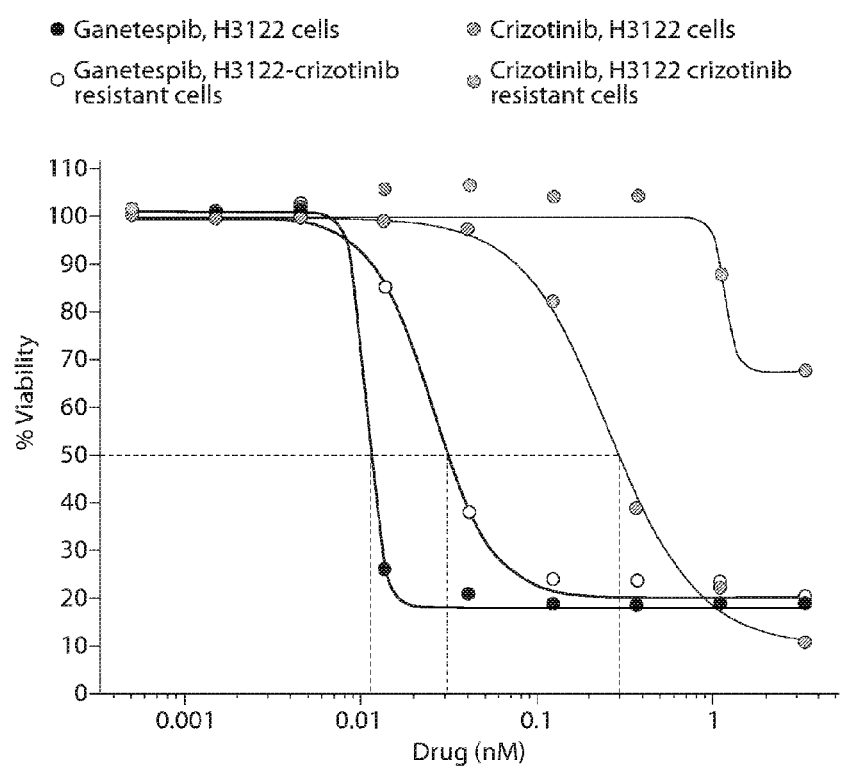
FIG. 5 illustrates the utility of long term crizotinib treatment in promoting crizotinib resistance, and the comparable activity of ganetespib in crizotinib-sensitive and crizotinib-resistant H3122 cells.
Figure 6:
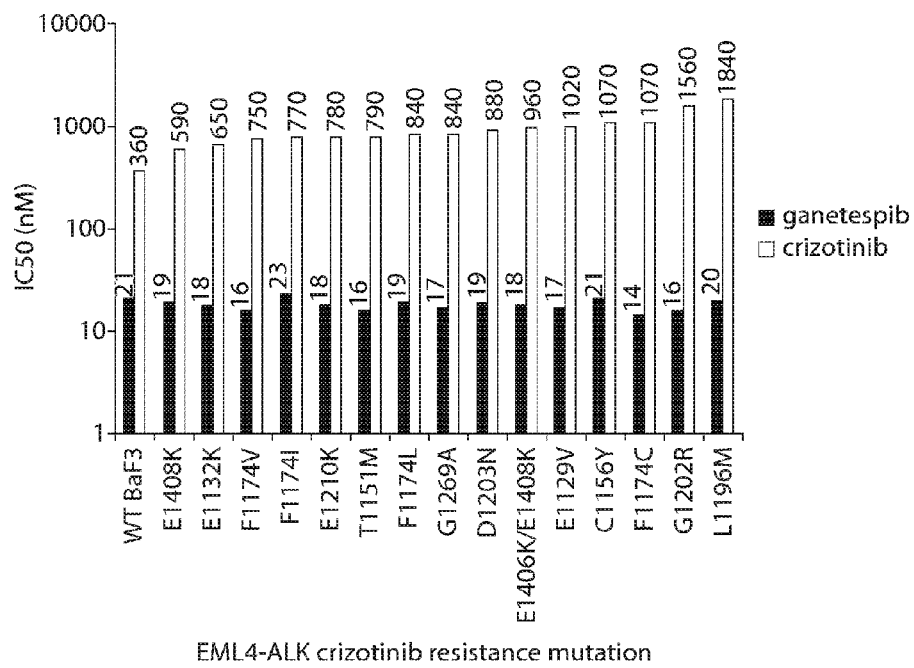
FIG. 6 is a graph illustrating the results of an assessment of ganetespib activity in crizotinib-sensitive NPM-ALK Ba/F3 cells and crizotinib-resistant NPM-ALK mutants.
Figure 7:
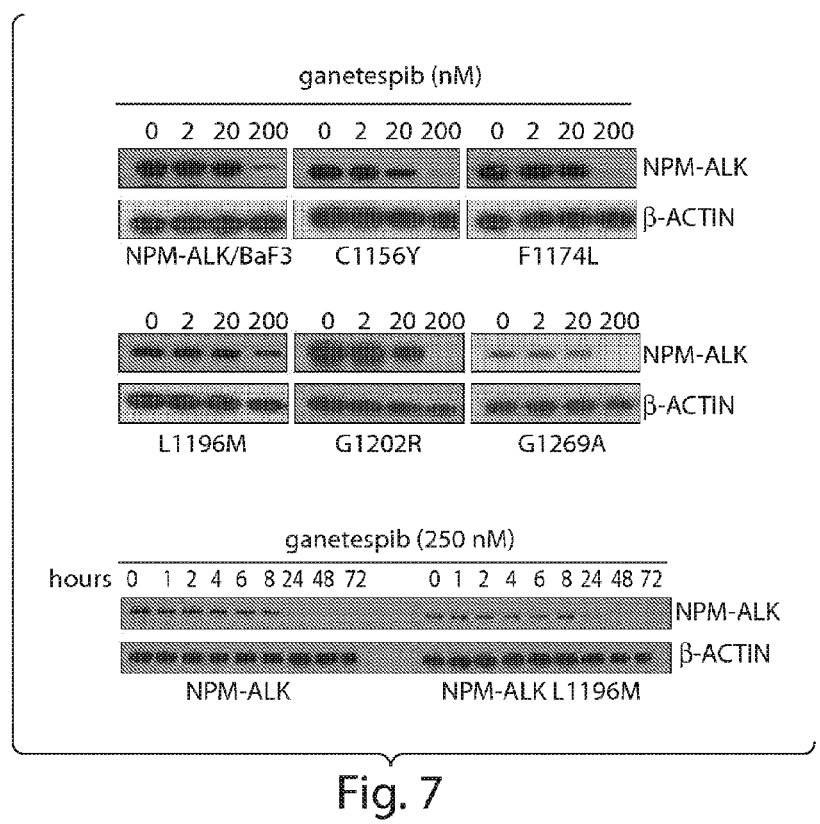
FIG. 7 shows SDS-PAGE images illustrating a concentration and time dependent depletion of NPM-ALK and mutant NPM-ALK in cell lines that were treated with ganetespib.

To generate crizotinib resistance, H3122 cells were grown to ~70% confluence in a 175 cm² flask. Then, criztoinib was added to a final concentration of 1 µM. Cells were maintained in 1 µM crizotinib and drug-containing media was changed every 3 days. Within 4 weeks, cells began to proliferate in the presence of crizotinib and were passaged once they reached confluence. This population of crizotinib resistant cells was propagated in growth media containing 1 µM crizotinib. H3122 parental and crizotinib resistant cells were plated in 96 well plates at a density of 7500 cells per well. Twenty-four hours after plating, cells were dosed with graded concentrations of ganetespib or crizotinib for 72 hours. Viability was measured by Cell Titer Glo assay (Promega) (FIG. 5)

Results:

Ganetespib was significantly more potent than crizotinib in both H2228 and H3122 NSCLC cells. The combination of ganetespib with crizotinib resulted in complimentary inhibition of MAPK signaling and strong synergistic anticancer activity in vitro and in vivo. In crizotinib resistant H2228 and H3122 cells, ganetespib displayed low nanomolar activity equivalent to that observed in the parental population. Ganetespib treatment induced the degradation of wild type and all 15 mutant forms of ALK, resulting in potent cell death.

Further biological studies as illustrated in FIG. 3 through FIG. 20 also demonstrated the efficacy of ganetespib in treating cancer with an ALK mutation. Some of these Figures are described in additional detail below.

Figure 4:
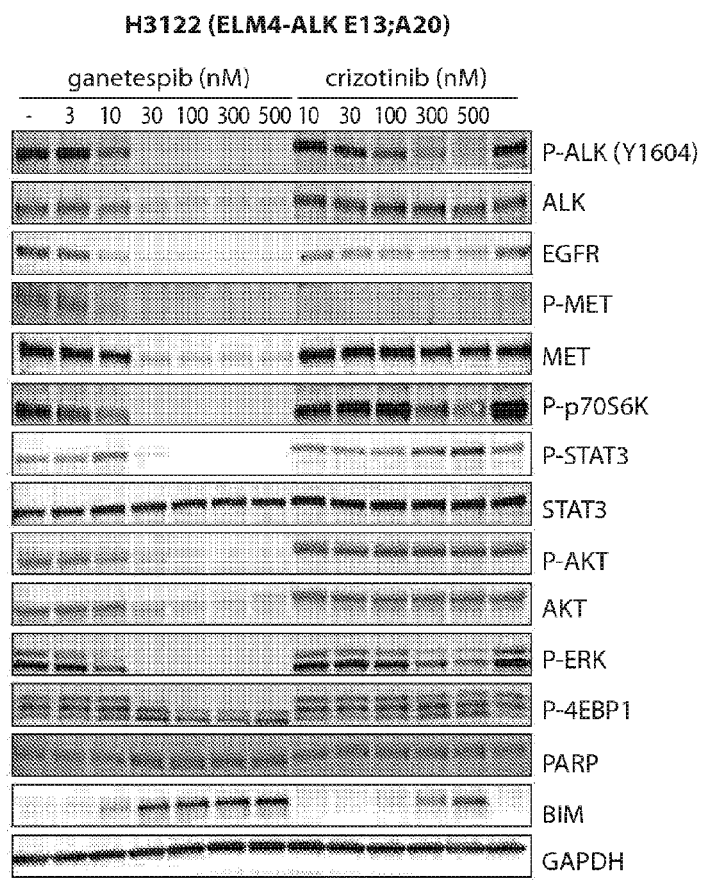
FIG. 4 demonstrates the higher potency of ganetespib compared to crizotinib at deactivating EML4-ALK and inducing apoptosis in H3122 NSCLC cells. H3122 cells were plated in 6 well plates at a density of 300,000 cells per well. Twenty four hours later, cells were dosed as shown with ganetespib, crizotinib or vehicle, then were disrupted in lysis buffer (CST) after the indicated period of time. Equivalent amounts of protein were resolved by SDS-PAGE followed by western blot analysis of signaling proteins.

FIGS. 4 and 5 demonstrated the comparative effects of ganetespib and crizotinib in the ALK-driven H3122 cell line, which is dependent on the E13;A20 fusion protein for growth and survival. Ganetespib was acutely cytotoxic to these cells, and with almost 50 times greater potency than crizotinib (3.2 vs. 156 nM). When expression changes in client proteins and signaling pathways were examined in this line, it was found that ganetespib exposure at concentrations 30 nM resulted in the complete loss of phosphorylated EML4-ALK protein expression, as well as the active (phosphorylated) forms of STAT3, AKT and ERK. Targeted degradation of EGFR and MET were seen at the same concentrations, as well as negative effects on the mTOR signaling pathway, as evidenced by loss of p-p70S6K and p-4E-BP1 expression (FIG. 4). Consistent with the potent cytotoxic activity of the compound, a robust increase in BIM and cleaved PARP expression were observed. In contrast, crizotinib displayed far weaker activity in terms of effector signaling and activation of apoptotic pathways. At least a ten-fold higher concentration of crizotinib (300 nM) was required to significantly reduce phosphorylated EML4-ALK levels, and this was not complete until 500 nM. These same maximal concentrations only achieved relatively modest effects compared to ganetespib on the blockade of downstream ERK, AKT and mTOR signaling, as well as apoptotic induction. Taken together, these data showed that ganetespib displays greater in vitro potency than crizotinib in ALK+NSCLC cells.

Figure 8:
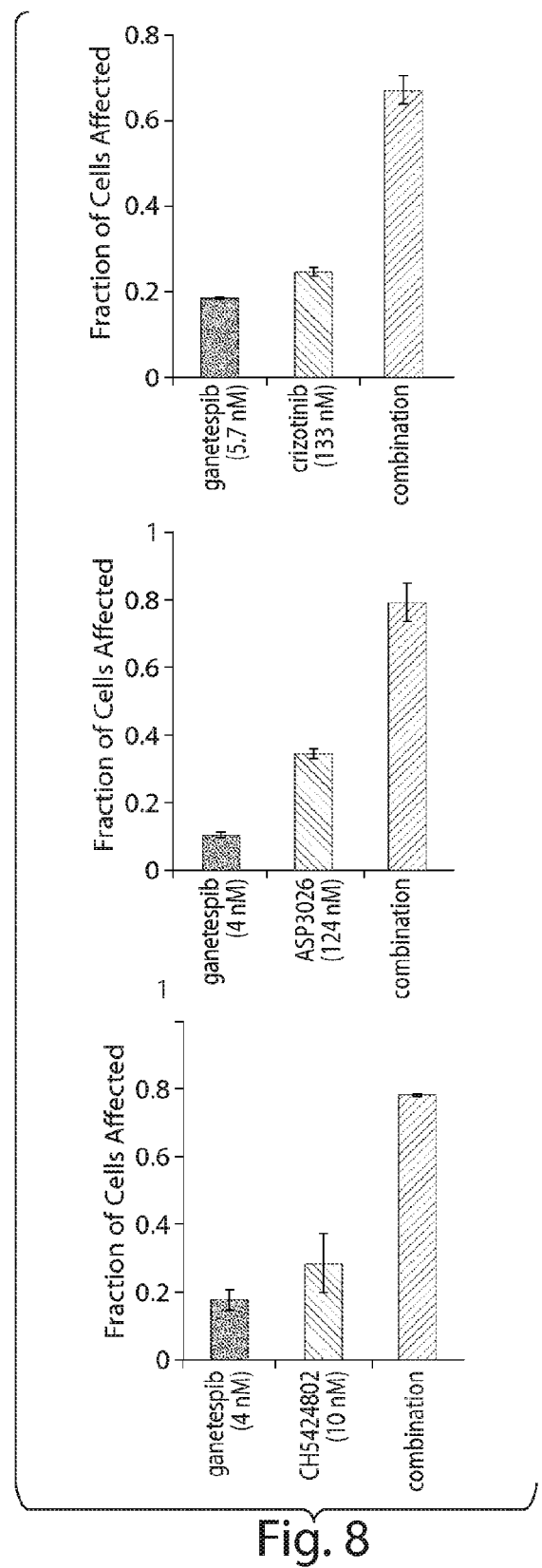
FIG. 8 displays graphs comparing activities of ganetespib in combination with ALK inhibitors in vitro and in vivo., H3122 cells were treated with the indicated concentrations of ganetespib, crizotinib, ASP3026, CH5424802 either as single agents or in combination. Cell viability was determined at 72 h. H3122 cells were seeded in 96 well plates at a density of 7500 cells per well. Ganetespib and crizotinib were dosed at several concentration ratios, and viability was measured after 72 h by Cell Titer Glo assay (CST).

As shown in FIG. 8, concurrent administration of low ($IC_{20}$) doses of ganetespib and crizotinib to H3122 cells substantially increased cell death in H3122 cells in vitro. Importantly, similar combinatorial benefit was observed when ganetespib was dosed in combination with the structurally unrelated ALK inhibitors ASP3026 and $CH_{542802}$.

Figure 9:
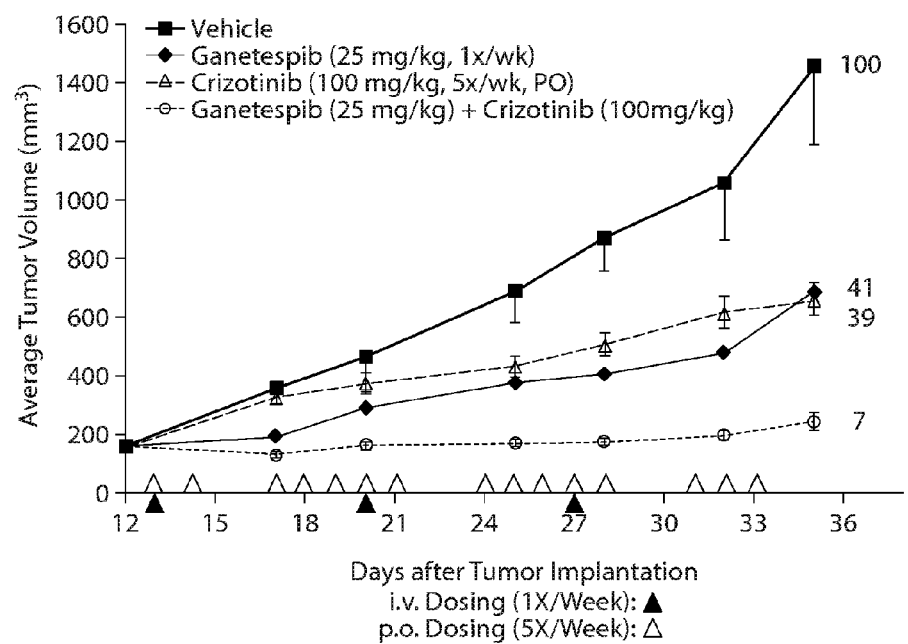
FIG. 9 is a graph comparing the activity of crizotinib (MTD), ganetespib (⅙ MTD) as monotherapy and in combination in H3122 mouse xenografts. H3122 cells were subcutaneously implanted (7.5×10$^6$ cells per mouse) into Female C.B17 SCID mice. Mice bearing established tumors (~160mm$^3$) were intravenously dosed with ganetespib (25 mg/kg, 1×/week) and crizotinib (100 mg/kg, 5×/week) alone or in combination for 5 weeks. Tumor volume was measured twice weekly to assess the level of growth inhibition.
Figure 10:
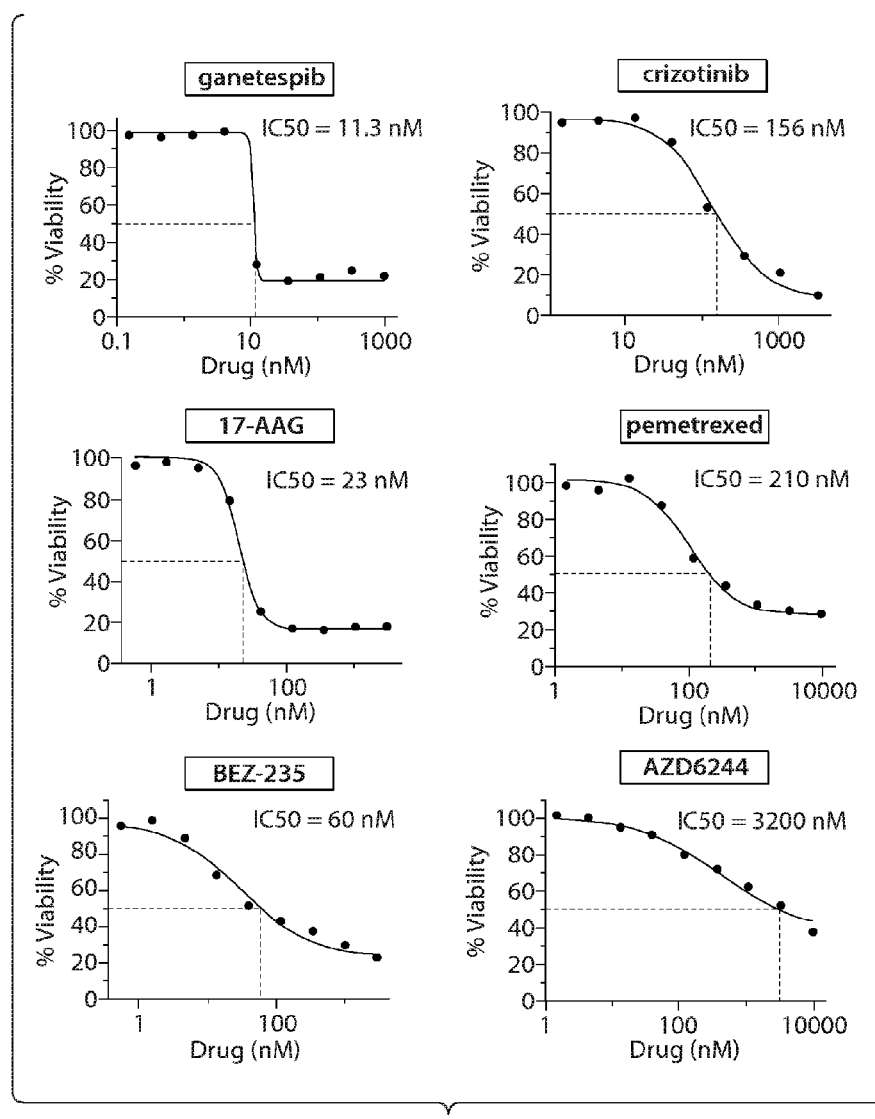
FIG. 10 displays graphs comparing the efficacy of ganetespib, crizotinib, 17-AAG, pemetrexed, BEZ-235, AZD6244 and vehicle in inhibiting the viability of H3122 NSCLC cells, and shows that ganetespib is 2-300× more potent compared to these other anticancer agents used in treating NSCLC. H3122 cells were cultured in RPMI-1640 supplemented with 10% FBS. Cells were seeded in 96 well plates at a density of 7500 cells per well. Twenty-four hours after plating, cells were dosed with graded concentrations of drug or vehicle for 72 hours. Viability was measured by the Cell Titer Glo assay (Promega).

As shown in FIG. 9, once weekly administration of ganetespib at 25 mg/kg was comparable to 5×/week dosing of crizotinib at its MTD, with each compound inducing a similar degree of tumor suppression (T/C values of 41% and 39%, respectively). Consistent with the in vitro findings, concurrent treatment with both drugs resulted in a significant enhancement of antitumor activity, inhibiting tumor growth by 93%. Therefore, the effects on cell viability seen in vitro also showed efficacy in vivo in xenograft-bearing mice with ganetespib both as a single agent and in combination. In addition, combination treatment was well-tolerated, with no significant changes in body weights seen after 3 weeks of treatment. Thus, ganetespib and crizotinib, when combined, displayed better antitumor efficacy compared to monotherapy in H3122 ALK+NSCLC xenografts.

Figure 11:
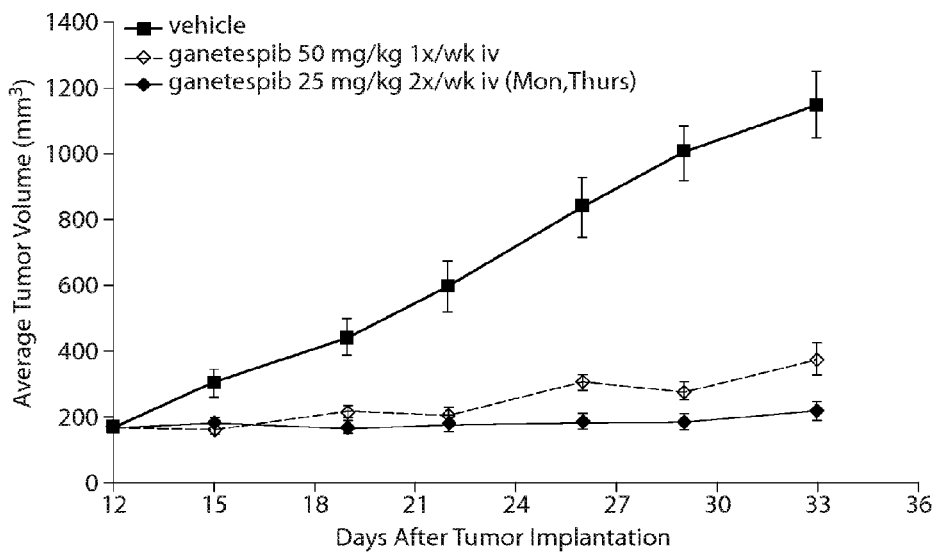
FIG. 11 is a graph showing how ganetespib inhibited tumor progression in H3122 ALK+NSCLC xenografts.
Figure 12:
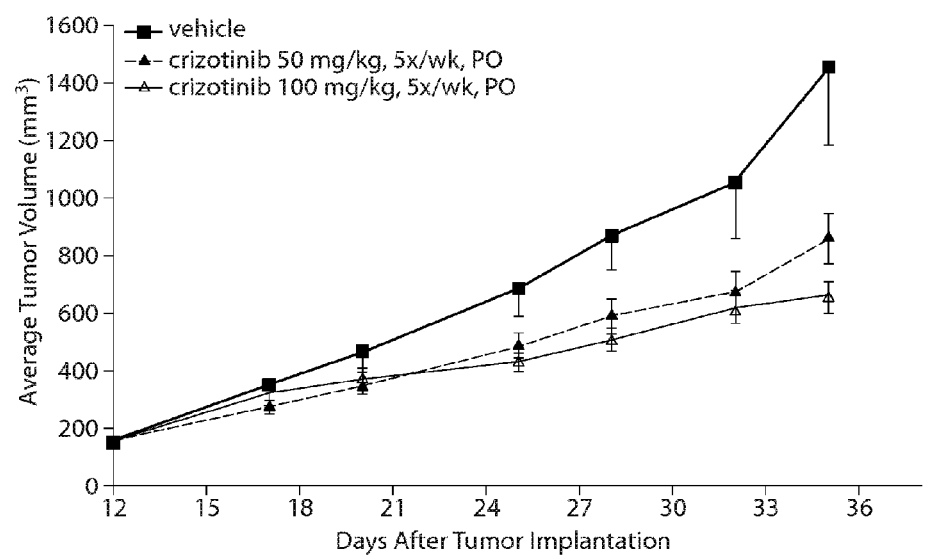
FIG. 12 is a graph showing the result of crizotinib treatment, at two doses, of H3122 ALK+NSCLC xenografts.
Figure 13:
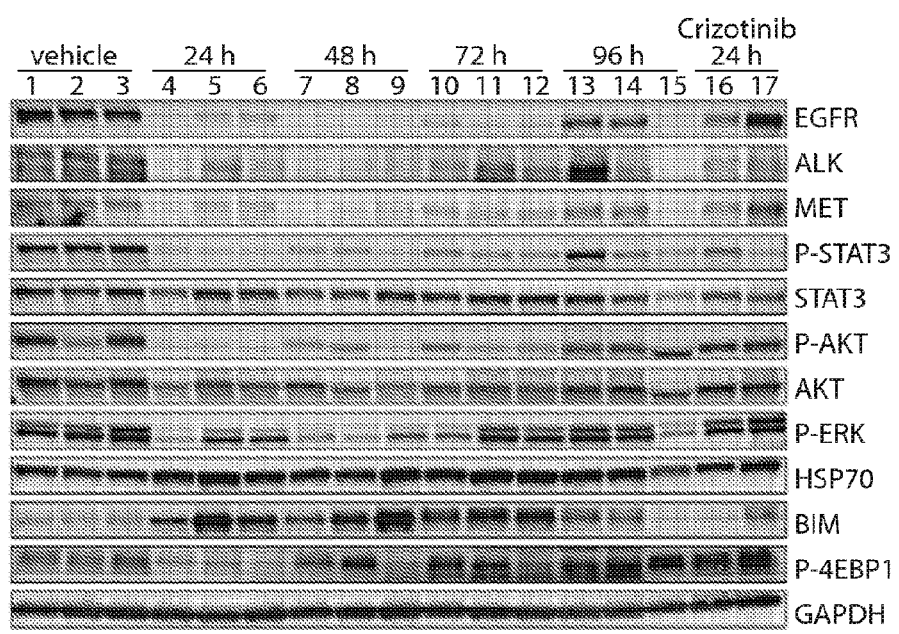
FIG. 13 shows SDS-PAGE images comparing ganetespib (100 mpk) against vehicle and crizotinib depleted EML4-ALK and blocked oncogenic signaling pathways for up to 4 days in H3122 xenografts.

FIGS. 11 and 12 further demonstrate the antitumor activity of ganetespib and crizotinib in vivo in tumor-bearing SCID mice. Animals bearing H3122 xenografts were dosed intravenously (i.v.) with ganetespib at 50 mg/kg once a week (FIG. 11). This regimen resulted in significant tumor growth inhibition (T/C value 21%) over a 3 week period. Splitting the dose into two consecutive day dosing of 25 mg/kg each week resulted in a minor improvement in efficacy (T/C value 10%) and disease stabilization (FIG. 11.) Importantly, both treatment regimens were well-tolerated, with no toxicity or changes in body weight seen after 3 weeks of dosing. In contrast, crizotinib was less efficacious in the same model. As shown in FIG. 12, 5×/week p.o. dosing of crizotinib at 50 mg/kg resulted in a T/C value of only 55%. When the crizotinib dose was doubled to 100 mg/kg significant losses of body weight were more frequently observed. FIG. 13 illustrated pharmacodynamic analysis performed in additional mice bearing H3122 xenografts in an effort to determine whether these tumor responses correlated with target modulation in vivo. Animals were treated with a single bolus injection of ganetespib at the effective 50 mg/kg dose and tumors harvested at 24, 48, 72 and 96 h. For comparison, animals were treated with a single injection of vehicle or crizotinib at 50 mg/kg and tumors collected 24 h later. EML4-ALK and downstream ERK signaling were degraded and deactivated, respectively, within 24 h following ganetespib treatment. Importantly, these effects were sustained over time, as recovery did not occur until 72 h. Similar kinetics were observed for the targeted destabilization of the Hsp90 clients EGFR and MET, as well as their effector signaling intermediates p-STAT3 and p-AKT. Loss of these signaling cascades was associated with a corresponding increase in BIM protein expression, indicative of intratumoral apoptotic induction. In contrast, single dose crizotinib had negligible effects on ERK activity at 24 h, nor any of the other cascades. Overall, these data show that single dose ganetespib exerts durable suppressive effects on ALK signaling in human tumor xenografts, destabilizing both the fusion kinase and its effectors for up to 72 h.

Figure 14:
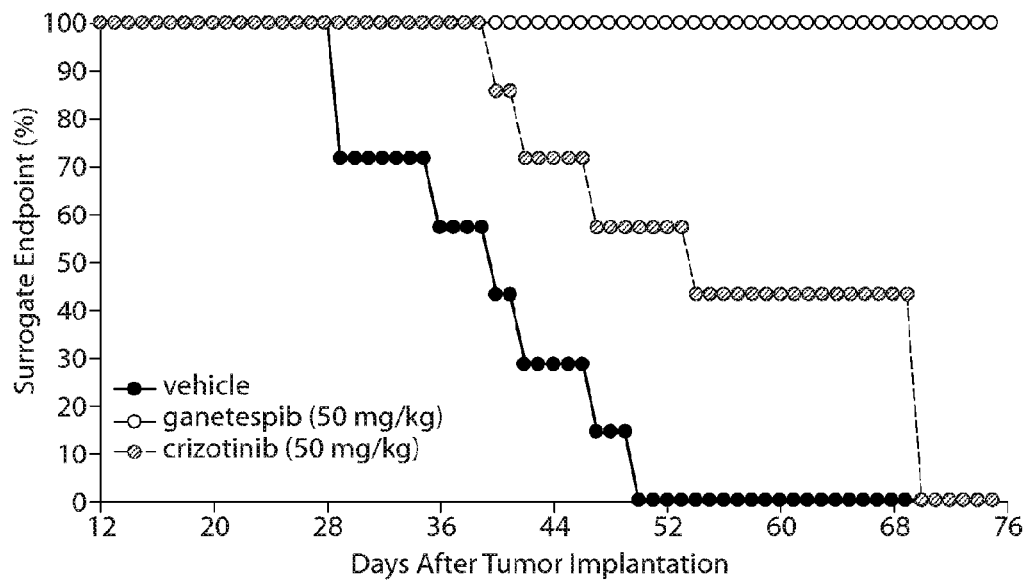
FIG. 14 is a graph demonstrating how ganetespib extended survival compared to crizotinib in H3122 xenograft models. Animals implanted with H3122 xenografts were dosed with vehicle, ganetespib (50 mg/kg, 1×/wk) or crizotinib (50 mg/kg, 5×/wk) and continued on study until tumors reached 1500 mm$^3$ or if the animals were lost.
Figure 15:
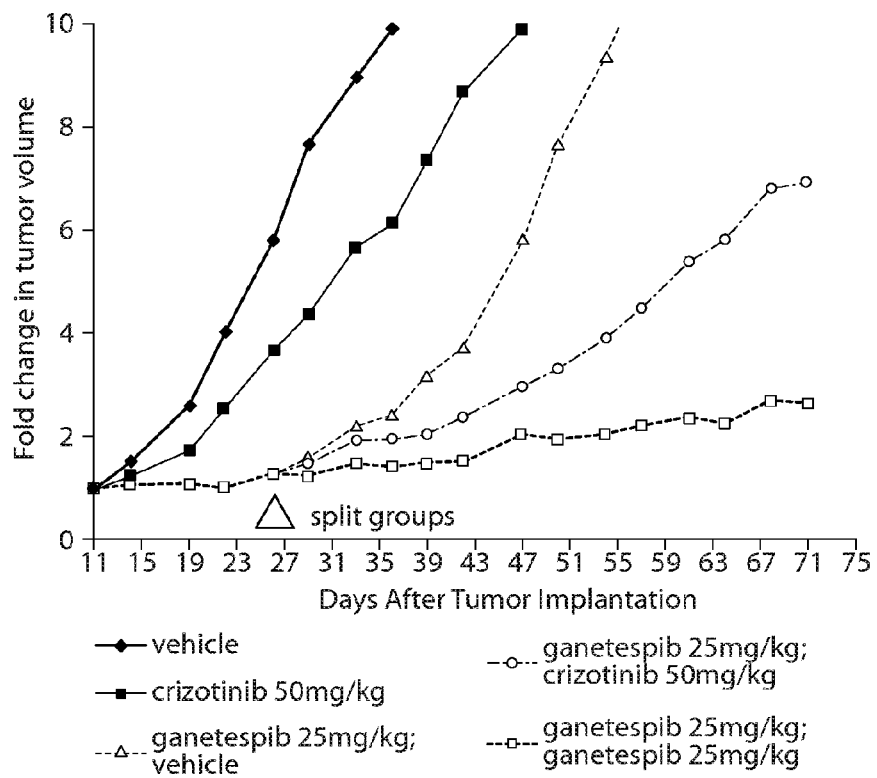
FIG. 15 is a graph comparing ALK+ tumors retained sensitivity to crizotinib after ganetespib treatment. SCID mice, implanted with H3122 xenografts, were treated with vehicle or crizotinib throughout the study or ganetespib until tumors grew >20% in volume (26 days), whereby the animals were split into 3 randomized groups and subsequently treated with vehicle, crizotinib or ganetespib as shown.

Moreover, ganetespib increased the survival of animals bearing ALK+NSCLC xenografts compared to crizotinib. From the results, 50% of animals dosed with vehicle died on day 40, while crizotinib extended survival to 54 days. As of day 75, none of the animals treated with ganetespib had been lost on study (FIG. 14). In the study, it was shown that tumors progressing (>20% increase in volume) on ganetespib rapidly progress if given vehicle, remained fairly stable if continued on ganetespib and showed an intermediary response when given crizotinib suggesting that ganetespib does not negatively affect ALK itself and subsequent crizotinib exposure. Furthermore, prior ganetespib exposure appeared to extend the overall duration of crizotinib efficacy in comparison to tumors exposed to crizotinib alone (FIG. 15).

Figure 16A:
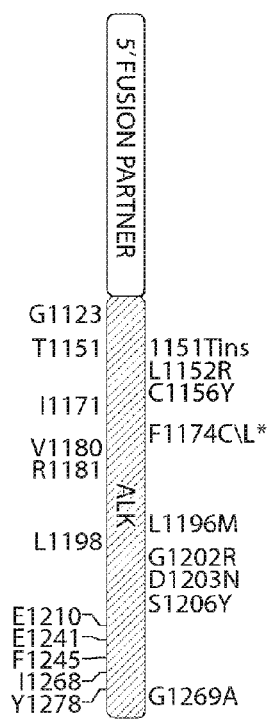
FIG. 16A is an illustration adapted from *Nature Reviews Clinical Oncology* 9, 268-277 (May 2012) listing crizotinib-resistance mutations that have been identified in ALK+ cancers.
Figure 16B:
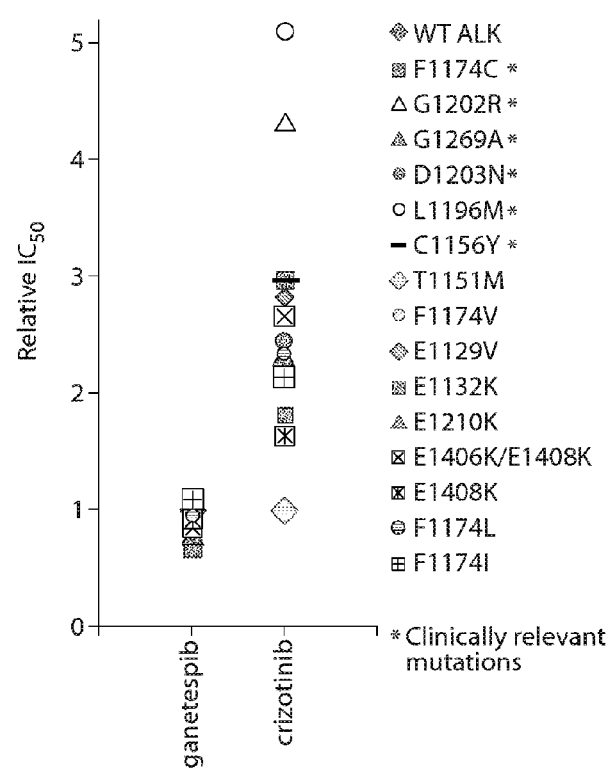
FIG. 16B is a graph showing how ganetespib displayed equal activity in crizotinib-sensitive and crizotinib-resistant NPM-ALK Ba/F3 cells, regardless of secondary ALK mutation.
Figure 17:
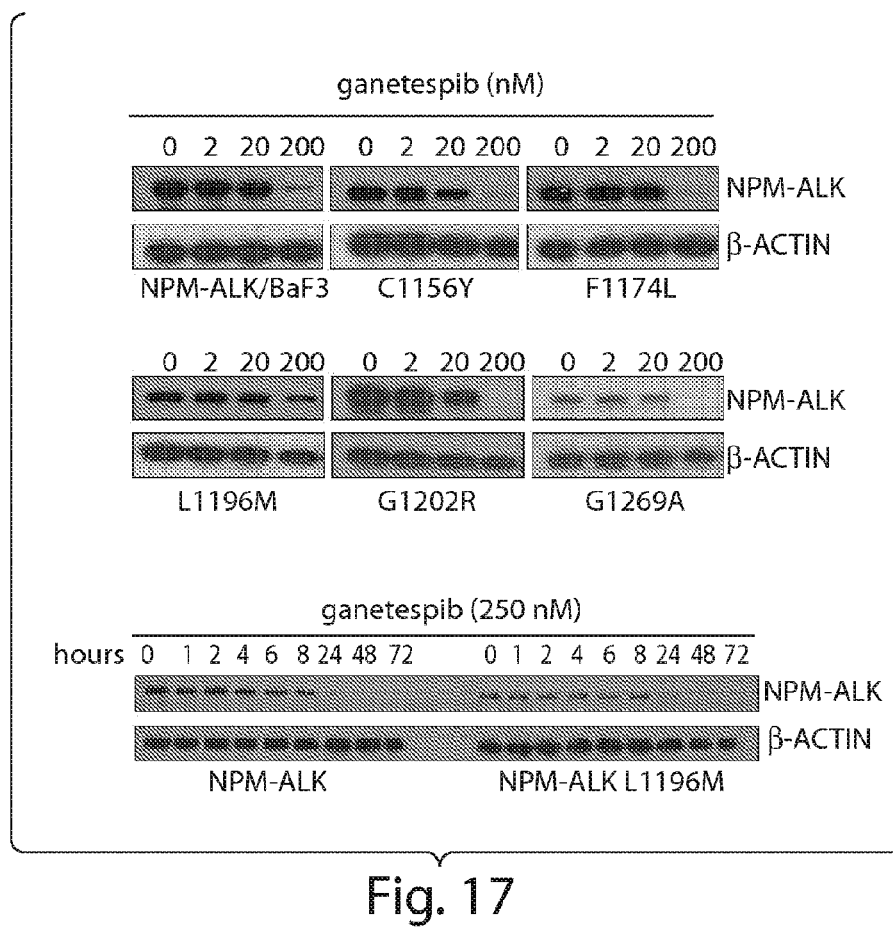
FIG. 17 shows SDS-PAGE images of experiments in certain cell lines illustrating how ganetespib exhibits comparable concentration and time dependent depletion of NPM-ALK and mutant NPM-ALK.
Figure 18:
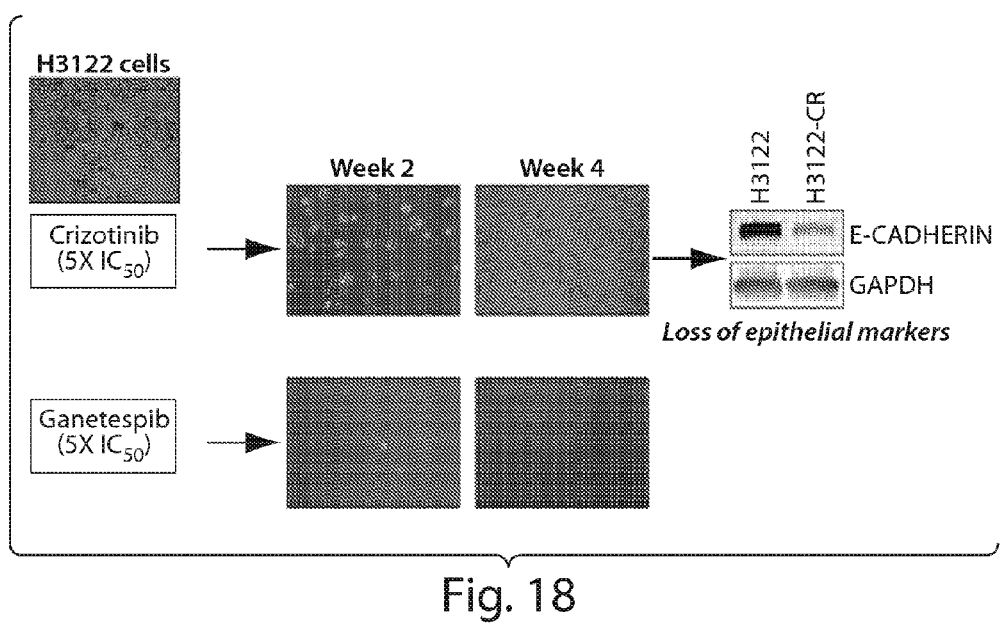
FIG. 18 is an illustration crizotinib induced morphological and molecular characteristics associated with epithelial-mesenchymal transition and acquisition of metastatic properties.
Figure 19:
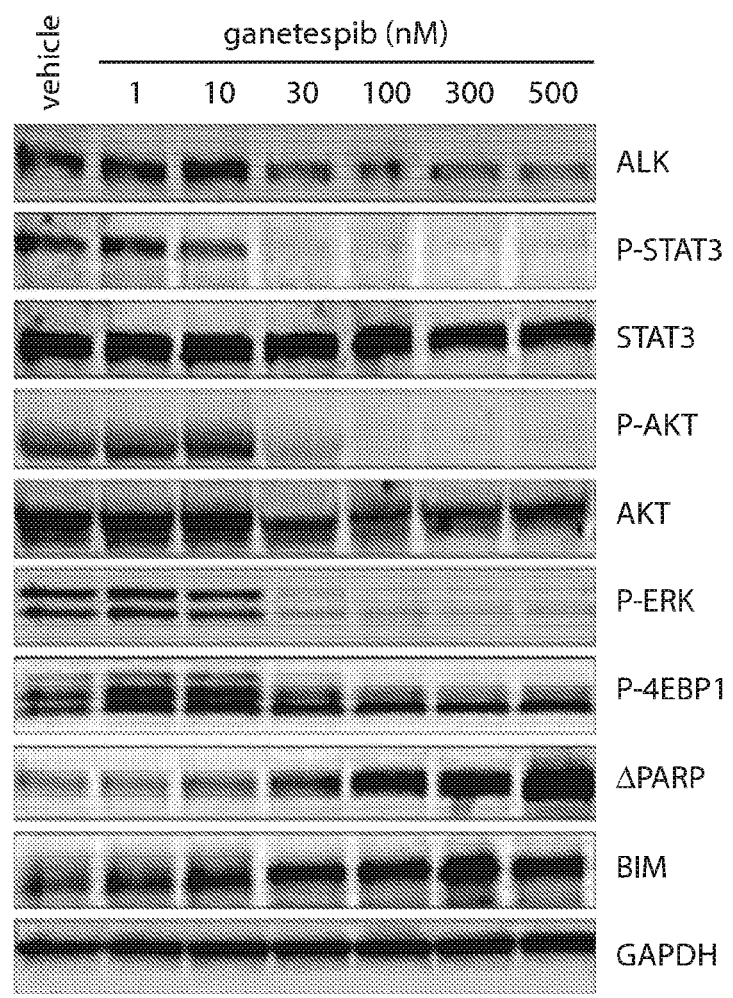
FIG. 19 SDS-PAGE images of experiments in certain cell lines illustrating how ganetespib induces degradation of ALK and inactivation of downstream effectors in NB-39-nu cells.
Figure 20:
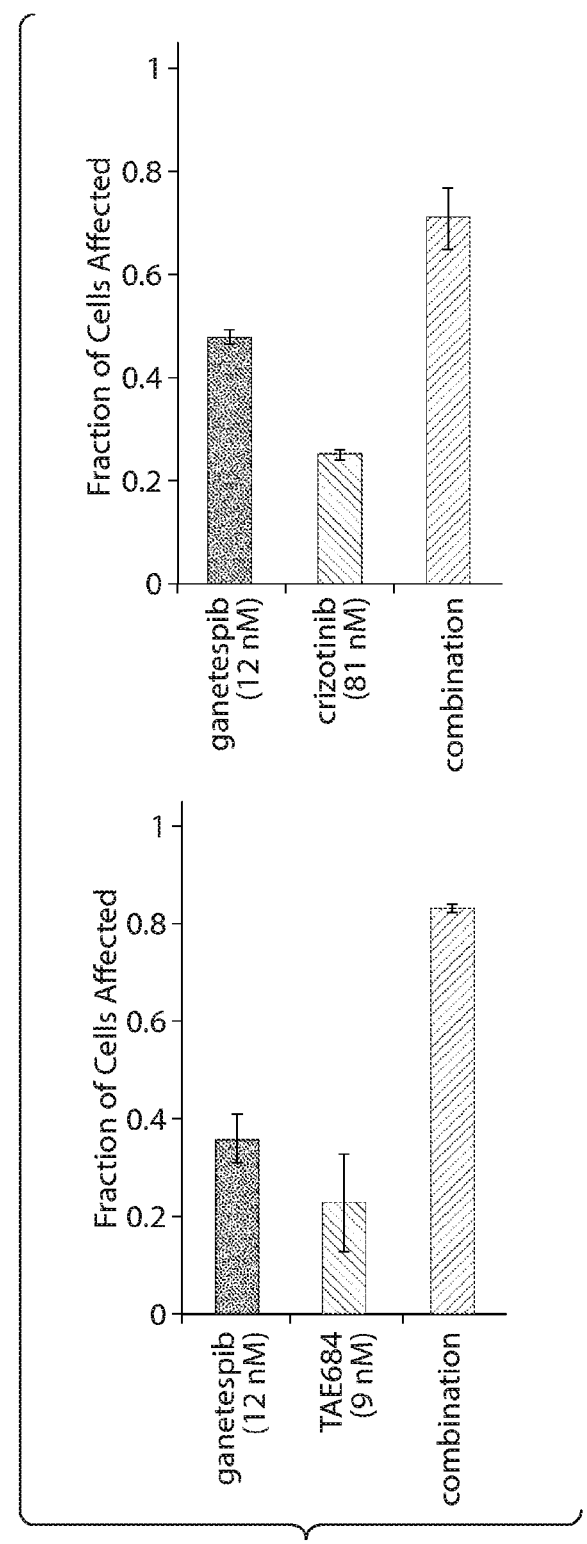
FIG. 20 illustrates graphs comparing ganetespib, the ALK inhibitors crizotinib and TAE684 (CAS No. 761439-42-3, also called NVP-TAE684, is a highly potent and selective small molecule ALK inhibitor) singly and in combination in NB-39-nu cells. It can be seen that ALK inhibitors enhanced the anticancer actions of ganetespib.

Ganetespib retained activity against NPM-ALK-transformed cells bearing secondary ALK mutations that confer crizotinib resistance. One common mechanism leading to acquired resistance to ALK TKIs is the emergence of secondary point mutations within the kinase domain. Experiments were performed in BaF3 cells oncogenically transformed by engineered expression of the lymphoma-associated NPM-ALK fusion kinase in an effort to determine the potential impact of such mutational changes on ganetespib activity. NPM-ALK-expressing BaF3 cells were exposed in culture to a variety of concentrations of crizotinib until the emergence of viable cell pools, which were then subjected to limiting dilution to isolate crizotinib-resistant clones. As shown in FIG. 16, a spectrum of point mutations located in the ALK kinase domain and involving 15 different substitutions were associated with crizotinib resistance. The crizotinib-sensitive parental NPM-ALK/BaF3 cells used in these experiments demonstrated a crizotinib $IC_{50}$ value of ~370 nM. By contrast, the clones harboring the various ALK mutations exhibited varying degrees of resistance, with relative $IC_{50}$ values ranging from approximately 1.6-fold (E1408K, E1132K) to 4-5- fold (G1202R; L1196M) higher (FIG. 16). Experiments were also performed to examine whether crizotinib-resistant NPM-ALK/BaF3 cells demonstrated sensitivity to Hsp90 inhibition. Crizotinib-sensitive NPM-ALK/BaF3 cells were also sensitive to ganetespib ($IC_{50}$ value 21 nM). Notably, all of the crizotinib-resistant NPM-ALK/BaF3 clones retained high sensitivity to ganetespib. Indeed, the $IC_{50}$ values were essentially identical to that of NPM-ALK/BaF3. Consistent with these observations, NPM-ALK protein degradation following ganetespib treatment showed similar dose-dependent responses regardless of the presence or identity of the crizotinib-resistance mutation (FIG. 17). The kinetics of protein degradation for NPM-ALK/BaF3 and NPM-ALK/BaF3 containing the L1196M gatekeeper mutation following exposure to ganetespib (250 nM) is shown in FIG. 17. Amplification of ALK has also been implicated in the pathology of other tumor types, including neuroblastoma and inflammatory breast cancer. To examine the effects of ganetespib in ALK-amplified tumor cells, the NB-39-nu neuroblastoma cell line (which expresses 30-40 copies of the ALK gene per cell) were with graded concentrations of ganetespib, and it was found that these cells were acutely sensitive to drug exposure, with a viability $IC_{50}$ value of 10 nM. Ganetespib treatment resulted in a dose-dependent degradation of this oncogenic driver, as well as loss of downstream effector signaling (activated STAT3, AKT and ERK) and concomitant induction of the apoptotic markers BIM and cleaved PARP (FIG. 19).

Conclusions:

Ganetespib induced the degradation of EML4-ALK protein by targeting the chaperone dependency of ALK, rather than the kinase directly, which is distinct from crizotinib. Unlike crizotinib or other direct ALK inhibitors, the destabilization of ALK signaling by ganetespib occurred simultaneous with the degradation of other key oncogenic signaling proteins reliant on Hsp90. Ganetespib demonstrated better ALK+ tumor growth suppression compared with crizotinib. Frontline ganetespib treatment prolonged overall efficacy of crizotinib. The complementary actions of directed ALK inhibition with crizotinib and indirect ALK inhibition with ganetespib result in synergistic anticancer activity. Moreover, ganetespib is equally potent in ALK inhibitor sensitive and resistant cancer cells regardless of ALK mutation status.

All publications, patent applications, patents, and other documents cited herein are incorporated by reference in their entirety. In case of conflict, the present specification, including definitions, will control. In addition, the materials, methods, and examples throughout the specification are illustrative only and not intended to be limiting in any way.

What is claimed is:

1. A method of treating cancer in a subject, comprising administering to a subject an effective amount of an Hsp90 inhibitor according to the following formulae:

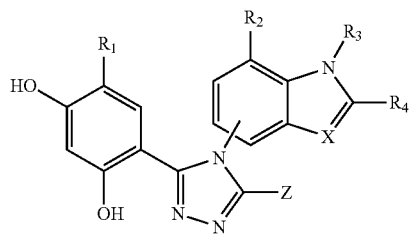

(I)

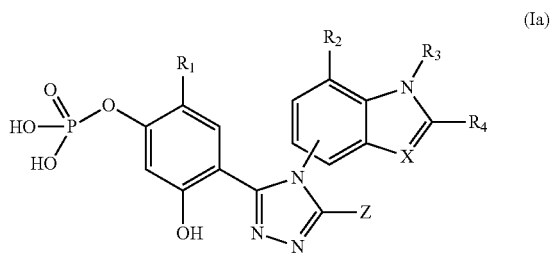

(Ia)

or a tautomer, or a pharmaceutically acceptable salt thereof, wherein:

$Z$ is OH, SH, or $NH_2$;

$X$ is $CR_4$ or N;

$R_1$ is —H, —OH, —SH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, halo, cyano, nitro, guanidino, a haloalkyl, a heteroalkyl, an alkoxy or cycloalkoxy, a haloalkoxy, —$NR_{10}R_{11}$, —$OR_7$, —$C(O)R_7$, —$C(O)OR_7$, —$C(S)R_7$, —$C(O)SR_7$, —$C(S)SR_7$, —$C(S)OR_7$, —$C(S)NR_{10}R_{11}$, —$C(NR_8)OR_7$, —$C(NR_8)R_7$, —$C(NR_8)NR_{10}R_{11}$, —$C(NR_8)SR_7$, —$OC(O)R_7$, —$OC(O)OR_7$, —$OC(S)OR_7$, —$OC(NR_8)OR_7$, —$SC(O)R_7$, —$SC(O)OR_7$, —$SC(NR_8)OR_7$, —$OC(S)R_7$, —$SC(S)R_7$, —$SC(S)OR_7$, —$OC(O)NR_{10}R_{11}$, —$OC(S)NR_{10}R_{11}$, —$OC(NR_8)NR_{10}R_{11}$, —$SC(O)NR_{10}R_{11}$, —$SC(NR_8)NR_{10}R_{11}$, —$SC(S)NR_{10}R_{11}$, —$OC(NR_8)R_7$, —$SC(NR_8)R_7$, —$C(O)NR_{10}R_{11}$, —$NR_8C(O)R_7$, —$NR_7C(S)R_7$, —$NR_7C(S)OR_7$, —$NR_7C(NR_8)R_7$, —$NR_7C(O)OR_7$, —$NR_7C(NR_8)OR_7$, —$NR_7C(O)NR_{10}R_{11}$, —$NR_7C(S)NR_{10}R_{11}$, —$NR_7C(NR_8)NR_{10}R_{11}$, —$SR_7$, —$S(O)_pR_7$, —$OS(O)_pR_7$, —$OS(O)_pOR_7$, —$O(O)_pNR_{10}R_{11}$, $S(O)_pOR_7$, —$NR_8S(O)_pR_7$, —$NR_7S(O)_pNR_{10}R_{11}$, —$NR_7S(O)_pOR_7$, —$S(O)_pNR_{10}R_{11}$, —$SS(O)_pR_7$, —$SS(O)_pOR_7$, —$SS(O)_pNR_{10}R_{11}$, —$OP(O)(OR_7)_2$, or —$SP(O)(OR_7)_2$;

$R_2$ is —H, —OH, —SH, —$NR_7H$, —$OR_{15}$, —$NHR_{15}$, —$O(CH_2)_mOH$, —$O(CH_2)_mSH$, —$O(CH_2)_mNR_7H$, —$S(CH_2)_{m0}H$, —$S(CH_2)_mSH$, —$S(CH_2)_mNR_7H$, —$OC(O)NR_{10}R_{11}$, —$SC(O)NR_{10}R_{11}$, —$NR_7C(O)NR_{10}R_{11}$, —$OC(O)R_7$, —$SC(O)R_7$, —$NR_7C(O)R_7$, —$OC(O)OR_7$, —$SC(O)OR_7$, —$NR_7C(O)OR_7$, —$OCH_2C(O)R_7$, —$SCH_2C(O)R_7$, —$NR_7CH_2C(O)R_7$, —$OCH_2C(O)OR_7$, —$SCH_2C(O)OR_7$, —$NR_7CH_2C(O)OR_7$, —$OCH_2C(O)NR_{10}R_{11}$, —$SCH_2C(O)NR_{10}R_{11}$, —$NR_7CH_2C(O)NR_{10}R_{11}$, —$OS(O)_pR_7$, —$SS(O)_pR_7$, —$NR_7S(O)_pR_7$, —$OS(O)_pNR_{10}R_{11}$, —$SS(O)_pNR_{10}R_{11}$, —$NR_7S(O)_pNR_{10}R_{11}$, —$OS(O)_pOR_7$, —$SS(O)_pOR_7$, —$NR_7S(O)_pOR_7$, —$OC(S)R_7$, —$SC(S)R_7$, —$NR_7C(S)R_7$, —$OC(S)OR_7$, —$SC(S)OR_7$, —$NR_7C(S)OR_7$, —$OC(S)NR_{10}R_{11}$, —$SC(S)NR_{10}R_{11}$, —$NR_7C(S)NR_{10}R_{11}$, —$OC(NR_8)R_7$, —$SC(NR_8)R_7$, —$NR_7C(NR_8)R_7$, —$OC(NR_8)OR_7$, —$SC(NR_8)OR_7$, —$NR_7C(NR_8)OR_7$, —$OC(NR_8)NR_{10}R_{11}$, —$SC(NR_8)NR_{10}R_{11}$, or —$NR_7C(NR_8)NR_{10}R_{11}$;

$R_3$ is —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, a haloalkyl, a heteroalkyl, —C(O)R$_7$, —(CH$_2$)$_m$C(O)OR$_7$, —C(O)OR$_7$, —OC(O)R$_7$, —C(O)NR$_{10}$R$_{11}$, —S(O)$_p$R$_7$, —S(O)$_p$OR$_7$, or —S(O)$_p$NR$_1$OR$_{11}$;

R$_4$ is —H, —OH, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, an optionally substituted heteraralkyl, hydroxyalkyl, alkoxyalkyl, halo, cyano, nitro, guanidino, a haloalkyl, a heteroalkyl, —C(O)R$_7$, —C(O)OR$_7$, —OC(O)R$_7$, —C(O)NR$_{10}$R$_{11}$, —NR$_8$C(O)R$_7$, —SR$_7$, —S(O)$_p$R$_7$, —OS(O)$_p$R$_7$, —S(O)$_p$OR$_7$, —NR$_8$S(O)$_p$R$_7$, —S(O)$_p$NR$_{10}$R$_{11}$, or R$_3$ and R$_4$ taken together with the carbon atoms to which they are attached form an optionally substituted cycloalkenyl, an optionally substituted aryl, an optionally substituted heterocyclyl, or an optionally substituted heteroaryl;

R$_7$ and R$_5$, for each occurrence, are, independently, —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl;

R$_{10}$ and R$_{11}$, for each occurrence, are independently —H, an optionally substituted alkyl, an optionally substituted alkenyl, an optionally substituted alkynyl, an optionally substituted cycloalkyl, an optionally substituted cycloalkenyl, an optionally substituted heterocyclyl, an optionally substituted aryl, an optionally substituted heteroaryl, an optionally substituted aralkyl, or an optionally substituted heteraralkyl; or R$_{10}$ and R$_{11}$, taken together with the nitrogen to which they are attached, form an optionally substituted heterocyclyl or an optionally substituted heteroaryl;

R$_{15}$, for each occurrence, is independently, a lower alkyl;

p, for each occurrence, is, independently, 1 or 2; and m, for each occurrence, is, independently, 1, 2, 3, or 4, wherein the subject has cancer with a mutation in ALK.

2. The method of claim 1, wherein the cancer is selected from the group consisting of lung cancer, breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, and non-small cell lung cancer (NSCLC).

3. The method of claim 2, wherein the cancer has been previously treated with an ALK inhibitor and is no longer responsive to the previous treatment.

4. The method of claim 3, wherein the ALK inhibitor is crizotinib.

5. The method of claim 1, wherein the Hsp90 inhibitor is 3-(2,4-dihydroxy-5-isopropyl-phenyl)-4-(1-methyl-indol-5-yl)-5-hydroxy-[1,2,4]triazole or a tautomer or a pharmaceutically acceptable salt thereof.

6. The method of claim 1, wherein the Hsp90 inhibitor is 5-hydroxy-4-(5-hydroxy-4-(1-methyl-1H-indol-5-yl)-4H-1,2,4-triazol-3-yl)-2-isopropylphenyl dihydrogen phosphate, or a tautomer, or a pharmaceutically acceptable salt thereof.

7. The method of claim 1, wherein the cancer is non-small cell lung cancer.

8. The method of claim 7, wherein the non-small cell lung cancer has an ALK-EML4 fusion.

9. The method of claim 7, wherein the non-small cell lung cancer has an NPM-ALK fusion.

10. The method of claim 7, wherein the non-small cell lung cancer has a KIF5B-ALK fusion.

11. The method of claim 7, wherein the non-small cell lung cancer has a TFG-ALK fusion.

12. The method of claim 1, wherein the Hsp90 inhibitor is administered in combination with one or more additional therapeutic agents.

13. The method of claim 12, wherein the one or more therapeutic agents is selected from the group consisting of erlotinib, bevacizumab, paclitaxel, docetaxel, cisplatin, carboplatin, Abraxane®, pemetrexed, bortezomib, topotecan, cetuximab, gemcitabine, crizotinib and tetracycline.

14. The method of claim 13, wherein the one or more therapeutic agents is erlotinib or bevacizumab.

15. The method of claim 13, wherein the one or more therapeutic agents is docetaxel, paclitaxel or Abraxane®.

16. The method of claim 13, wherein the one or more therapeutic agents is crizotinib.

17. A method of treating cancer in a subject, comprising administering to the subject an effective amount of 3-(2,4-dihydroxy-5-isopropyl-phenyl)-4-(1-methyl-indol-5-yl)-5-hydroxy-[1,2,4]triazole or a tautomer or a pharmaceutically acceptable salt thereof, in combination with crizotinib, wherein the subject has a cancer with a mutation in c-MET.

18. The method of claim 17, wherein the cancer is selected from the group consisting of lung cancer, breast cancer, gastric cancer, colorectal cancer, pancreatic cancer, ocular melanoma, prostate cancer, gastrointestinal stromal tumors (GIST), advanced esophagogastric cancer, melanoma, hepatocellular cancer, solid tumor, liver cancer, head and neck cancer, small cell lung cancer, and non-small cell lung cancer (NSCLC).

19. The method of claim 18, wherein the cancer is non-small cell lung cancer.

20. The method of claim 18, wherein the cancer is breast cancer.

21. A method of treating cancer in a subject, comprising administering to the subject ganetespib or a tautomer or a pharmaceutically acceptable salt thereof, in the amount from about 100 mg/m$^2$ to about 500 mg/m$^2$, wherein the subject has a cancer with a mutation in ALK.

22. The method of claim 21, wherein the cancer is non-small cell lung cancer.

23. The method of claim 21, wherein further comprising administering crizotinib to the subject.

* * * * *

UNITED STATES PATENT AND TRADEMARK OFFICE
CERTIFICATE OF CORRECTION

PATENT NO.         : 8,906,885 B2                                        Page 1 of 1
APPLICATION NO.    : 14/131183
DATED              : December 9, 2014
INVENTOR(S)        : Iman El-Hariry et al.

It is certified that error appears in the above-identified patent and that said Letters Patent is hereby corrected as shown below:

In the Claims:

At column 68, claim number 1, line number 41, delete "-O(O)$_p$NR$_{10}$R$_{11}$," and replace with --"-OS(O)$_p$NR$_{10}$R$_{11}$,"--;

At column 68, claim number 1, line number 44, after "-OR$_{15}$," and before "-NHR$_{15}$," insert --"SR$_{15}$,"--;

At column 68, claim number 1, line number 46, delete "-S(CH$_2$)$_{mo}$H," and replace with --"-S(CH$_2$)$_m$OH,"--;

At column 69, claim number 1, line numbers 5-6, delete "-S(O)$_p$NR$_1$OR$_{11}$;" and replace with --"-S(O)$_p$NR$_{10}$R$_{11}$;"--.

Signed and Sealed this
Thirty-first Day of March, 2015

Michelle K. Lee
*Director of the United States Patent and Trademark Office*